United States Patent
Beissinger et al.

(10) Patent No.: US 9,394,534 B2
(45) Date of Patent: Jul. 19, 2016

(54) METHOD AND MEANS FOR ENRICHMENT, REMOVAL AND DETECTION OF GRAM-POSITIVE BACTERIA

(75) Inventors: Martina Beissinger, Regensburg (DE); Stefan Miller, Regensburg (DE); Anja Philipp, Regensburg (DE); Michael Schütz, Regensburg (DE)

(73) Assignee: BIOMERIEUX S.A., Marcy l'Etoile (FR)

( * ) Notice: Subject to any disclaimer, the term of this patent is extended or adjusted under 35 U.S.C. 154(b) by 1110 days.

(21) Appl. No.: 12/520,731

(22) PCT Filed: Dec. 21, 2007

(86) PCT No.: PCT/DE2007/002320
§ 371 (c)(1),
(2), (4) Date: Dec. 8, 2009

(87) PCT Pub. No.: WO2008/077397
PCT Pub. Date: Jul. 3, 2008

(65) Prior Publication Data
US 2010/0092968 A1      Apr. 15, 2010

(30) Foreign Application Priority Data
Dec. 22, 2006 (DE) .......................... 10 2006 061 002

(51) Int. Cl.
| | | |
|---|---|---|
| *C12Q 1/68* | (2006.01) | |
| *C12N 9/00* | (2006.01) | |
| *G01N 33/554* | (2006.01) | |
| *G01N 33/569* | (2006.01) | |
| *C12N 9/96* | (2006.01) | |
| *C12N 1/20* | (2006.01) | |
| *C12N 15/00* | (2006.01) | |
| *C07H 21/04* | (2006.01) | |
| *C12N 9/88* | (2006.01) | |
| *C07K 14/005* | (2006.01) | |
| *C07K 14/195* | (2006.01) | |
| *C07K 14/32* | (2006.01) | |

(52) U.S. Cl.
CPC .............. *C12N 9/88* (2013.01); *C07K 14/005* (2013.01); *C07K 14/195* (2013.01); *C07K 14/32* (2013.01); *G01N 33/56911* (2013.01); *C07K 2319/035* (2013.01); *C07K 2319/70* (2013.01); *C12N 2795/10022* (2013.01); *G01N 2469/10* (2013.01)

(58) Field of Classification Search
CPC ... A61K 38/00; A61K 2300/00; A61K 39/00; A61K 35/76; A61K 38/46; A61K 8/66; C12N 9/503; C12N 7/00; C12N 9/14; C12N 9/88; C12N 2795/00011; C07K 14/005; C07K 2319/00; C12Q 1/04; C12Q 1/689; C12Q 1/70; C12Q 1/37; C12Q 2563/131; C12Q 2563/149; C12Y 304/24075; C12Y 305/01028

See application file for complete search history.

(56) References Cited

U.S. PATENT DOCUMENTS

| | | | |
|---|---|---|---|
| 5,252,466 A | 10/1993 | Cronan, Jr. | ................... 435/69.7 |
| 5,874,239 A | 2/1999 | Schatz | ........................ 435/69.1 |
| 6,699,679 B2 | 3/2004 | Chen et al. | .................... 435/7.32 |
| 7,527,979 B2 | 5/2009 | Haik | ............................. 436/526 |
| 2004/0197833 A1 | 10/2004 | Loessner | ........................ 435/7.2 |
| 2005/0004030 A1* | 1/2005 | Fischetti et al. | ................ 514/12 |

FOREIGN PATENT DOCUMENTS

| | | |
|---|---|---|
| DE | 198 37 751 | 2/2000 |
| EP | 1147419 | 10/2001 |
| EP | 1399551 | 11/2006 |
| JP | 4-507341 | 12/1992 |
| WO | WO 90/14431 | 11/1990 |
| WO | WO 00/11472 | 3/2000 |
| WO | WO 03/066845 | 8/2003 |
| WO | WO 2004/005482 | 1/2004 |
| WO | WO 2004/020635 | 3/2004 |
| WO | WO 2004/027020 | 4/2004 |
| WO | WO 2004/088321 | 10/2004 |
| WO | WO 2004/106367 | 12/2004 |
| WO | WO 2007/022768 | 3/2007 |

OTHER PUBLICATIONS

Consler et al., "Properties and purification of an active biotinylated lactose permease from *Excherichia coli*," *Proc. Natl. Acad. Sci. USA*, 90(15)::6934-6938, 1993.
Diaz et al., "Chimeric phage-bacterial enzymes: a clue to the modular evolution of genes," *Proc. Natl. Acad. Sci. USA*, 87:8125-8129, 1990.
Finn et al., "Pfam: clans, web tools and services," *Nucleic Acids Research*, 34:D247-D251, 2006.
Fluit et al., "Detection of Listeria monocytogenes in cheese with the magnetic immuno-polymerase chain reaction assay," *Appl. Environ. Microbiol.*, 59:1289-1293, 1993.
Garcia et al., "Modular organization of the lytic enzymes of *Streptococcus pneumoniae* and its bacteriophages," *Gene*, 86:81-88, 1990.
Garcia et al., "Molecular evolution of lytic enzymes of *Streptococcus pneumoniae* and its bacteriophages," *Proc. Natl. Acad. Sci USA*, 85:914-918, 1988.

(Continued)

*Primary Examiner* — Iqbal H Chowdhury
(74) *Attorney, Agent, or Firm* — Parker Highlander PLLC

(57) ABSTRACT

The present invention relates to polypeptides comprising a enzymatically non-active cell wall binding domain of an endolysin or another cell wall lysing enzyme, and a sequence according to SEQ ID NO: 1 or derivatives thereof, wherein the polypeptide besides the cell wall binding domain comprises no further domains of an endolysin, as well as means for their preparation. The present invention further relates to methods for binding, enriching, removing from a sample, capturing and/or detecting bacteria, particularly gram positive bacteria.

10 Claims, 25 Drawing Sheets

(56) References Cited

OTHER PUBLICATIONS

Figure 1A:
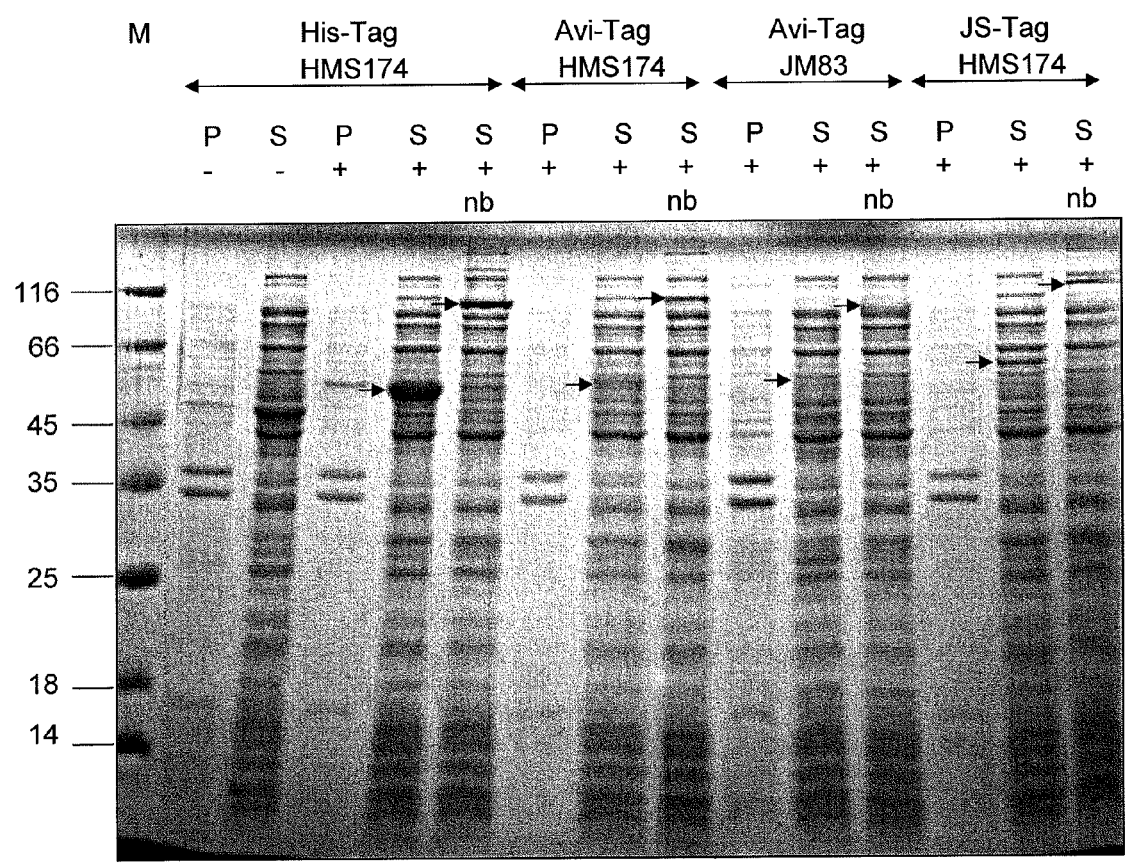

Hawkes et al., "Ultrasonic deposition of cells on a surface," *Biosens. Bioelectron.*, 19:1021-1028, 2004.
Jockel et al., "Membrane topology of the beta-subunit of the oxalocetate decarboxylase na+ pump from Klebsiella pneumoniae," *Biochemistry*, 38(41):13461-13472, 1999.
Jung et al., "Evaluation of antibodies for immunomagnetic separation combined with flow cytometry detection of Listeria monocytogenes," *J. Food Prot.*, 66:1283-1287, 2003.
Letunic et al., "SMART 5: domains in the context of genomes and networks," *Nucleic Acids Res.*, 34:D257-D260, 2006.
Loessner et al., "C-terminal domains of Listeria monocytogenes bacteriophage murein hydrolases determine specific recognition and high-affinity binding to bacterial cell wall carbohydrates," *Mol. Microbiol.*, 44:335-349, 2002.
Loessner, "Bacteriophage endolysins—current state of research and applications," *Curr. Opin. Microbiol.*, 8:480-487, 2005.
Marchler-Bauer et al., "CDD: a Conserved Domain Database for protein classification," *Nucleic Acids Research*, 33:D192-D196, 2005.
Rasko et al., "Genomics of the Bacillus cereus group of organisms," *FEMS Microbiol. Reviews*, 29:303-329, 2005.
Schultz et al., "SMART, a simple modular architecture research tool: identification of signaling domains," *Proc. Natl. Acad. Sci. USA*, 95:5857-5864, 1998.
Stolz et al., "Bacteriophage lambda ," *FEBS Lett.*, 440:213-217, 1998.
Yoong et al., "Identification of a broadly active phage lytic enzyme with lethal activity against antibiotic-resistant Enterococcus faecalis and Enterococcus faecium," *J. Bact.*, 186:4808-4812, 2004.

"Amidase (peptidoglycan hydrolase) [*Staphylococcus aureus* bacteriophage PVL]," NCBI Reference Sequence: NP_058463.1, 2006.
"AtlE protein [*Staphylococcus epidermidis*]," GenBank: CAI59555. 1, 2006.
Endolysin [Enterococcus faecalis V583], NCBI Reference Sequence: NP_815016.1, 2005.
"Endolysin, putative [Enterococcus faecalis V583]," NCBI Reference Sequence: NP_814147.1, 2005.
"phiSLT ORF484-like protein, lysine [*Staphylococcus aureus* subsp. Aureus USA300]," NCBI Reference Sequence: YP_494080.1, 2006.
Kaishi, "Flavobacterium," *Bioscience, Biotechnology and Biochemistry*, 66(7):1121-1122, 1992.
Loessner et al., "Heterogeneous endolysins in *Listeria* monocytogenes bacteriophages: a new class of enzymes and evidence for conserved holing genes within the siphoviral lysis cassettes," *Mol. Microbiol.*, 16(6):1231-1241, 1995.
Loessner et al., "Three *Bacillus cereus* bacteriophage endolysins are unrelated but reveal high homology to cell wall hydrolases from different bacilli," *J. Bacteriol.*, 179(9):2845-2851, 1997.
Recsei et al., "Cloning, sequence, and expression of the lysostaphin gene from *Staphylococcus simulans*," *Proc. Natl. Acad. Sci. USA*, 84:1127-1131, 1987.
Sugai et al., "Purification and molecular characterization of glycylglycine endopeptidase produced by *Staphylococcus capitis* EPK1," *J. Bacteriol.*, 179(4):1193-1202, 1997.
Yasugi et al., Ed. *Iwanami Dictionary*. Iwananami Shoten: Tokyo, 1997. 1343 and 1538. Print. (English sections only).

* cited by examiner

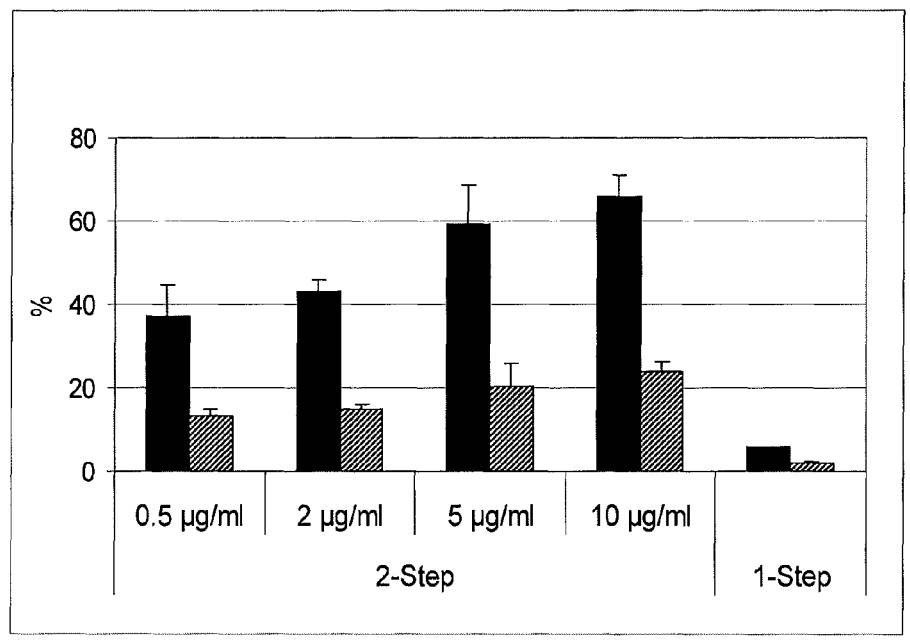
FIG. 3A-B

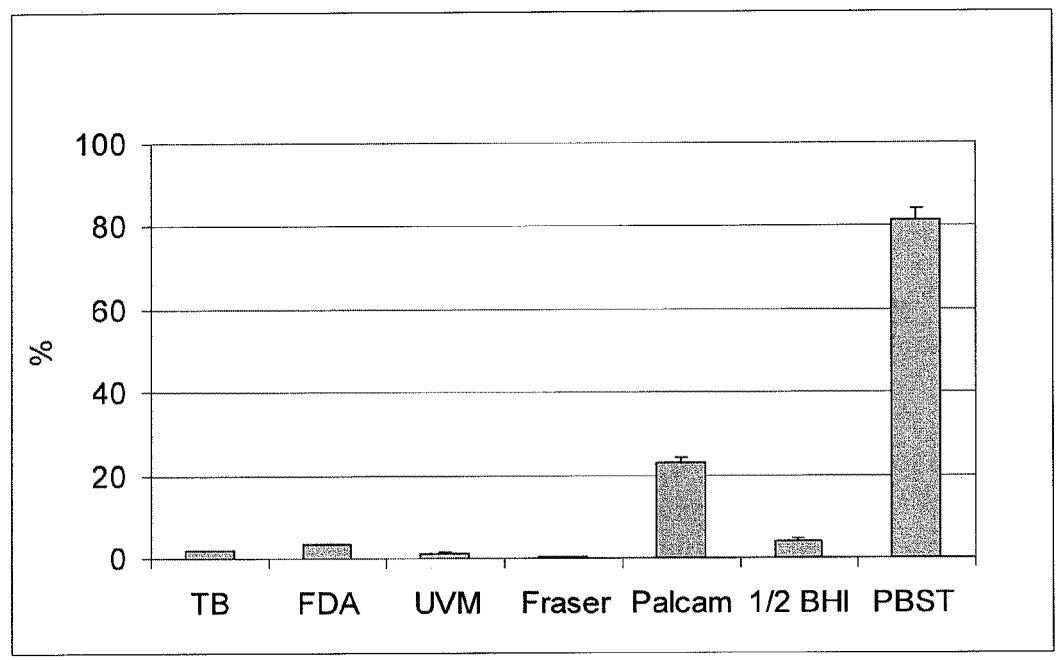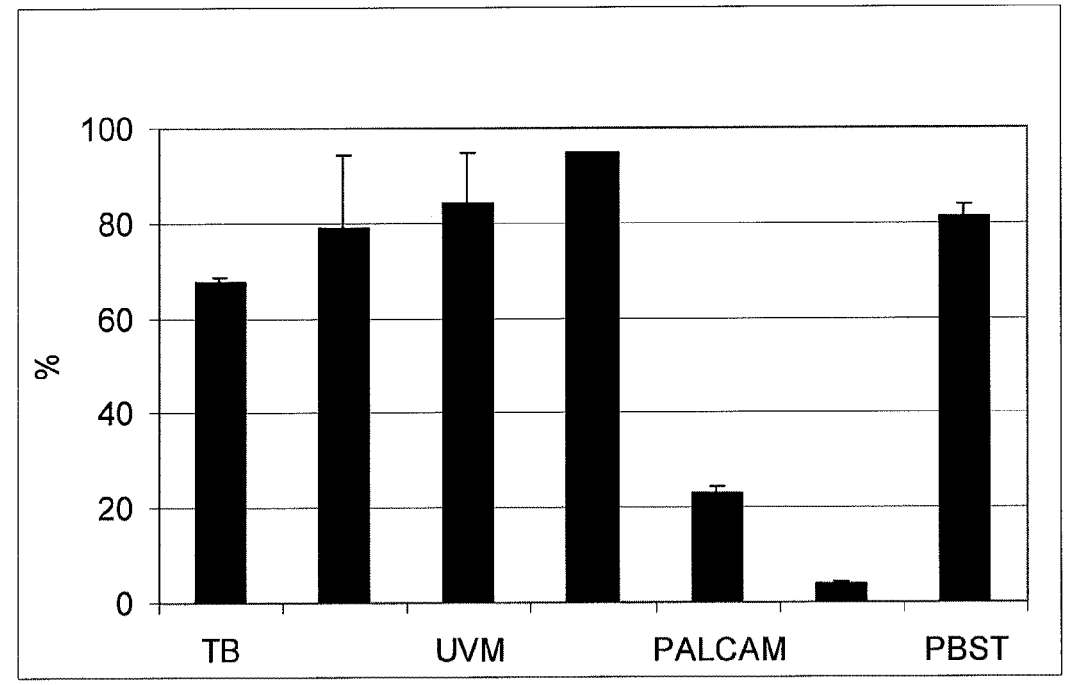
FIG. 7A-B

Detection time

B
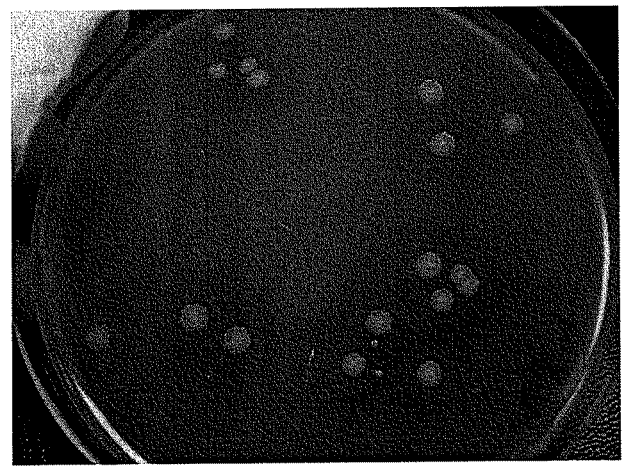
C
FIG. 13B-C

A
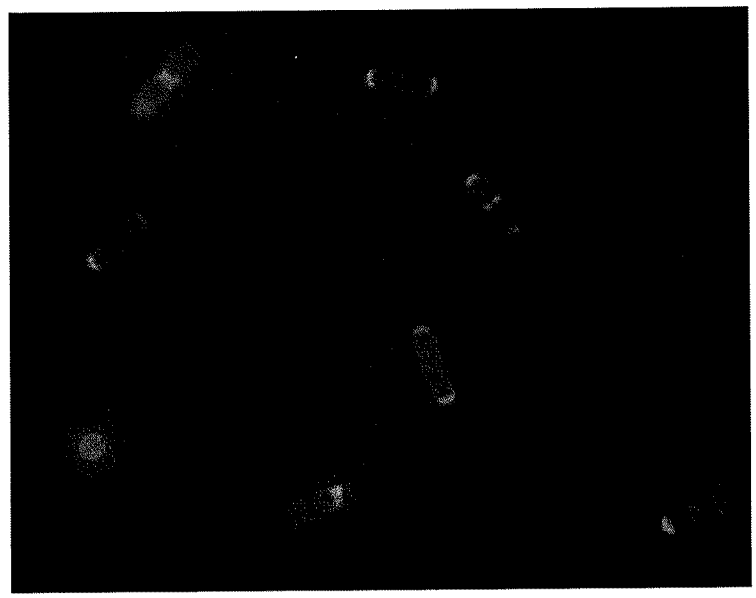
B
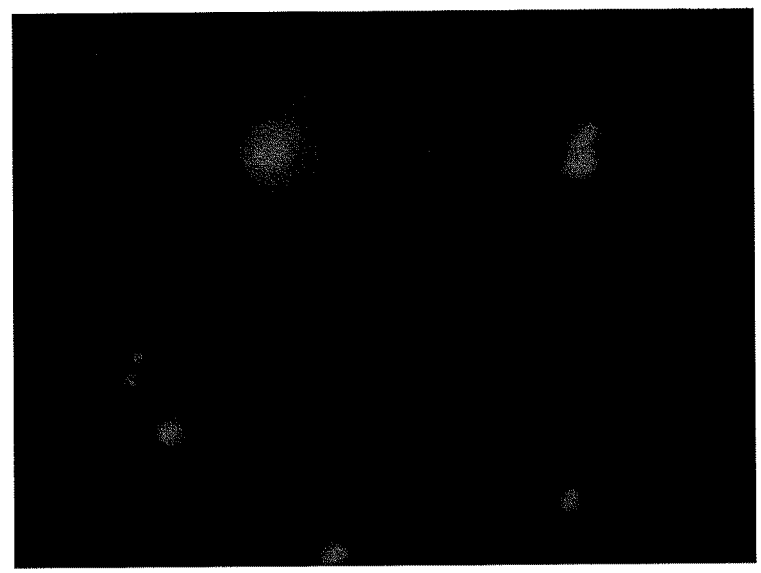
FIG. 15A-B

SEQUENCE LISTING

<160> NUMBER OF SEQ ID NOS: 56

<210> SEQ ID NO 1
<211> LENGTH: 66
<212> TYPE: PRT
<213> ORGANISM: Artificial
<220> FEATURE:
<223> OTHER INFORMATION: Synthetic peptide

<400> SEQUENCE: 1

Val Thr Ala Pro Leu Ala Gly Thr Ile Trp Lys Val Leu Ala Ser Glu
1               5                   10                  15

Gly Gln Thr Val Ala Ala Gly Glu Val Leu Leu Ile Leu Glu Ala Met
            20                  25                  30

Lys Met Glu Thr Glu Ile Arg Ala Ala Gln Ala Gly Thr Val Arg Gly
        35                  40                  45

Ile Ala Val Lys Ala Gly Asp Ala Val Ala Val Gly Glu Thr Leu Met
    50                  55                  60

Thr Leu
65

<210> SEQ ID NO 2
<211> LENGTH: 66
<212> TYPE: PRT
<213> ORGANISM: Klebsiella pneumoniae

```
<400> SEQUENCE: 2

Val Thr Ala Pro Leu Ala Gly Thr Ile Trp Lys Val Leu Ala Ser Glu
1               5                   10                  15

Gly Gln Thr Val Ala Ala Gly Glu Val Leu Leu Ile Leu Glu Ala Met
            20                  25                  30

Lys Met Glu Thr Glu Ile Arg Ala Ala Gln Ala Gly Thr Val Arg Gly
        35                  40                  45

Ile Ala Val Lys Ala Gly Asp Ala Val Ala Val Gly Asp Thr Leu Met
    50                  55                  60

Thr Leu
65

<210> SEQ ID NO 3
<211> LENGTH: 67
<212> TYPE: PRT
<213> ORGANISM: Artificial
<220> FEATURE:
<223> OTHER INFORMATION: Synthetic peptide

<400> SEQUENCE: 3

Val Thr Ala Pro Leu Ala Gly Thr Ile Trp Lys Val Leu Ala Ser Glu
1               5                   10                  15

Gly Gln Thr Val Ala Ala Gly Glu Val Leu Leu Ile Leu Glu Ala Met
            20                  25                  30

Lys Met Glu Thr Glu Ile Arg Ala Ala Gln Ala Gly Thr Val Arg Gly
        35                  40                  45

Ile Ala Val Lys Ala Gly Asp Ala Val Ala Val Gly Glu Thr Leu Met
    50                  55                  60

Thr Leu Val
65

<210> SEQ ID NO 4
<211> LENGTH: 68
<212> TYPE: PRT
<213> ORGANISM: Artificial
<220> FEATURE:
<223> OTHER INFORMATION: Synthetic peptide

<400> SEQUENCE: 4

Val Thr Ala Pro Leu Ala Gly Thr Ile Trp Lys Val Leu Ala Ser Glu
1               5                   10                  15

Gly Gln Thr Val Ala Ala Gly Glu Val Leu Leu Ile Leu Glu Ala Met
            20                  25                  30

Lys Met Glu Thr Glu Ile Arg Ala Ala Gln Ala Gly Thr Val Arg Gly
        35                  40                  45

Ile Ala Val Lys Ala Gly Asp Ala Val Ala Val Gly Glu Thr Leu Met
    50                  55                  60

Thr Leu Val Asp
65

<210> SEQ ID NO 5
<211> LENGTH: 67
<212> TYPE: PRT
<213> ORGANISM: Artificial
<220> FEATURE:
<223> OTHER INFORMATION: Synthetic peptide

<400> SEQUENCE: 5

Met Val Thr Ala Pro Leu Ala Gly Thr Ile Trp Lys Val Leu Ala Ser
1               5                   10                  15
```

Glu Gly Gln Thr Val Ala Ala Gly Glu Val Leu Leu Ile Leu Glu Ala
            20                  25                  30

Met Lys Met Glu Thr Glu Ile Arg Ala Ala Gln Ala Gly Thr Val Arg
            35                  40                  45

Gly Ile Ala Val Lys Ala Gly Asp Ala Val Ala Val Gly Glu Thr Leu
            50                  55                  60

Met Thr Leu
65

<210> SEQ ID NO 6
<211> LENGTH: 68
<212> TYPE: PRT
<213> ORGANISM: Artificial
<220> FEATURE:
<223> OTHER INFORMATION: Synthetic peptide

<400> SEQUENCE: 6

Met Val Thr Ala Pro Leu Ala Gly Thr Ile Trp Lys Val Leu Ala Ser
1               5                   10                  15

Glu Gly Gln Thr Val Ala Ala Gly Glu Val Leu Leu Ile Leu Glu Ala
            20                  25                  30

Met Lys Met Glu Thr Glu Ile Arg Ala Ala Gln Ala Gly Thr Val Arg
            35                  40                  45

Gly Ile Ala Val Lys Ala Gly Asp Ala Val Ala Val Gly Glu Thr Leu
            50                  55                  60

Met Thr Leu Val
65

<210> SEQ ID NO 7
<211> LENGTH: 69
<212> TYPE: PRT
<213> ORGANISM: Artificial
<220> FEATURE:
<223> OTHER INFORMATION: Synthetic peptide

<400> SEQUENCE: 7

Met Val Thr Ala Pro Leu Ala Gly Thr Ile Trp Lys Val Leu Ala Ser
1               5                   10                  15

Glu Gly Gln Thr Val Ala Ala Gly Glu Val Leu Leu Ile Leu Glu Ala
            20                  25                  30

Met Lys Met Glu Thr Glu Ile Arg Ala Ala Gln Ala Gly Thr Val Arg
            35                  40                  45

Gly Ile Ala Val Lys Ala Gly Asp Ala Val Ala Val Gly Glu Thr Leu
            50                  55                  60

Met Thr Leu Val Asp
65

<210> SEQ ID NO 8
<211> LENGTH: 70
<212> TYPE: PRT
<213> ORGANISM: Artificial
<220> FEATURE:
<223> OTHER INFORMATION: Synthetic peptide

<400> SEQUENCE: 8

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
            20                  25                  30

```
Leu Glu Ala Met Lys Met Glu Thr Glu Ile Arg Ala Ala Gln Ala Gly
             35                  40                  45

Thr Val Arg Gly Ile Ala Val Lys Ala Gly Asp Ala Val Ala Val Gly
         50                  55                  60

Glu Thr Leu Met Thr Leu
 65                  70

<210> SEQ ID NO 9
<211> LENGTH: 71
<212> TYPE: PRT
<213> ORGANISM: Artificial
<220> FEATURE:
<223> OTHER INFORMATION: Synthetic peptide

<400> SEQUENCE: 9

Met Val Gly Ala Val Thr Ala Pro Leu Ala Gly Thr Ile Trp Lys Val
  1               5                  10                  15

Leu Ala Ser Glu Gly Gln Thr Val Ala Ala Gly Glu Val Leu Leu Ile
             20                  25                  30

Leu Glu Ala Met Lys Met Glu Thr Glu Ile Arg Ala Ala Gln Ala Gly
             35                  40                  45

Thr Val Arg Gly Ile Ala Val Lys Ala Gly Asp Ala Val Ala Val Gly
         50                  55                  60

Glu Thr Leu Met Thr Leu Val
 65                  70

<210> SEQ ID NO 10
<211> LENGTH: 72
<212> TYPE: PRT
<213> ORGANISM: Artificial
<220> FEATURE:
<223> OTHER INFORMATION: Synthetic peptide

<400> SEQUENCE: 10

Met Val Gly Ala Val Thr Ala Pro Leu Ala Gly Thr Ile Trp Lys Val
  1               5                  10                  15

Leu Ala Ser Glu Gly Gln Thr Val Ala Ala Gly Glu Val Leu Leu Ile
             20                  25                  30

Leu Glu Ala Met Lys Met Glu Thr Glu Ile Arg Ala Ala Gln Ala Gly
             35                  40                  45

Thr Val Arg Gly Ile Ala Val Lys Ala Gly Asp Ala Val Ala Val Gly
         50                  55                  60

Glu Thr Leu Met Thr Leu Val Asp
 65                  70

<210> SEQ ID NO 11
<211> LENGTH: 67
<212> TYPE: PRT
<213> ORGANISM: Artificial
<220> FEATURE:
<223> OTHER INFORMATION: Synthetic peptide

<400> SEQUENCE: 11

Val Thr Ala Pro Leu Ala Gly Thr Ile Trp Lys Val Leu Ala Ser Glu
  1               5                  10                  15

Gly Gln Thr Val Ala Ala Gly Glu Val Leu Leu Ile Leu Glu Ala Met
             20                  25                  30

Lys Met Glu Thr Glu Ile Arg Ala Ala Gln Ala Gly Thr Val Arg Gly
             35                  40                  45

Ile Ala Val Lys Ala Gly Asp Ala Val Ala Val Gly Asp Thr Leu Met
```

```
            50                  55                  60

Thr Leu Val
 65

<210> SEQ ID NO 12
<211> LENGTH: 68
<212> TYPE: PRT
<213> ORGANISM: Artificial
<220> FEATURE:
<223> OTHER INFORMATION: Synthetic peptide

<400> SEQUENCE: 12

Val Thr Ala Pro Leu Ala Gly Thr Ile Trp Lys Val Leu Ala Ser Glu
  1               5                  10                  15

Gly Gln Thr Val Ala Ala Gly Glu Val Leu Leu Ile Leu Glu Ala Met
             20                  25                  30

Lys Met Glu Thr Glu Ile Arg Ala Ala Gln Ala Gly Thr Val Arg Gly
         35                  40                  45

Ile Ala Val Lys Ala Gly Asp Ala Val Ala Val Gly Asp Thr Leu Met
     50                  55                  60

Thr Leu Val Asp
 65

<210> SEQ ID NO 13
<211> LENGTH: 67
<212> TYPE: PRT
<213> ORGANISM: Artificial
<220> FEATURE:
<223> OTHER INFORMATION: Synthetic peptide

<400> SEQUENCE: 13

Met Val Thr Ala Pro Leu Ala Gly Thr Ile Trp Lys Val Leu Ala Ser
  1               5                  10                  15

Glu Gly Gln Thr Val Ala Ala Gly Glu Val Leu Leu Ile Leu Glu Ala
             20                  25                  30

Met Lys Met Glu Thr Glu Ile Arg Ala Ala Gln Ala Gly Thr Val Arg
         35                  40                  45

Gly Ile Ala Val Lys Ala Gly Asp Ala Val Ala Val Gly Asp Thr Leu
     50                  55                  60

Met Thr Leu
 65

<210> SEQ ID NO 14
<211> LENGTH: 68
<212> TYPE: PRT
<213> ORGANISM: Artificial
<220> FEATURE:
<223> OTHER INFORMATION: Synthetic peptide

<400> SEQUENCE: 14

Met Val Thr Ala Pro Leu Ala Gly Thr Ile Trp Lys Val Leu Ala Ser
  1               5                  10                  15

Glu Gly Gln Thr Val Ala Ala Gly Glu Val Leu Leu Ile Leu Glu Ala
             20                  25                  30

Met Lys Met Glu Thr Glu Ile Arg Ala Ala Gln Ala Gly Thr Val Arg
         35                  40                  45

Gly Ile Ala Val Lys Ala Gly Asp Ala Val Ala Val Gly Asp Thr Leu
     50                  55                  60

Met Thr Leu Val
 65
```

<210> SEQ ID NO 15
<211> LENGTH: 69
<212> TYPE: PRT
<213> ORGANISM: Artificial
<220> FEATURE:
<223> OTHER INFORMATION: Synthetic peptide

<400> SEQUENCE: 15

Met Val Thr Ala Pro Leu Ala Gly Thr Ile Trp Lys Val Leu Ala Ser
1               5                   10                  15
Glu Gly Gln Thr Val Ala Ala Gly Glu Val Leu Leu Ile Leu Glu Ala
            20                  25                  30
Met Lys Met Glu Thr Glu Ile Arg Ala Ala Gln Ala Gly Thr Val Arg
        35                  40                  45
Gly Ile Ala Val Lys Ala Gly Asp Ala Val Ala Val Gly Asp Thr Leu
    50                  55                  60
Met Thr Leu Val Asp
65

<210> SEQ ID NO 16
<211> LENGTH: 70
<212> TYPE: PRT
<213> ORGANISM: Artificial
<220> FEATURE:
<223> OTHER INFORMATION: Synthetic peptide

<400> SEQUENCE: 16

Met Val Gly Ala Val Thr Ala Pro Leu Ala Gly Thr Ile Trp Lys Val
1               5                   10                  15
Leu Ala Ser Glu Gly Gln Thr Val Ala Ala Gly Glu Val Leu Leu Ile
            20                  25                  30
Leu Glu Ala Met Lys Met Glu Thr Glu Ile Arg Ala Ala Gln Ala Gly
        35                  40                  45
Thr Val Arg Gly Ile Ala Val Lys Ala Gly Asp Ala Val Ala Val Gly
    50                  55                  60
Asp Thr Leu Met Thr Leu
65                  70

<210> SEQ ID NO 17
<211> LENGTH: 70
<212> TYPE: PRT
<213> ORGANISM: Artificial
<220> FEATURE:
<223> OTHER INFORMATION: Synthetic peptide

<400> SEQUENCE: 17

Met Val Gly Ala Val Thr Ala Pro Leu Ala Gly Thr Ile Trp Lys Val
1               5                   10                  15
Leu Ala Ser Glu Gly Gln Thr Val Ala Ala Gly Glu Val Leu Leu Ile
            20                  25                  30
Leu Glu Ala Met Lys Met Glu Thr Glu Ile Arg Ala Ala Gln Ala Gly
        35                  40                  45
Thr Val Arg Gly Ile Ala Val Lys Ala Gly Asp Ala Val Ala Val Gly
    50                  55                  60
Asp Thr Leu Met Thr Leu
65                  70

<210> SEQ ID NO 18
<211> LENGTH: 70

```
<212> TYPE: PRT
<213> ORGANISM: Artificial
<220> FEATURE:
<223> OTHER INFORMATION: Synthetic peptide

<400> SEQUENCE: 18

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
            20                  25                  30

Leu Glu Ala Met Lys Met Glu Thr Glu Ile Arg Ala Ala Gln Ala Gly
        35                  40                  45

Thr Val Arg Gly Ile Ala Val Lys Ala Gly Asp Ala Val Ala Val Gly
    50                  55                  60

Asp Thr Leu Met Thr Leu
65                  70

<210> SEQ ID NO 19
<211> LENGTH: 102
<212> TYPE: PRT
<213> ORGANISM: Phage TP21

<400> SEQUENCE: 19

Pro Pro Thr Pro Ile Pro Gln Pro Glu Pro Gln Leu Pro Ser Gly Gln
1               5                   10                  15

Tyr Asp Ser Ser Trp Phe Thr Lys Glu Ser Gly Thr Phe Thr Leu Asn
            20                  25                  30

Thr Thr Ile Asn Leu Arg Thr Ala Pro Phe Ser Asn Ala Pro Leu Ile
        35                  40                  45

Ala Thr Leu Ser Lys Gly Gln Gln Val Ser Tyr Asp Gly Tyr Gly Ile
    50                  55                  60

Glu Leu Asp Gly His Val Trp Ile Arg Gln Pro Arg Ala Asn Gly Thr
65                  70                  75                  80

Tyr Gly Tyr Met Ala Thr Gly Glu Ser Ala Asn Gly Lys Arg Val Asp
                85                  90                  95

Tyr Trp Gly Ser Phe Lys
            100

<210> SEQ ID NO 20
<211> LENGTH: 160
<212> TYPE: PRT
<213> ORGANISM: Phage Bastille

<400> SEQUENCE: 20

Glu Lys Glu Gly Ala Lys Glu Thr Leu Val Pro Ala Leu Asn Lys Val
1               5                   10                  15

Val Thr Tyr Glu Val Gly Thr Asn Leu Ile Pro Glu Ile Gln Asp Lys
            20                  25                  30

Leu Ala Phe Leu Gly Tyr Glu Ala Arg Ile Asn Phe Thr Gly Leu Gly
        35                  40                  45

Asp Gly Leu Val Ser Ile Glu Thr Ser His Gln Val Gly Ala Glu Leu
    50                  55                  60

Asp Lys Leu Thr Ala Trp Leu Asp Glu Arg Gly Trp Ala Tyr Tyr Tyr
65                  70                  75                  80

Thr Ser Ser Lys Glu Gly Tyr Asn Gly Lys Ser Lys Val Val Thr Tyr
                85                  90                  95

Asp Met Gly Thr Asn Lys Ile Pro Glu Leu Ser Asn Val Leu Ala Tyr
            100                 105                 110
```

-continued

Gln Gly Met Gln Thr Ala Ile Val Phe Thr Gly Lys Gly Asp Gly Leu
            115                 120                 125

Ile Arg Leu Glu Ser Thr Pro Leu Asp Glu Ser Arg Leu Gln Asn Phe
130                 135                 140

Lys Asn Ile Leu Glu Ala Gln Lys Ile Ala Tyr Tyr Met Tyr Ser Glu
145                 150                 155                 160

<210> SEQ ID NO 21
<211> LENGTH: 101
<212> TYPE: PRT
<213> ORGANISM: Staphylococcus aureus subsp. aureus USA300

<400> SEQUENCE: 21

Met Pro Pro Val Pro Ala Gly Tyr Thr Leu Asp Lys Asn Asn Val Pro
1               5                   10                  15

Tyr Lys Lys Glu Gln Gly Asn Tyr Thr Val Ala Asn Val Lys Gly Asn
                20                  25                  30

Asn Val Arg Asp Gly Tyr Ser Thr Asn Ser Arg Ile Thr Gly Val Leu
            35                  40                  45

Pro Asn Asn Thr Thr Ile Thr Tyr Asp Gly Ala Tyr Cys Ile Asn Gly
        50                  55                  60

Tyr Arg Trp Ile Thr Tyr Ile Ala Asn Ser Gly Gln Arg Arg Tyr Ile
65                  70                  75                  80

Ala Thr Gly Glu Val Asp Ile Ala Gly Asn Arg Ile Ser Ser Phe Gly
                85                  90                  95

Lys Phe Ser Ala Val
            100

<210> SEQ ID NO 22
<211> LENGTH: 226
<212> TYPE: PRT
<213> ORGANISM: Phage A511

<400> SEQUENCE: 22

Lys Ala Gly Ile Pro Ile Thr Leu Asp Ser Gly Ser Lys Thr Ser Asp
1               5                   10                  15

Lys Gly Ile Lys Ser His Lys Trp Val Ala Asp Lys Leu Gly Gly Thr
                20                  25                  30

Thr His Gln Asp Pro Tyr Ala Tyr Leu Ser Ser Trp Gly Ile Ser Lys
            35                  40                  45

Ala Gln Phe Ala Ser Asp Leu Ala Lys Val Ser Gly Gly Gly Asn Thr
        50                  55                  60

Gly Thr Ala Pro Ala Lys Pro Ser Thr Pro Ala Pro Lys Pro Ser Thr
65                  70                  75                  80

Pro Ser Thr Asn Leu Asp Lys Leu Gly Leu Val Asp Tyr Met Asn Ala
                85                  90                  95

Lys Lys Met Asp Ser Ser Tyr Ser Asn Arg Asp Lys Leu Ala Lys Gln
            100                 105                 110

Tyr Gly Ile Ala Asn Tyr Ser Gly Thr Ala Ser Gln Asn Thr Thr Leu
        115                 120                 125

Leu Ser Lys Ile Lys Gly Gly Ala Pro Lys Pro Ser Thr Pro Ala Pro
130                 135                 140

Lys Pro Ser Thr Ser Thr Ala Lys Lys Ile Tyr Phe Pro Pro Asn Lys
145                 150                 155                 160

Gly Asn Trp Ser Val Tyr Pro Thr Asn Lys Ala Pro Val Lys Ala Asn
                165                 170                 175

```
Ala Ile Gly Ala Ile Asn Pro Thr Lys Phe Gly Gly Leu Thr Tyr Thr
            180                 185                 190

Ile Gln Lys Asp Arg Gly Asn Gly Val Tyr Glu Ile Gln Thr Asp Gln
        195                 200                 205

Phe Gly Arg Val Gln Val Tyr Gly Ala Pro Ser Thr Gly Ala Val Ile
    210                 215                 220

Lys Lys
225

<210> SEQ ID NO 23
<211> LENGTH: 197
<212> TYPE: PRT
<213> ORGANISM: Phage A511

<400> SEQUENCE: 23

Gly Gly Thr Thr His Gln Asp Pro Tyr Ala Tyr Leu Ser Ser Trp Gly
1               5                   10                  15

Ile Ser Lys Ala Gln Phe Ala Ser Asp Leu Ala Lys Val Ser Gly Gly
            20                  25                  30

Gly Asn Thr Gly Thr Ala Pro Ala Lys Pro Ser Thr Pro Ala Pro Lys
        35                  40                  45

Pro Ser Thr Pro Ser Thr Asn Leu Asp Lys Leu Gly Leu Val Asp Tyr
    50                  55                  60

Met Asn Ala Lys Lys Met Asp Ser Ser Tyr Ser Asn Arg Asp Lys Leu
65                  70                  75                  80

Ala Lys Gln Tyr Gly Ile Ala Asn Tyr Ser Gly Thr Ala Ser Gln Asn
                85                  90                  95

Thr Thr Leu Leu Ser Lys Ile Lys Gly Gly Ala Pro Lys Pro Ser Thr
            100                 105                 110

Pro Ala Pro Lys Pro Ser Thr Ser Thr Ala Lys Lys Ile Tyr Phe Pro
        115                 120                 125

Pro Asn Lys Gly Asn Trp Ser Val Tyr Pro Thr Asn Lys Ala Pro Val
    130                 135                 140

Lys Ala Asn Ala Ile Gly Ala Ile Asn Pro Thr Lys Phe Gly Gly Leu
145                 150                 155                 160

Thr Tyr Thr Ile Gln Lys Asp Arg Gly Asn Gly Val Tyr Glu Ile Gln
                165                 170                 175

Thr Asp Gln Phe Gly Arg Val Gln Val Tyr Gly Ala Pro Ser Thr Gly
            180                 185                 190

Ala Val Ile Lys Lys
        195

<210> SEQ ID NO 24
<211> LENGTH: 175
<212> TYPE: PRT
<213> ORGANISM: Phage A511

<400> SEQUENCE: 24

Ala Ser Asp Leu Ala Lys Val Ser Gly Gly Gly Asn Thr Gly Thr Ala
1               5                   10                  15

Pro Ala Lys Pro Ser Thr Pro Ala Pro Lys Pro Ser Thr Pro Ser Thr
            20                  25                  30

Asn Leu Asp Lys Leu Gly Leu Val Asp Tyr Met Asn Ala Lys Lys Met
        35                  40                  45

Asp Ser Ser Tyr Ser Asn Arg Asp Lys Leu Ala Lys Gln Tyr Gly Ile
    50                  55                  60
```

```
Ala Asn Tyr Ser Gly Thr Ala Ser Gln Asn Thr Thr Leu Leu Ser Lys
 65                  70                  75                  80

Ile Lys Gly Gly Ala Pro Lys Pro Ser Thr Pro Ala Pro Lys Pro Ser
             85                  90                  95

Thr Ser Thr Ala Lys Lys Ile Tyr Phe Pro Pro Asn Lys Gly Asn Trp
            100                 105                 110

Ser Val Tyr Pro Thr Asn Lys Ala Pro Val Lys Ala Asn Ala Ile Gly
        115                 120                 125

Ala Ile Asn Pro Thr Lys Phe Gly Gly Leu Thr Tyr Thr Ile Gln Lys
130                 135                 140

Asp Arg Gly Asn Gly Val Tyr Glu Ile Gln Thr Asp Gln Phe Gly Arg
145                 150                 155                 160

Val Gln Val Tyr Gly Ala Pro Ser Thr Gly Ala Val Ile Lys Lys
                165                 170                 175

<210> SEQ ID NO 25
<211> LENGTH: 158
<212> TYPE: PRT
<213> ORGANISM: Phage phi3626

<400> SEQUENCE: 25

Glu Tyr Glu Val Gln Glu Ser Lys Pro Val Pro Val Tyr Asp Arg Asn
1               5                   10                  15

Lys Phe Lys Thr Asn Ala Arg Ala Leu Val Asn Leu Asp Pro Arg Asp
            20                  25                  30

Arg Ala Ser Gly Ile Tyr Glu Asp Leu Gly Glu Ile Tyr Lys Asp Glu
        35                  40                  45

Arg Phe Tyr Val Leu Pro Glu Val Cys Asp Lys Gly Asp Tyr Leu Pro
    50                  55                  60

Val Leu Tyr Trp Lys Asp Gly Ala Asn Arg Ala Ser Asn Lys Val Trp
65                  70                  75                  80

Val Ser Ser Lys Gln Lys Tyr Met Met Ile Asp Thr Tyr His Arg Val
                85                  90                  95

Val Asn Val Val Thr Glu Leu Asp Ala Arg Tyr Glu Pro Ser Pro Asn
            100                 105                 110

Ser Asn Arg Met Gly Tyr Val Cys Asn Ala Glu Arg Val Tyr Val His
        115                 120                 125

Lys Ile Glu Gly Asn Tyr Ala Leu Cys Thr Tyr Phe Ala Gly Glu Gly
    130                 135                 140

Tyr Lys Thr Ala Trp Phe Thr Ala Lys Tyr Leu Glu Arg Ile
145                 150                 155

<210> SEQ ID NO 26
<211> LENGTH: 170
<212> TYPE: PRT
<213> ORGANISM: bacteriophage phi3626

<400> SEQUENCE: 26

Gly Gly Gln Ala Pro Gly Thr Val Ile Glu Asn Val Glu Tyr Glu Val
1               5                   10                  15

Gln Glu Ser Lys Pro Val Pro Val Tyr Asp Arg Asn Lys Phe Lys Thr
            20                  25                  30

Asn Ala Arg Ala Leu Val Asn Leu Asp Pro Arg Asp Arg Ala Ser Gly
        35                  40                  45

Ile Tyr Glu Asp Leu Gly Glu Ile Tyr Lys Asp Glu Arg Phe Tyr Val
    50                  55                  60
```

```
Leu Pro Glu Val Cys Asp Lys Gly Asp Tyr Leu Pro Val Leu Tyr Trp
 65                  70                  75                  80

Lys Asp Gly Ala Asn Arg Ala Ser Asn Lys Val Trp Val Ser Ser Lys
                 85                  90                  95

Gln Lys Tyr Met Met Ile Asp Thr Tyr His Arg Val Val Asn Val Val
            100                 105                 110

Thr Glu Leu Asp Ala Arg Tyr Glu Pro Ser Pro Asn Ser Asn Arg Met
        115                 120                 125

Gly Tyr Val Cys Asn Ala Glu Arg Val Tyr Val His Lys Ile Glu Gly
130                 135                 140

Asn Tyr Ala Leu Cys Thr Tyr Phe Ala Gly Gly Tyr Lys Thr Ala
145                 150                 155                 160

Trp Phe Thr Ala Lys Tyr Leu Glu Arg Ile
                165                 170

<210> SEQ ID NO 27
<211> LENGTH: 96
<212> TYPE: PRT
<213> ORGANISM: Phage of Staphylococcus epidermis
<220> FEATURE:
<221> NAME/KEY: misc_feature
<222> LOCATION: (83)..(83)
<223> OTHER INFORMATION: Xaa can be any naturally occurring amino acid

<400> SEQUENCE: 27

Met Lys Arg Lys Lys Pro Lys Gly Trp Ser Glu Asn Pro Tyr Gly Thr
 1               5                  10                  15

Tyr Tyr Lys Lys Val Asp Lys Thr Phe Ile Val Gly Ser Glu Lys Ile
            20                  25                  30

Glu Thr Arg Ile Gly Ser Pro Phe Leu Ser Ala Pro Ser Gly Gly His
        35                  40                  45

Val Thr Pro Asn Gln Lys Met Thr Phe Asp Tyr Leu Ala Gln Gln Asp
    50                  55                  60

Gly Tyr Glu Trp Gly Gln Leu Glu Asn Asn Arg Gly Gln Gln Glu Phe
65                  70                  75                  80

Val Pro Xaa Arg Pro Leu Ser Gln Lys Glu Tyr Trp Gly Ile Leu Lys
                85                  90                  95

<210> SEQ ID NO 28
<211> LENGTH: 105
<212> TYPE: PRT
<213> ORGANISM: Phage of Staphylococcus aureus

<400> SEQUENCE: 28

Met Asn Thr Val Lys Pro Val Val Ser Ala Trp Lys Arg Asn Lys Tyr
 1               5                  10                  15

Gly Thr Tyr Tyr Met Glu Glu Ser Ala Arg Phe Thr Asn Gly Asn Gln
            20                  25                  30

Pro Ile Thr Val Arg Lys Ile Gly Pro Phe Leu Ser Cys Pro Val Ala
        35                  40                  45

Tyr Gln Phe Gln Pro Gly Gly Tyr Cys Asp Tyr Thr Glu Val Met Leu
    50                  55                  60

Gln Asp Gly His Val Trp Val Gly Tyr Thr Trp Glu Gly Gln Arg Tyr
65                  70                  75                  80

Tyr Leu Pro Ile Arg Thr Trp Asn Gly Ser Ala Pro Pro Asn Gln Ile
                85                  90                  95

Leu Gly Asp Leu Trp Gly Glu Ile Ser
```

<210> SEQ ID NO 29
<211> LENGTH: 124
<212> TYPE: PRT
<213> ORGANISM: Staphylococcus simulans

<400> SEQUENCE: 29

Met Ser Asn Ser Thr Ala Gln Asp Pro Met Pro Phe Leu Lys Ser Ala
1               5                   10                  15

Gly Tyr Gly Lys Ala Gly Gly Thr Val Thr Pro Thr Pro Asn Thr Gly
            20                  25                  30

Trp Lys Thr Asn Lys Tyr Gly Thr Leu Tyr Lys Ser Glu Ser Ala Ser
        35                  40                  45

Phe Thr Pro Asn Thr Asp Ile Ile Thr Arg Thr Thr Gly Pro Phe Arg
    50                  55                  60

Ser Met Pro Gln Ser Gly Val Leu Lys Ala Gly Gln Thr Ile His Tyr
65                  70                  75                  80

Asp Glu Val Met Lys Gln Asp Gly His Val Trp Val Gly Tyr Thr Gly
                85                  90                  95

Asn Ser Gly Gln Arg Ile Tyr Leu Pro Val Arg Thr Trp Asn Lys Ser
            100                 105                 110

Thr Asn Thr Leu Gly Val Leu Trp Gly Thr Ile Lys
        115                 120

<210> SEQ ID NO 30
<211> LENGTH: 125
<212> TYPE: PRT
<213> ORGANISM: Phage of Stapholcoccus capitis

<400> SEQUENCE: 30

Met Asn Ser Phe Ser Asn Asn Thr Ala Gln Asp Pro Met Pro Phe Leu
1               5                   10                  15

Lys Ser Ala Gly Tyr Gly Ser Asn Ser Thr Ser Ser Ser Asn Asn Asn
            20                  25                  30

Gly Tyr Lys Thr Asn Lys Tyr Gly Thr Leu Tyr Lys Ser Glu Ser Ala
        35                  40                  45

Ser Phe Thr Ala Asn Thr Asp Ile Ile Thr Arg Leu Thr Gly Pro Phe
    50                  55                  60

Arg Ser Met Pro Gln Ser Gly Val Leu Arg Lys Gly Leu Thr Ile Lys
65                  70                  75                  80

Tyr Asp Glu Val Met Lys Gln Asp Gly His Val Trp Val Gly Tyr Asn
                85                  90                  95

Thr Asn Ser Gly Lys Arg Val Tyr Leu Pro Val Arg Thr Trp Asn Glu
            100                 105                 110

Ser Thr Gly Glu Leu Gly Pro Leu Trp Gly Thr Ile Lys
        115                 120                 125

<210> SEQ ID NO 31
<211> LENGTH: 101
<212> TYPE: PRT
<213> ORGANISM: Prophage of Staphylococcus aureus

<400> SEQUENCE: 31

Met Pro Pro Val Pro Ala Gly Tyr Thr Leu Asp Lys Asn Asn Val Pro
1               5                   10                  15

Tyr Lys Lys Glu Ala Gly Asn Tyr Thr Val Ala Asn Val Lys Gly Asn
            20                  25                  30

Asn Val Arg Asp Gly Tyr Ser Thr Asn Ser Arg Ile Thr Gly Val Leu
            35                  40                  45

Pro Asn Asn Ala Thr Ile Lys Tyr Asp Gly Ala Tyr Cys Ile Asn Gly
 50                  55                  60

Tyr Arg Trp Ile Thr Tyr Ile Ala Asn Ser Gly Gln Arg Arg Tyr Ile
 65                  70                  75                  80

Ala Thr Gly Glu Val Asp Lys Ala Gly Asn Arg Ile Ser Ser Phe Gly
            85                  90                  95

Lys Phe Ser Ala Val
           100

<210> SEQ ID NO 32
<211> LENGTH: 190
<212> TYPE: PRT
<213> ORGANISM: Prophage of Enterococcus faecalis

<400> SEQUENCE: 32

Thr Asn Lys Pro Glu Thr Asp Pro Ala Thr Asp Ala Gly Glu Glu
 1               5                  10                  15

Ile Glu Lys Ile Pro Asn Ser Asp Val Lys Val Gly Asp Thr Val Lys
            20                  25                  30

Val Lys Phe Asn Val Asp Ala Trp Ala Thr Gly Glu Ala Ile Pro Gln
            35                  40                  45

Trp Val Lys Gly Asn Ser Tyr Lys Val Gln Glu Val Thr Gly Ser Arg
 50                  55                  60

Val Leu Leu Glu Gly Ile Leu Ser Trp Ile Ser Lys Gly Asp Ile Glu
 65                  70                  75                  80

Leu Leu Pro Asp Ala Thr Val Val Pro Asp Lys Gln Pro Glu Ala Thr
            85                  90                  95

His Val Val Gln Tyr Gly Glu Thr Leu Ser Ser Ile Ala Tyr Gln Tyr
            100                 105                 110

Gly Thr Asp Tyr Gln Thr Leu Ala Ala Leu Asn Gly Leu Ala Asn Pro
            115                 120                 125

Asn Leu Ile Tyr Pro Gly Gln Val Leu Lys Val Asn Gly Ser Ala Thr
 130                 135                 140

Ser Asn Val Tyr Thr Val Lys Tyr Gly Asp Asn Leu Ser Ser Ile Ala
145                 150                 155                 160

Ala Lys Leu Gly Thr Thr Tyr Gln Ala Leu Ala Ala Leu Asn Gly Leu
            165                 170                 175

Ala Asn Pro Asn Leu Ile Tyr Pro Gly Gln Thr Leu Asn Tyr
 180                 185                 190

<210> SEQ ID NO 33
<211> LENGTH: 154
<212> TYPE: PRT
<213> ORGANISM: Prophage of Enterococcus faecalis

<400> SEQUENCE: 33

Ala Pro Lys Tyr Gln Val Gly Gln Ala Ile Arg Phe Thr Ser Ile Tyr
 1               5                  10                  15

Pro Thr Pro Asp Ala Leu Ile Asn Glu His Leu Ser Ala Glu Ala Leu
            20                  25                  30

Trp Thr Gln Val Gly Thr Ile Thr Ala Lys Leu Pro Asp Arg Gln Asn
            35                  40                  45

Leu Tyr Arg Val Glu Asn Ser Gly His Leu Leu Gly Tyr Val Asn Asp
 50                  55                  60

Gly Asp Ile Ala Glu Leu Trp Arg Pro Gln Thr Lys Lys Ser Phe Leu
 65                  70                  75                  80

Ile Gly Val Asp Glu Gly Ile Val Leu Arg Ala Gly Gln Pro Ser Leu
                 85                  90                  95

Leu Ala Pro Ile Tyr Gly Ile Trp Pro Lys Asn Thr Arg Phe Tyr Tyr
            100                 105                 110

Asp Thr Phe Tyr Ile Ala Asp Gly Tyr Val Phe Ile Gly Gly Thr Asp
        115                 120                 125

Thr Thr Gly Ala Arg Ile Tyr Leu Pro Ile Gly Pro Asn Asp Gly Asn
    130                 135                 140

Ala Gln Asn Thr Trp Gly Ser Phe Ala Ser
145                 150

<210> SEQ ID NO 34
<211> LENGTH: 9
<212> TYPE: PRT
<213> ORGANISM: Artificial
<220> FEATURE:
<223> OTHER INFORMATION: Synthetic peptide

<400> SEQUENCE: 34

Ala Gly Ala Gly Ala Gly Ala Gly Ser
1               5

<210> SEQ ID NO 35
<211> LENGTH: 11
<212> TYPE: PRT
<213> ORGANISM: Artificial
<220> FEATURE:
<223> OTHER INFORMATION: Synthetic peptide

<400> SEQUENCE: 35

Ala Gly Ala Gly Ala Gly Ala Gly Ser Glu Leu
1               5                   10

<210> SEQ ID NO 36
<211> LENGTH: 14
<212> TYPE: PRT
<213> ORGANISM: Artificial
<220> FEATURE:
<223> OTHER INFORMATION: Synthetic peptider

<400> SEQUENCE: 36

Thr Pro Thr Pro Pro Asn Pro Gly Pro Lys Asn Phe Thr Thr
1               5                   10

<210> SEQ ID NO 37
<211> LENGTH: 6
<212> TYPE: PRT
<213> ORGANISM: Artificial
<220> FEATURE:
<223> OTHER INFORMATION: Synthetic peptide

<400> SEQUENCE: 37

Ala Ala Lys Asn Pro Asn
1               5

<210> SEQ ID NO 38
<211> LENGTH: 9
<212> TYPE: PRT
<213> ORGANISM: Artificial
<220> FEATURE:
<223> OTHER INFORMATION: Synthetic peptide

<400> SEQUENCE: 38

Ala Gly Ala Gly Ala Gly Ala Glu Leu
1               5

<210> SEQ ID NO 39
<211> LENGTH: 251
<212> TYPE: PRT
<213> ORGANISM: Artificial
<220> FEATURE:
<223> OTHER INFORMATION: Synthetic peptide

<400> SEQUENCE: 39

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
                20                  25                  30

Leu Glu Ala Met Lys Met Glu Thr Glu Ile Arg Ala Ala Gln Ala Gly
            35                  40                  45

Thr Val Arg Gly Ile Ala Val Lys Ala Gly Asp Ala Val Ala Val Gly
        50                  55                  60

Glu Thr Leu Met Thr Leu Ala Gly Ala Gly Ala Gly Ala Gly Ser Glu
65                  70                  75                  80

Leu Gly Gly Gln Ala Pro Gly Thr Val Ile Glu Asn Val Glu Tyr Glu
                85                  90                  95

Val Gln Glu Ser Lys Pro Val Pro Val Tyr Asp Arg Asn Lys Phe Lys
            100                 105                 110

Thr Asn Ala Arg Ala Leu Val Asn Leu Asp Pro Arg Asp Arg Ala Ser
        115                 120                 125

Gly Ile Tyr Glu Asp Leu Gly Glu Ile Tyr Lys Asp Glu Arg Phe Tyr
    130                 135                 140

Val Leu Pro Glu Val Cys Asp Lys Gly Asp Tyr Leu Pro Val Leu Tyr
145                 150                 155                 160

Trp Lys Asp Gly Ala Asn Arg Ala Ser Asn Lys Val Trp Val Ser Ser
                165                 170                 175

Lys Gln Lys Tyr Met Met Ile Asp Thr Tyr His Arg Val Val Asn Val
            180                 185                 190

Val Thr Glu Leu Asp Ala Arg Tyr Glu Pro Ser Pro Asn Ser Asn Arg
        195                 200                 205

Met Gly Tyr Val Cys Asn Ala Glu Arg Val Tyr Val His Lys Ile Glu
    210                 215                 220

Gly Asn Tyr Ala Leu Cys Thr Tyr Phe Ala Gly Glu Gly Tyr Lys Thr
225                 230                 235                 240

Ala Trp Phe Thr Ala Lys Tyr Leu Glu Arg Ile
                245                 250

<210> SEQ ID NO 40
<211> LENGTH: 477
<212> TYPE: PRT
<213> ORGANISM: Artificial
<220> FEATURE:
<223> OTHER INFORMATION: Synthetic peptide

<400> SEQUENCE: 40

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
                20                  25                  30

```
Leu Glu Ala Met Lys Met Glu Thr Glu Ile Arg Ala Ala Gln Ala Gly
             35                  40                  45

Thr Val Arg Gly Ile Ala Val Lys Ala Gly Asp Ala Val Ala Val Gly
 50                  55                  60

Glu Thr Leu Met Thr Leu Ala Gly Ala Gly Ala Gly Ser Thr
 65                  70                  75                  80

Ser Lys Gly Glu Glu Leu Phe Thr Gly Val Val Pro Ile Leu Val Glu
                 85                  90                  95

Leu Asp Gly Asp Val Asn Gly His Lys Phe Ser Val Ser Gly Glu Gly
                100                 105                 110

Glu Gly Asp Ala Thr Tyr Gly Lys Leu Thr Leu Lys Phe Ile Cys Thr
            115                 120                 125

Thr Gly Lys Leu Pro Val Pro Trp Pro Thr Leu Val Thr Thr Phe Ala
130                 135                 140

Tyr Gly Leu Gln Cys Phe Ala Arg Tyr Pro Asp His Met Lys Gln His
145                 150                 155                 160

Asp Phe Phe Lys Ser Ala Met Pro Glu Gly Tyr Val Gln Glu Arg Thr
                165                 170                 175

Ile Ser Phe Lys Asp Asp Gly Asn Tyr Lys Thr Arg Ala Glu Val Lys
            180                 185                 190

Phe Glu Gly Asp Thr Leu Val Asn Arg Ile Glu Leu Lys Gly Ile Asp
195                 200                 205

Phe Lys Glu Asp Gly Asn Ile Leu Gly His Lys Leu Glu Tyr Asn Tyr
        210                 215                 220

Asn Ser His Asn Val Tyr Ile Thr Ala Asp Lys Gln Lys Asn Gly Ile
225                 230                 235                 240

Lys Ala Asn Phe Lys Ile Arg His Asn Ile Glu Asp Gly Ser Val Gln
                245                 250                 255

Leu Ala Asp His Tyr Gln Gln Asn Thr Pro Ile Gly Asp Gly Pro Val
            260                 265                 270

Leu Leu Pro Asp Asn His Tyr Leu Ser Thr Gln Ser Ala Leu Ser Lys
275                 280                 285

Asp Pro Asn Glu Lys Arg Asp His Met Val Leu Leu Glu Phe Val Thr
290                 295                 300

Ala Ala Gly Ile Thr His Gly Met Asp Glu Leu Tyr Lys Glu Leu Glu
305                 310                 315                 320

Tyr Glu Val Gln Glu Ser Lys Pro Val Pro Val Tyr Asp Arg Asn Lys
                325                 330                 335

Phe Lys Thr Asn Ala Arg Ala Leu Val Asn Leu Asp Pro Arg Asp Arg
            340                 345                 350

Ala Ser Gly Ile Tyr Glu Asp Leu Gly Glu Ile Tyr Lys Asp Glu Arg
        355                 360                 365

Phe Tyr Val Leu Pro Glu Val Cys Asp Lys Gly Asp Tyr Leu Pro Val
370                 375                 380

Leu Tyr Trp Lys Asp Gly Ala Asn Arg Ala Ser Asn Lys Val Trp Val
385                 390                 395                 400

Ser Ser Lys Gln Lys Tyr Met Met Ile Asp Thr Tyr His Arg Val Val
                405                 410                 415

Asn Val Val Thr Glu Leu Asp Ala Arg Tyr Glu Pro Ser Pro Asn Ser
            420                 425                 430

Asn Arg Met Gly Tyr Val Cys Asn Ala Glu Arg Val Tyr Val His Lys
        435                 440                 445

Ile Glu Gly Asn Tyr Ala Leu Cys Thr Tyr Phe Ala Gly Glu Gly Tyr
```

```
              450                 455                 460
Lys Thr Ala Trp Phe Thr Ala Lys Tyr Leu Glu Arg Ile
465                 470                 475

<210> SEQ ID NO 41
<211> LENGTH: 239
<212> TYPE: PRT
<213> ORGANISM: Artificial
<220> FEATURE:
<223> OTHER INFORMATION: Synthetic peptide

<400> SEQUENCE: 41

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
                20                  25                  30

Leu Glu Ala Met Lys Met Glu Thr Glu Ile Arg Ala Ala Gln Ala Gly
            35                  40                  45

Thr Val Arg Gly Ile Ala Val Lys Ala Gly Asp Ala Val Ala Val Gly
        50                  55                  60

Glu Thr Leu Met Thr Leu Ala Gly Ala Gly Ala Gly Ala Gly Ser Glu
65                  70                  75                  80

Leu Glu Tyr Glu Val Gln Glu Ser Lys Pro Val Pro Val Tyr Asp Arg
                85                  90                  95

Asn Lys Phe Lys Thr Asn Ala Arg Ala Leu Val Asn Leu Asp Pro Arg
            100                 105                 110

Asp Arg Ala Ser Gly Ile Tyr Glu Asp Leu Gly Glu Ile Tyr Lys Asp
        115                 120                 125

Glu Arg Phe Tyr Val Leu Pro Glu Val Cys Asp Lys Gly Asp Tyr Leu
130                 135                 140

Pro Val Leu Tyr Trp Lys Asp Gly Ala Asn Arg Ala Ser Asn Lys Val
145                 150                 155                 160

Trp Val Ser Ser Lys Gln Lys Tyr Met Met Ile Asp Thr Tyr His Arg
                165                 170                 175

Val Val Asn Val Val Thr Glu Leu Asp Ala Arg Tyr Glu Pro Ser Pro
            180                 185                 190

Asn Ser Asn Arg Met Gly Tyr Val Cys Asn Ala Glu Arg Val Tyr Val
        195                 200                 205

His Lys Ile Glu Gly Asn Tyr Ala Leu Cys Thr Tyr Phe Ala Gly Glu
210                 215                 220

Gly Tyr Lys Thr Ala Trp Phe Thr Ala Lys Tyr Leu Glu Arg Ile
225                 230                 235

<210> SEQ ID NO 42
<211> LENGTH: 183
<212> TYPE: PRT
<213> ORGANISM: Artificial
<220> FEATURE:
<223> OTHER INFORMATION: Synthetic peptide

<400> SEQUENCE: 42

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
                20                  25                  30

Leu Glu Ala Met Lys Met Glu Thr Glu Ile Arg Ala Ala Gln Ala Gly
            35                  40                  45
```

```
Thr Val Arg Gly Ile Ala Val Lys Ala Gly Asp Ala Val Ala Val Gly
 50                  55                  60
Glu Thr Leu Met Thr Leu Ala Gly Ala Gly Ala Gly Ser Glu
 65                  70                  75                  80
Leu Pro Pro Thr Pro Ile Pro Gln Pro Glu Pro Gln Leu Pro Ser Gly
                     85                  90                  95
Gln Tyr Asp Ser Ser Trp Phe Thr Lys Glu Ser Gly Thr Phe Thr Leu
                100                 105                 110
Asn Thr Ile Asn Leu Arg Thr Ala Pro Phe Ser Asn Ala Pro Leu
                115                 120                 125
Ile Ala Thr Leu Ser Lys Gly Gln Gln Val Ser Tyr Asp Gly Tyr Gly
130                 135                 140
Ile Glu Leu Asp Gly His Val Trp Ile Arg Gln Pro Arg Ala Asn Gly
145                 150                 155                 160
Thr Tyr Gly Tyr Met Ala Thr Gly Glu Ser Ala Asn Gly Lys Arg Val
                    165                 170                 175
Asp Tyr Trp Gly Ser Phe Lys
                180
```

<210> SEQ ID NO 43
<211> LENGTH: 421
<212> TYPE: PRT
<213> ORGANISM: Artificial
<220> FEATURE:
<223> OTHER INFORMATION: Synthetic peptide

<400> SEQUENCE: 43

```
Met Val Gly Ala Val Thr Ala Pro Leu Ala Gly Thr Ile Trp Lys Val
 1               5                  10                  15
Leu Ala Ser Glu Gly Gln Thr Val Ala Ala Gly Glu Val Leu Leu Ile
                20                  25                  30
Leu Glu Ala Met Lys Met Glu Thr Glu Ile Arg Ala Ala Gln Ala Gly
                35                  40                  45
Thr Val Arg Gly Ile Ala Val Lys Ala Gly Asp Ala Val Ala Val Gly
 50                  55                  60
Glu Thr Leu Met Thr Leu Ala Gly Ala Gly Ala Gly Ser Thr
 65                  70                  75                  80
Ser Lys Gly Glu Glu Leu Phe Thr Gly Val Val Pro Ile Leu Val Glu
                85                  90                  95
Leu Asp Gly Asp Val Asn Gly His Lys Phe Ser Val Ser Gly Glu Gly
                100                 105                 110
Glu Gly Asp Ala Thr Tyr Gly Lys Leu Thr Leu Lys Phe Ile Cys Thr
                115                 120                 125
Thr Gly Lys Leu Pro Val Pro Trp Pro Thr Leu Val Thr Thr Phe Ala
130                 135                 140
Tyr Gly Leu Gln Cys Phe Ala Arg Tyr Pro Asp His Met Lys Gln His
145                 150                 155                 160
Asp Phe Phe Lys Ser Ala Met Pro Glu Gly Tyr Val Gln Glu Arg Thr
                    165                 170                 175
Ile Ser Phe Lys Asp Asp Gly Asn Tyr Lys Thr Arg Ala Glu Val Lys
                180                 185                 190
Phe Glu Gly Asp Thr Leu Val Asn Arg Ile Glu Leu Lys Gly Ile Asp
                195                 200                 205
Phe Lys Glu Asp Gly Asn Ile Leu Gly His Lys Leu Glu Tyr Asn Tyr
210                 215                 220
```

-continued

Asn Ser His Asn Val Tyr Ile Thr Ala Asp Lys Gln Lys Asn Gly Ile
225                 230                 235                 240

Lys Ala Asn Phe Lys Ile Arg His Asn Ile Glu Asp Gly Ser Val Gln
            245                 250                 255

Leu Ala Asp His Tyr Gln Gln Asn Thr Pro Ile Gly Asp Gly Pro Val
        260                 265                 270

Leu Leu Pro Asp Asn His Tyr Leu Ser Thr Gln Ser Ala Leu Ser Lys
    275                 280                 285

Asp Pro Asn Glu Lys Arg Asp His Met Val Leu Leu Glu Phe Val Thr
290                 295                 300

Ala Ala Gly Ile Thr His Gly Met Asp Glu Leu Tyr Lys Glu Leu Pro
305                 310                 315                 320

Pro Thr Pro Ile Pro Gln Pro Glu Pro Gln Leu Pro Ser Gly Gln Tyr
            325                 330                 335

Asp Ser Ser Trp Phe Thr Lys Glu Ser Gly Thr Phe Thr Leu Asn Thr
        340                 345                 350

Thr Ile Asn Leu Arg Thr Ala Pro Phe Ser Asn Ala Pro Leu Ile Ala
    355                 360                 365

Thr Leu Ser Lys Gly Gln Gln Val Ser Tyr Asp Gly Tyr Gly Ile Glu
370                 375                 380

Leu Asp Gly His Val Trp Ile Arg Gln Pro Arg Ala Asn Gly Thr Tyr
385                 390                 395                 400

Gly Tyr Met Ala Thr Gly Glu Ser Ala Asn Gly Lys Arg Val Asp Tyr
            405                 410                 415

Trp Gly Ser Phe Lys
            420

<210> SEQ ID NO 44
<211> LENGTH: 241
<212> TYPE: PRT
<213> ORGANISM: Artificial
<220> FEATURE:
<223> OTHER INFORMATION: Synthetic peptide

<400> SEQUENCE: 44

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
            20                  25                  30

Leu Glu Ala Met Lys Met Glu Thr Glu Ile Arg Ala Ala Gln Ala Gly
        35                  40                  45

Thr Val Arg Gly Ile Ala Val Lys Ala Gly Asp Ala Val Ala Val Gly
    50                  55                  60

Glu Thr Leu Met Thr Leu Ala Gly Ala Gly Ala Gly Ser Glu
65                  70                  75                  80

Leu Glu Lys Glu Gly Ala Lys Glu Thr Leu Val Pro Ala Leu Asn Lys
            85                  90                  95

Val Val Thr Tyr Glu Val Gly Thr Asn Leu Ile Pro Glu Ile Gln Asp
            100                 105                 110

Lys Leu Ala Phe Leu Gly Tyr Glu Ala Arg Ile Asn Phe Thr Gly Leu
        115                 120                 125

Gly Asp Gly Leu Val Ser Ile Glu Thr Ser His Gln Val Gly Ala Glu
    130                 135                 140

Leu Asp Lys Leu Thr Ala Trp Leu Asp Glu Arg Gly Trp Ala Tyr Tyr
145                 150                 155                 160

```
Tyr Thr Ser Ser Lys Glu Gly Tyr Asn Gly Lys Ser Lys Val Val Thr
            165                 170                 175

Tyr Asp Met Gly Thr Asn Lys Ile Pro Glu Leu Ser Asn Val Leu Ala
        180                 185                 190

Tyr Gln Gly Met Gln Thr Ala Ile Val Phe Thr Gly Lys Gly Asp Gly
    195                 200                 205

Leu Ile Arg Leu Glu Ser Thr Pro Leu Asp Glu Ser Arg Leu Gln Asn
210                 215                 220

Phe Lys Asn Ile Leu Glu Ala Gln Lys Ile Ala Tyr Tyr Met Tyr Ser
225                 230                 235                 240

Glu

<210> SEQ ID NO 45
<211> LENGTH: 479
<212> TYPE: PRT
<213> ORGANISM: Artificial
<220> FEATURE:
<223> OTHER INFORMATION: Synthetic peptide

<400> SEQUENCE: 45

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
            20                  25                  30

Leu Glu Ala Met Lys Met Glu Thr Glu Ile Arg Ala Ala Gln Ala Gly
        35                  40                  45

Thr Val Arg Gly Ile Ala Val Lys Ala Gly Asp Ala Val Ala Val Gly
    50                  55                  60

Glu Thr Leu Met Thr Leu Ala Gly Ala Gly Ala Gly Ala Gly Ser Thr
65                  70                  75                  80

Ser Lys Gly Glu Glu Leu Phe Thr Gly Val Val Pro Ile Leu Val Glu
            85                  90                  95

Leu Asp Gly Asp Val Asn Gly His Lys Phe Ser Val Ser Gly Glu Gly
        100                 105                 110

Glu Gly Asp Ala Thr Tyr Gly Lys Leu Thr Leu Lys Phe Ile Cys Thr
    115                 120                 125

Thr Gly Lys Leu Pro Val Pro Trp Pro Thr Leu Val Thr Thr Phe Ala
130                 135                 140

Tyr Gly Leu Gln Cys Phe Ala Arg Tyr Pro Asp His Met Lys Gln His
145                 150                 155                 160

Asp Phe Phe Lys Ser Ala Met Pro Glu Gly Tyr Val Gln Glu Arg Thr
            165                 170                 175

Ile Ser Phe Lys Asp Asp Gly Asn Tyr Lys Thr Arg Ala Glu Val Lys
        180                 185                 190

Phe Glu Gly Asp Thr Leu Val Asn Arg Ile Glu Leu Lys Gly Ile Asp
    195                 200                 205

Phe Lys Glu Asp Gly Asn Ile Leu Gly His Lys Leu Glu Tyr Asn Tyr
210                 215                 220

Asn Ser His Asn Val Tyr Ile Thr Ala Asp Lys Gln Lys Asn Gly Ile
225                 230                 235                 240

Lys Ala Asn Phe Lys Ile Arg His Asn Ile Glu Asp Gly Ser Val Gln
            245                 250                 255

Leu Ala Asp His Tyr Gln Gln Asn Thr Pro Ile Gly Asp Gly Pro Val
        260                 265                 270

Leu Leu Pro Asp Asn His Tyr Leu Ser Thr Gln Ser Ala Leu Ser Lys
```

```
                275                 280                 285
Asp Pro Asn Glu Lys Arg Asp His Met Val Leu Leu Glu Phe Val Thr
290                 295                 300

Ala Ala Gly Ile Thr His Gly Met Asp Glu Leu Tyr Lys Glu Leu Glu
305                 310                 315                 320

Lys Glu Gly Ala Lys Glu Thr Leu Val Pro Ala Leu Asn Lys Val Val
                325                 330                 335

Thr Tyr Glu Val Gly Thr Asn Leu Ile Pro Glu Ile Gln Asp Lys Leu
            340                 345                 350

Ala Phe Leu Gly Tyr Glu Ala Arg Ile Asn Phe Thr Gly Leu Gly Asp
                355                 360                 365

Gly Leu Val Ser Ile Glu Thr Ser His Gln Val Gly Ala Glu Leu Asp
        370                 375                 380

Lys Leu Thr Ala Trp Leu Asp Glu Arg Gly Trp Ala Tyr Tyr Tyr Thr
385                 390                 395                 400

Ser Ser Lys Glu Gly Tyr Asn Gly Lys Ser Lys Val Val Thr Tyr Asp
                405                 410                 415

Met Gly Thr Asn Lys Ile Pro Glu Leu Ser Asn Val Leu Ala Tyr Gln
            420                 425                 430

Gly Met Gln Thr Ala Ile Val Phe Thr Gly Lys Gly Asp Gly Leu Ile
        435                 440                 445

Arg Leu Glu Ser Thr Pro Leu Asp Glu Ser Arg Leu Gln Asn Phe Lys
450                 455                 460

Asn Ile Leu Glu Ala Gln Lys Ile Ala Tyr Tyr Met Tyr Ser Glu
465                 470                 475

<210> SEQ ID NO 46
<211> LENGTH: 182
<212> TYPE: PRT
<213> ORGANISM: Artificial
<220> FEATURE:
<223> OTHER INFORMATION: Synthetic peptide

<400> SEQUENCE: 46

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
                20                  25                  30

Leu Glu Ala Met Lys Met Glu Thr Glu Ile Arg Ala Ala Gln Ala Gly
            35                  40                  45

Thr Val Arg Gly Ile Ala Val Lys Ala Gly Asp Ala Val Ala Val Gly
        50                  55                  60

Glu Thr Leu Met Thr Leu Ala Gly Ala Gly Ala Gly Ala Gly Ser Glu
65                  70                  75                  80

Leu Met Pro Pro Val Pro Ala Gly Tyr Thr Leu Asp Lys Asn Asn Val
                85                  90                  95

Pro Tyr Lys Lys Glu Gln Gly Asn Tyr Thr Val Ala Asn Val Lys Gly
                100                 105                 110

Asn Asn Val Arg Asp Gly Tyr Ser Thr Asn Ser Arg Ile Thr Gly Val
            115                 120                 125

Leu Pro Asn Asn Thr Thr Ile Thr Tyr Asp Gly Ala Tyr Cys Ile Asn
        130                 135                 140

Gly Tyr Arg Trp Ile Thr Tyr Ile Ala Asn Ser Gly Gln Arg Arg Tyr
145                 150                 155                 160

Ile Ala Thr Gly Glu Val Asp Ile Ala Gly Asn Arg Ile Ser Ser Phe
```

Gly Lys Phe Ser Ala Val
            180

<210> SEQ ID NO 47
<211> LENGTH: 177
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (164)..(164)
<223> OTHER INFORMATION: Xaa can be any naturally occurring amino acid

<400> SEQUENCE: 47

Met Val Gly Ala Val Thr Ala Pro Leu Ala Gly Thr Ile Trp Lys Val
1               5                   10                  15

Leu Ala Ser Glu Gly Gln Thr Val Ala Gly Glu Val Leu Leu Ile
            20                  25                  30

Leu Glu Ala Met Lys Met Glu Thr Glu Ile Arg Ala Ala Gln Ala Gly
            35                  40                  45

Thr Val Arg Gly Ile Ala Val Lys Ala Gly Asp Ala Val Ala Val Gly
        50                  55                  60

Glu Thr Leu Met Thr Leu Ala Gly Ala Gly Ala Gly Ala Gly Ser Glu
65                  70                  75                  80

Leu Met Lys Arg Lys Lys Pro Lys Gly Trp Ser Glu Asn Pro Tyr Gly
                85                  90                  95

Thr Tyr Tyr Lys Lys Val Asp Lys Thr Phe Ile Val Gly Ser Glu Lys
            100                 105                 110

Ile Glu Thr Arg Ile Gly Ser Pro Phe Leu Ser Ala Pro Ser Gly Gly
            115                 120                 125

His Val Thr Pro Asn Gln Lys Met Thr Phe Asp Tyr Leu Ala Gln Gln
        130                 135                 140

Asp Gly Tyr Glu Trp Gly Gln Leu Glu Asn Asn Arg Gly Gln Gln Glu
145                 150                 155                 160

Phe Val Pro Xaa Arg Pro Leu Ser Gln Lys Glu Tyr Trp Gly Ile Leu
                165                 170                 175

Lys

<210> SEQ ID NO 48
<211> LENGTH: 186
<212> TYPE: PRT
<213> ORGANISM: Artificial
<220> FEATURE:
<223> OTHER INFORMATION: Synthetic peptide

<400> SEQUENCE: 48

Met Val Gly Ala Val Thr Ala Pro Leu Ala Gly Thr Ile Trp Lys Val
1               5                   10                  15

Leu Ala Ser Glu Gly Gln Thr Val Ala Gly Glu Val Leu Leu Ile
            20                  25                  30

Leu Glu Ala Met Lys Met Glu Thr Glu Ile Arg Ala Ala Gln Ala Gly
            35                  40                  45

Thr Val Arg Gly Ile Ala Val Lys Ala Gly Asp Ala Val Ala Val Gly
        50                  55                  60

Glu Thr Leu Met Thr Leu Ala Gly Ala Gly Ala Gly Ala Gly Ser Glu
65                  70                  75                  80

```
Leu Met Asn Thr Val Lys Pro Val Val Ser Ala Trp Lys Arg Asn Lys
                85                  90                  95

Tyr Gly Thr Tyr Met Glu Glu Ser Ala Arg Phe Thr Asn Gly Asn
            100                 105                 110

Gln Pro Ile Thr Val Arg Lys Ile Gly Pro Phe Leu Ser Cys Pro Val
            115                 120                 125

Ala Tyr Gln Phe Gln Pro Gly Gly Tyr Cys Asp Tyr Thr Glu Val Met
            130                 135                 140

Leu Gln Asp Gly His Val Trp Val Gly Tyr Thr Trp Glu Gly Gln Arg
145                 150                 155                 160

Tyr Tyr Leu Pro Ile Arg Thr Trp Asn Gly Ser Ala Pro Asn Gln
            165                 170                 175

Ile Leu Gly Asp Leu Trp Gly Glu Ile Ser
            180                 185

<210> SEQ ID NO 49
<211> LENGTH: 203
<212> TYPE: PRT
<213> ORGANISM: Artificial
<220> FEATURE:
<223> OTHER INFORMATION: Synthetic peptide

<400> SEQUENCE: 49

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
            20                  25                  30

Leu Glu Ala Met Lys Met Glu Thr Glu Ile Arg Ala Ala Gln Ala Gly
        35                  40                  45

Thr Val Arg Gly Ile Ala Val Lys Ala Gly Asp Ala Val Ala Val Gly
    50                  55                  60

Glu Thr Leu Met Thr Leu Ala Gly Ala Gly Ala Gly Ala Glu Leu Met
65                  70                  75                  80

Ser Asn Ser Thr Ala Gln Asp Pro Met Pro Phe Leu Lys Ser Ala Gly
                85                  90                  95

Tyr Gly Lys Ala Gly Gly Thr Val Thr Pro Thr Pro Asn Thr Gly Trp
            100                 105                 110

Lys Thr Asn Lys Tyr Gly Thr Leu Tyr Lys Ser Glu Ser Ala Ser Phe
            115                 120                 125

Thr Pro Asn Thr Asp Ile Ile Thr Arg Thr Thr Gly Pro Phe Arg Ser
            130                 135                 140

Met Pro Gln Ser Gly Val Leu Lys Ala Gly Gln Thr Ile His Tyr Asp
145                 150                 155                 160

Glu Val Met Lys Gln Asp Gly His Val Trp Val Gly Tyr Thr Gly Asn
            165                 170                 175

Ser Gly Gln Arg Ile Tyr Leu Pro Val Arg Thr Trp Asn Lys Ser Thr
            180                 185                 190

Asn Thr Leu Gly Val Leu Trp Gly Thr Ile Lys
            195                 200

<210> SEQ ID NO 50
<211> LENGTH: 204
<212> TYPE: PRT
<213> ORGANISM: Artificial
<220> FEATURE:
<223> OTHER INFORMATION: Synthetic peptide

<400> SEQUENCE: 50
```

```
Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
            20                  25                  30

Leu Glu Ala Met Lys Met Glu Thr Glu Ile Arg Ala Ala Gln Ala Gly
            35                  40                  45

Thr Val Arg Gly Ile Ala Val Lys Ala Gly Asp Ala Val Ala Val Gly
50                      55                  60

Glu Thr Leu Met Thr Leu Ala Gly Ala Gly Ala Gly Ala Glu Leu Met
65                  70                  75                  80

Asn Ser Phe Ser Asn Asn Thr Ala Gln Asp Pro Met Pro Phe Leu Lys
                85                  90                  95

Ser Ala Gly Tyr Gly Ser Asn Ser Thr Ser Ser Ser Asn Asn Asn Gly
                100                 105                 110

Tyr Lys Thr Asn Lys Tyr Gly Thr Leu Tyr Lys Ser Glu Ser Ala Ser
            115                 120                 125

Phe Thr Ala Asn Thr Asp Ile Ile Thr Arg Leu Thr Gly Pro Phe Arg
130                 135                 140

Ser Met Pro Gln Ser Gly Val Leu Arg Lys Gly Leu Thr Ile Lys Tyr
145                 150                 155                 160

Asp Glu Val Met Lys Gln Asp Gly His Val Trp Val Gly Tyr Asn Thr
                165                 170                 175

Asn Ser Gly Lys Arg Val Tyr Leu Pro Val Arg Thr Trp Asn Glu Ser
                180                 185                 190

Thr Gly Glu Leu Gly Pro Leu Trp Gly Thr Ile Lys
            195                 200

<210> SEQ ID NO 51
<211> LENGTH: 182
<212> TYPE: PRT
<213> ORGANISM: Artificial
<220> FEATURE:
<223> OTHER INFORMATION: Synthetic peptide

<400> SEQUENCE: 51

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
            20                  25                  30

Leu Glu Ala Met Lys Met Glu Thr Glu Ile Arg Ala Ala Gln Ala Gly
            35                  40                  45

Thr Val Arg Gly Ile Ala Val Lys Ala Gly Asp Ala Val Ala Val Gly
50                      55                  60

Glu Thr Leu Met Thr Leu Ala Gly Ala Gly Ala Gly Ala Gly Ser Glu
65                  70                  75                  80

Leu Met Pro Pro Val Pro Ala Gly Tyr Thr Leu Asp Lys Asn Asn Val
                85                  90                  95

Pro Tyr Lys Lys Glu Ala Gly Asn Tyr Thr Val Ala Asn Val Lys Gly
            100                 105                 110

Asn Asn Val Arg Asp Gly Tyr Ser Thr Asn Ser Arg Ile Thr Gly Val
            115                 120                 125

Leu Pro Asn Asn Ala Thr Ile Lys Tyr Asp Gly Ala Tyr Cys Ile Asn
130                 135                 140

Gly Tyr Arg Trp Ile Thr Tyr Ile Ala Asn Ser Gly Gln Arg Arg Tyr
145                 150                 155                 160
```

```
Ile Ala Thr Gly Glu Val Asp Lys Ala Gly Asn Arg Ile Ser Ser Phe
                165                 170                 175

Gly Lys Phe Ser Ala Val
            180

<210> SEQ ID NO 52
<211> LENGTH: 271
<212> TYPE: PRT
<213> ORGANISM: Artificial
<220> FEATURE:
<223> OTHER INFORMATION: Synthetic peptide

<400> SEQUENCE: 52

Met Val Gly Ala Val Thr Ala Pro Leu Ala Gly Thr Ile Trp Lys Val
1               5                   10                  15

Leu Ala Ser Glu Gly Gln Thr Val Ala Gly Glu Val Leu Leu Ile
                20                  25                  30

Leu Glu Ala Met Lys Met Glu Thr Glu Ile Arg Ala Ala Gln Ala Gly
            35                  40                  45

Thr Val Arg Gly Ile Ala Val Lys Ala Gly Asp Ala Val Ala Val Gly
        50                  55                  60

Glu Thr Leu Met Thr Leu Ala Gly Ala Gly Ala Gly Ser Glu
65                  70                  75                  80

Leu Thr Asn Lys Pro Glu Thr Asp Thr Pro Ala Thr Asp Ala Gly Glu
                85                  90                  95

Glu Ile Glu Lys Ile Pro Asn Ser Asp Val Lys Val Gly Asp Thr Val
            100                 105                 110

Lys Val Lys Phe Asn Val Asp Ala Trp Ala Thr Gly Glu Ala Ile Pro
        115                 120                 125

Gln Trp Val Lys Gly Asn Ser Tyr Lys Val Gln Glu Val Thr Gly Ser
    130                 135                 140

Arg Val Leu Leu Glu Gly Ile Leu Ser Trp Ile Ser Lys Gly Asp Ile
145                 150                 155                 160

Glu Leu Leu Pro Asp Ala Thr Val Val Pro Asp Lys Gln Pro Glu Ala
                165                 170                 175

Thr His Val Val Gln Tyr Gly Glu Thr Leu Ser Ser Ile Ala Tyr Gln
            180                 185                 190

Tyr Gly Thr Asp Tyr Gln Thr Leu Ala Ala Leu Asn Gly Leu Ala Asn
        195                 200                 205

Pro Asn Leu Ile Tyr Pro Gly Gln Val Leu Lys Val Asn Gly Ser Ala
    210                 215                 220

Thr Ser Asn Val Tyr Thr Val Lys Tyr Gly Asp Asn Leu Ser Ser Ile
225                 230                 235                 240

Ala Ala Lys Leu Gly Thr Thr Tyr Gln Ala Leu Ala Ala Leu Asn Gly
                245                 250                 255

Leu Ala Asn Pro Asn Leu Ile Tyr Pro Gly Gln Thr Leu Asn Tyr
            260                 265                 270
```

```
<210> SEQ ID NO 53
<211> LENGTH: 235
<212> TYPE: PRT
<213> ORGANISM: Artificial
<220> FEATURE:
<223> OTHER INFORMATION: Synthetic peptide

<400> SEQUENCE: 53

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
            20                  25                  30

Leu Glu Ala Met Lys Met Glu Thr Glu Ile Arg Ala Ala Gln Ala Gly
        35                  40                  45

Thr Val Arg Gly Ile Ala Val Lys Ala Gly Asp Ala Val Ala Val Gly
    50                  55                  60

Glu Thr Leu Met Thr Leu Ala Gly Ala Gly Ala Gly Ser Glu
65                  70                  75                  80

Leu Ala Pro Lys Tyr Gln Val Gly Gln Ala Ile Arg Phe Thr Ser Ile
                85                  90                  95

Tyr Pro Thr Pro Asp Ala Leu Ile Asn Glu His Leu Ser Ala Glu Ala
            100                 105                 110

Leu Trp Thr Gln Val Gly Thr Ile Thr Ala Lys Leu Pro Asp Arg Gln
        115                 120                 125

Asn Leu Tyr Arg Val Glu Asn Ser Gly His Leu Leu Gly Tyr Val Asn
    130                 135                 140

Asp Gly Asp Ile Ala Glu Leu Trp Arg Pro Gln Thr Lys Lys Ser Phe
145                 150                 155                 160

Leu Ile Gly Val Asp Glu Gly Ile Val Leu Arg Ala Gly Gln Pro Ser
                165                 170                 175

Leu Leu Ala Pro Ile Tyr Gly Ile Trp Pro Lys Asn Thr Arg Phe Tyr
            180                 185                 190

Tyr Asp Thr Phe Tyr Ile Ala Asp Gly Tyr Val Phe Ile Gly Gly Thr
        195                 200                 205

Asp Thr Thr Gly Ala Arg Ile Tyr Leu Pro Ile Gly Pro Asn Asp Gly
    210                 215                 220

Asn Ala Gln Asn Thr Trp Gly Ser Phe Ala Ser
225                 230                 235

<210> SEQ ID NO 54
<211> LENGTH: 27
<212> TYPE: DNA
<213> ORGANISM: Artificial
<220> FEATURE:
<223> OTHER INFORMATION: Synthetic primer

<400> SEQUENCE: 54
atggttggtg cagttacagc tccgctg                                    27

<210> SEQ ID NO 55
<211> LENGTH: 27
<212> TYPE: DNA
<213> ORGANISM: Artificial
<220> FEATURE:
<223> OTHER INFORMATION: Synthetic primer

<400> SEQUENCE: 55
atggtaggtg cagttacagc tccgctg                                    27
```

```
<210> SEQ ID NO 56
<211> LENGTH: 27
<212> TYPE: DNA
<213> ORGANISM: Artificial
<220> FEATURE:
<223> OTHER INFORMATION: Synthetic primer

<400> SEQUENCE: 56
atggttggtg cagtaacagc tccgctg                                        27
```

METHOD AND MEANS FOR ENRICHMENT, REMOVAL AND DETECTION OF GRAM-POSITIVE BACTERIA

This application is a national phase application under 35 U.S.C. §371 of International Patent Application No. PCT/DE 2007/002320 filed Dec. 21, 2007 claims priority to German Patent Application No. DE 10 2006 061 002.4 filed Dec. 22, 2006. The entire text of each of the above-referenced disclosures is specifically incorporated herein by reference without disclaimer.

The present invention relates to polypeptides comprising a enzymatically non-active cell wall binding domain of an endolysin or another cell wall lysing enzyme, and a sequence according to SEQ ID NO: 1 or derivatives thereof, wherein the polypeptide besides the cell wall binding domain comprises no further domains of an endolysin or of another cell wall lysing enzyme, as well as means for their preparation. The present invention further relates to methods for binding, enriching, removing from a sample, capturing and/or detecting bacteria, particularly gram positive bacteria.

Gram positive bacteria are wildly spread in the environment. They can be found in samples like soil, water, plant material, feces, but also in humans and animals. A whole series of pathogen germs, e.g. of the species *listeria, bacillus, clostridium, staphylococcus, streptococcus, enterococcus, micrococcus* or *mycobacteria* is particularly relevant in the food sector as well as in prevention, diagnostics and therapy of infection diseases in humans and animals.

Bacteria of the group *Bacillus cereus* represent microorganisms of major economic and medical importance as well as prominent relevance in the sector of bioterrorism. The bacteria are closely related to each other within a group; a large amount of which are sequenced (Rasko et al, FEMS Microbiol. Reviews, 2005, 29, 303-329). They are wildly spread in nature and present in different kinds of food, mostly of plant origin. They are aerobic living, moving, rod shaped gram-positive bacteria. Due to their resistant endospores, they are able to survive different methods, used to cure food, e.g. like drying or heating. Frequently contaminated food is mainly starch containing food, cereals, rice, spices, vegetables and ready-to-eat products. Meat can be contaminated by using contaminated spices. Milk products are frequently contaminated, because the spores survive pasteurisation and unrestricted proliferation is subsequently possible. The *Bacillus cereus* group consists of six closely related species and includes besides the food germ *Bacillus cereus* the extremely dangerous human pathogen germ *Bacillus anthracis*, which is enormously relevant in the sector of bioterrorism, the insect pathogen *Bacillus thuringiensis* (widely spread by microbiological insecticides on the basis of *B. thuringiensis*), the rhizoid-like *Bacillus mycoides* as well as *Bacillus pseudomycoides* and *Bacillus weihenstephanensis*.

*Listeria* are human and animal pathogen bacteria, frequently present in food, particularly in fish, meat and milk products. The genus *listeria* comprises six different species with 16 different serotypes. Although only a small portion of the food related diseases is caused by *listeria* (about 1% in USA), almost 30% of the annually fatal diseases, caused by food pathogens, are cause by this germ. Affected are mainly immune suppressed persons, e.g. older people, diabetes patients, cancer patients and/or AIDS patients. Pregnant women and the yet unborn child represent 25% of all cases of listeriosis patients.

*Staphylococcus* and *enterococcus* are currently the most problematic pathogens associated with infection diseases, since they increasingly develop multi resistant germs (e.g. MRSA—multi resistant *Staphylococcus aureus* and VRE—vancomycin resistant *Enterococcus*), leading to dramatic developments, i.e. bad disease prognosis as well as an explosion of the costs, mainly in stationary health care.

Potential pathogens are frequently present in very small cell numbers in the infection state and in food area and additionally accompanied by an interfering background flora. On the one hand methods are needed for efficiently removing relevant gram-positive germs and on the other hand methods for selectively enriching these germs, e.g. to achieve a sensitive detection.

Criteria for a good detection method are sensitivity, rapidity, reliability as well as a simple and cost efficient application.

Initially, there is basically always the enrichment of the organisms which should be detected. Generally this is achieved in conventional methods in a multi-step process. A primary enrichment mostly occurs with non- or low-selective liquid nutrient media. Subsequently a selective secondary enrichment occurs, followed by a primary isolation which frequently takes place on selective agar. Single colonies are enriched again in subcultures and subsequently detected with diverse detection methods. These conventional methods take a very long time until the positive detection of a germ. The standard detection times for *listeria* are more than 4-7 days according, to ISO 11290-1:1996/FDAM 1:2004(E) and 4-7 days according to FDA and USDA/FSIS. The enrichment of bacteria of the *Bacillus cereus* group takes 1.5 to 2.5 days according to standard methods (USFDA-method, chapter 14; ISO_7932:2004), the subsequent detection 2 days and a more detailed discrimination within the *Bacillus cereus* group again 2-3 days.

In food industry the detection time is an important sector concerning the short shelf-live of some kind of foods and the cost intensive storage, which is necessary until it has been made sure that the sample is not contaminated. Moreover, cost intensive product recalls can consistently be observed, if contaminated goods are delivered ahead of schedule prior to the receipt of the control results. In health care long detection times are also problematic, since appropriate specific treatment methods on a safe basis can also be performed not until the identification of the pathogen germ.

As faster alternatives compared to conventional enrichment and detection methods, antibody based methods were frequently used (e.g. U.S. Pat. No. 6,699,679, US 2004/0197833, UA 2006/0211061, Fluit et al., 1993, Appl Environ Microbiol., 59, 1289-1293, Jung et al., 2003, J Food Prot., 66, 1283-1287, Hawkes et al., 2004, Biosens. Bioelectron., 19, 1021-1028). The application of sugar binding lectines as receptors for the carbohydrate portion of the bacterial surface was also considered. However, these are mostly too unspecific to select certain bacteria from a mixed culture and frequently exhibit agglutination problems based on their multimeric binding properties. The recovery rate of bacteria was also relatively poor using antibody based methods, the rate was in a range from 5% to 25%. Further disadvantages of immunomagnetic separation methods (IMS) are besides the poor recovery rate, insufficient sensitivity at low contamination rates, cross reactions with other cells and frequently agglutination problems with antibody coated beads. Additionally it is relatively difficult to obtain antibodies against intact bacteria. Although these methods are very promising in case of pure cultures, they exhibit significant problems in case of mixed cultures or complex matrices such as foods.

As alternative to antibodies the use of cell wall binding domain (CBDs) from bacteriophages peptidoglycan hydrolases for binding of gram-positive bacteria are known in the state of the art (Loessner et al., 2002, Mol. Microbiol., 44, 335-349). EP 1147419 and WO2004/088321 use CBDs for the detection of cells, wherein the CBDs are bound to a solid phase and generally carry a marker.

EP 1399551 describes a method for the selective purification of gram-negative bacteria cells or cell fragments using bacteriophage capsid proteins or bacteriophage tail proteins. In this case the bacteria are bound in a 2-step-method, first binding of the binding molecules to the target cells occurs, followed by the immobilisation of the complexes to solid carriers. The immobilisation occurs by coupling the bacteriophage tail proteins with the help of his-tag, biotin or strep-tag to functionalized surfaces of solid carriers. Especially for this 2-step-method an efficient, fast and non-covalent coupling of the binding protein-target cell-complex to a functionalized carrier is of crucial relevance particularly if the target cells shall be separated from the sample together with the solid carrier.

U.S. Pat. No. 5,252,466 discloses a method to prepare fusion proteins including a tag for in vivo biotinylation and are therefore easy to purify. In this case the biotinylation domains are for example the 1.3S subunit of the *Propionibacterium shermanii* transcarboxylase, tomato-biotin-protein, the α-subunit of the *Klebsiella pneumoniae* oxalacetate decarboxylase or the *Escherichia coli* biotin carboxyl carrier protein, expressed in the same reading frame together with a biotin ligase of the plasmid and therefore are biotinylated in vivo. With the help of a phage display system a proteolytic more stable minimal version of the biotinylation domain of *klebsiella* oxalacetate decarboxylase was developed, suitable to purify and detect respective fusion proteins (Stolz et al., 1998, FEBS-Lett. 440, 213-217). U.S. Pat. No. 5,874,239 also claims a method for biotinylation of fusion proteins suggesting a number of tags, so called "Avi-tags", which are, with a length of 13 to 50 amino acids preferably about 20 amino acids, shorter than the biotinylation domains of *klebsiella* oxalacetate decarboxylase.

Thus, the problem underlying the present invention is to provide more efficient and productive methods and the means to perform said method for fast, simply and efficiently binding, enriching, removing, capturing and detecting gram positive bacteria.

The problem is solved by the subject matter defined in the patent claims.

The following figures illustrate the invention.

FIG. 1: Bacteriophage tail proteins with JS-tag

FIG. 1A: Comparison of the expression and the functional assembly of P22 like phage tail proteins with different tags A P22 like phage tail protein from *Salmonella* was cloned at the N-terminus with Strep-tag, Avi-tag and JS-tag and expressed in *E. coli* HMS174 (DE3) and *E. coli* JM83, respectively. The samples were loaded on a 12% SDS-gel and stained with Coomassie. The experiment is described in experiment 1. M: Marker, P: Pellet; S: Supernatant; +: induced; −: not induced; nb: not boiled. The arrows indicate the positions of the phage tail protein monomers and trimers, respectively.

Figure 1B:
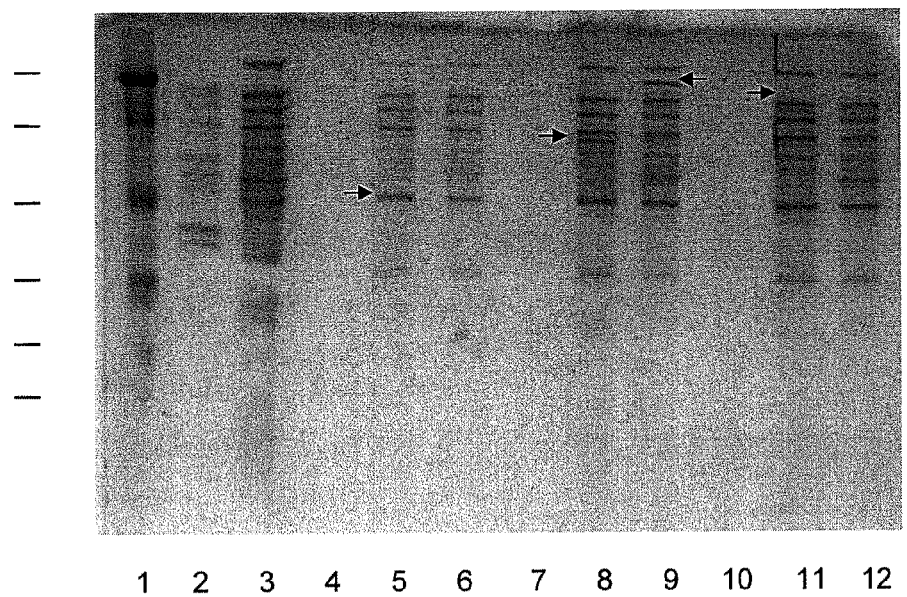

FIG. 1B: Cloning and expression with JS-tag of three bacteriophage tail proteins from *salmonella* phages Three different bacteriophage tail proteins (Tsp) from *salmonella* phages were cloned as fusion proteins with JS-tag and expressed in *E. coli* HMS174 (DE3). The samples from the cell lysate were loaded on a 12% SDS-gel and stained with Coomassie. Lane 1: Marker (molecular weight from top: 118 kDa, 85 kDa, 47 kDa, 36 kDa, 26 kDa, 20 kDa), lane 2: Pellet (P), not induced, lane 3: supernatant (S), not induced, lane 4-12 (all post induction), lane 4: Felix like tail protein (Felix-Tsp, 48 kDa), P, lane 5: Felix-Tsp, S, boiled, lane 6: Felix-Tsp, not-boiled, lane 7: P22 like tail protein (P22-Tsp, 67 kDa), P, lane 8: P22-Tsp, S, boiled, lane 9: P22-Tsp, S, not-boiled, lane 10: ε15-like tail protein (ε15-Tsp, 93 kDa), P, lane 11: ε15-Tsp, S, boiled, lane 12: ε15-Tsp, S, not-boiled. The arrows indicate the expected positions for the phage tail protein monomers and SDS-resistant trimers (in not boiled samples).

Figure 1C:
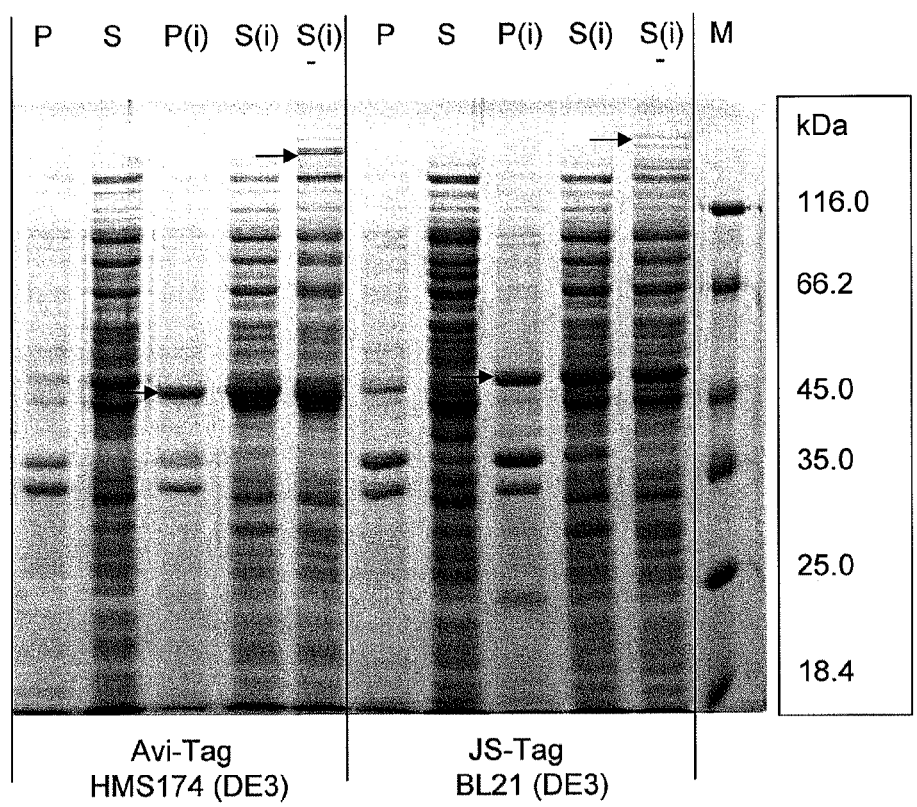

FIG. 1C: Comparative cloning and expression with Avi-tag and JS-tag of a tail protein from *campylobacter* phage, respectively A *campylobacter* phage tail protein (putative tail fibre protein H for *Campylobacter jejuni*, Acc. No: ZP01067412) was cloned with N-terminal Avi-tag and JS-tag (version 5b), respectively, in the plasmid pET21d and expressed in *E. coli* HMS174 (DE3) and *E. coli* BL21(DE3), respectively. The experiment is described in experiment 1. A 9% Coomassie-stained SDS-gel is depicted with different samples from the expression and solubility test. P: Pellet; S: Supernatant; (i) induced; −: not boiled; M: Marker. The arrows indicate the positions of the monomers and trimers (in not boiled samples), respectively, of the phage tail proteins after induction.

Figure 2:
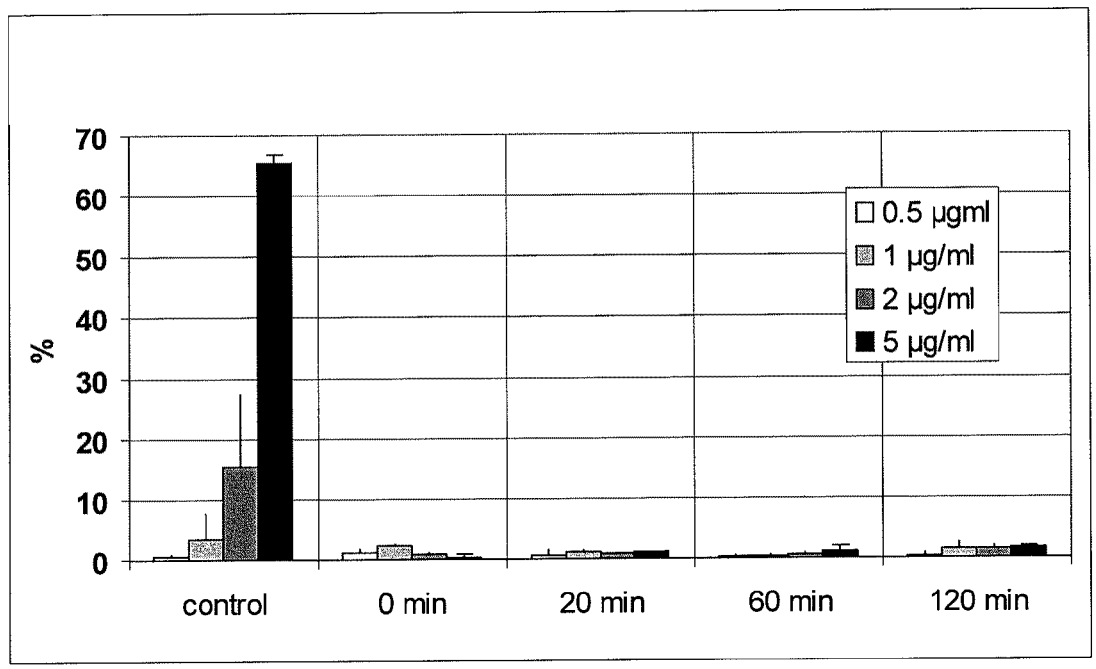

FIG. 2: *Listeria* CBDs become completely inactive after chemical biotinylation

It is depicted, which part of the introduced *listeria* is still bound in the binding assay after chemical biotinylation. Protein concentrations of 0.5 μg/ml, 1 μg/ml, 2 μg/ml and 5 μg/ml were used in the test. Incubation with NHS-biotin occurred for 0 min, 20 min, 60 min and 120 min. Avi-CBD served as control.

FIG. 3: Comparison of 1-step and 2-step methods

FIG. 3A depicts a comparison of the *listeria* detection from camembert according to the 1-step and 2-step as well as the ISO-method The time dependence is comparatively analysed according to which very low concentrations of *L. monocytogenes* can be detected in camembert with the different methods. 5 portions of camembert (25 g each) were contaminated with 0, 2, 4, 15 and 46 CFU (colony forming units) and tested after 4 h, 6 h, and 24 h of concentration according to the 1-step, 2-step or ISO (ISO: 11290-1:1996 FDAM1)-method. For the 1-step and 2-step method the Strep-tag-GFP-CBD511_f2 was used as a specific ligand. The values are determined from 4 experiments each. (0: no colonies on plate, X: <10 colonies, XX: 10-30 colonies, XXX: >30 colonies).

FIG. 3B depicts the concentration dependence in the 1-step and 2-step method of the detection of *L. monocytogenes* (strain EGDe, black bars, and ScottA, shaded bars) in mozzarella using the fusion proteins JS-GFP-CBD511_f2. The performance of the experiment is described in experiment 3b. In each case it is depicted how many percent of the total introduced *listeria* cells of the respective strains from 1 ml of sample of mozzarella were recovered. The values were determined from 2 experiments each.

FIG. 4: JS-tag in comparison to Avi-tag

Figure 4A:
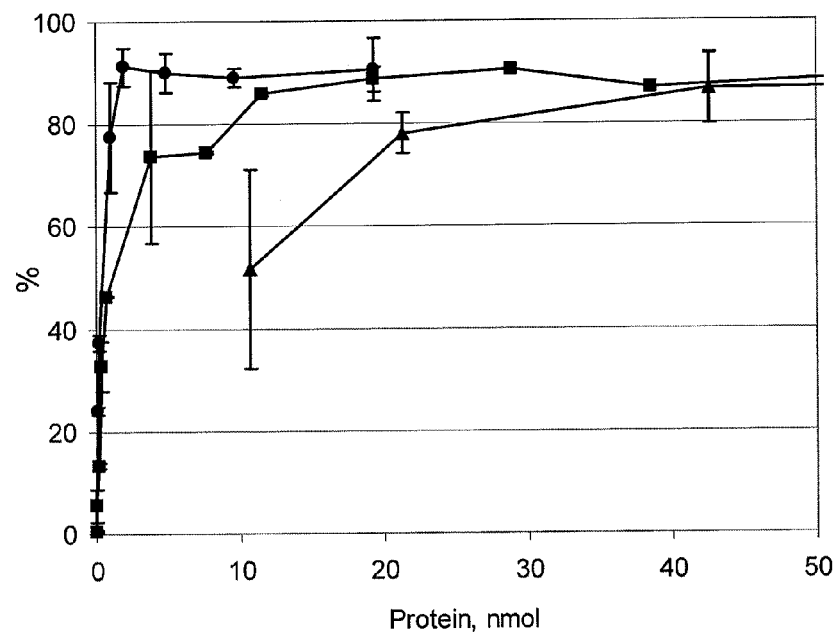

FIG. 4A: Comparison of the cell binding capacity of JS-tag and Avi-tag constructs The cell binding capacity of different constructs was tested with the *listeria* strains ScottA according to the 2-step-method. The following constructs were used: JS-GFP_CBD511_f3 (circle), JS-CBD511_f3 (square) and Avi-GFP CBD511_f3 (triangle). Given is the portion of the *listeria* attached to the magnetic beads in percent of the introduced cells. All experiments were performed twice and the average values were determined.

Figure 4B:
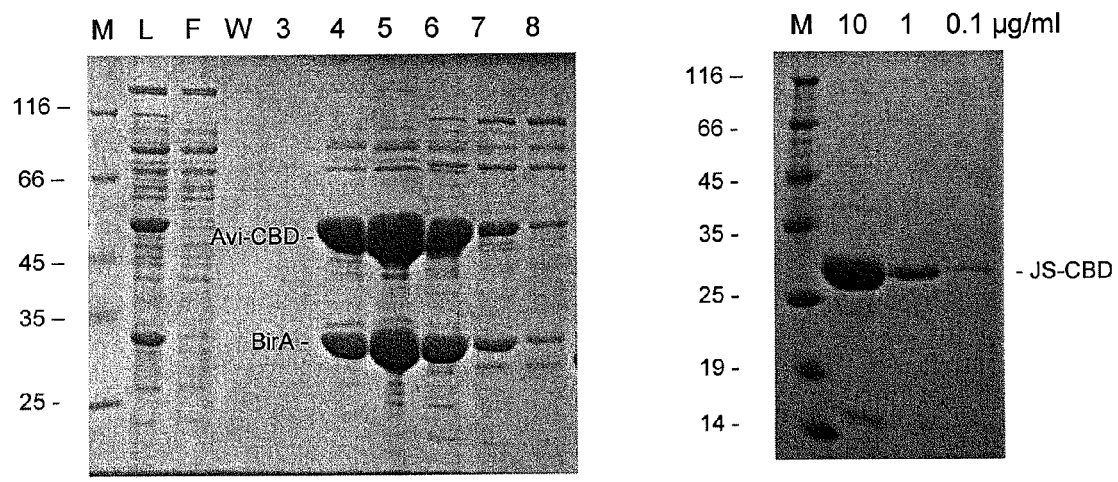

FIG. 4B: Comparative purification of Avi-GFP-CBD511_f2 and JS-CBD511_f2

The left picture depicts a Coomassie-stained gel of the purification of Avi-GFP-CBD511_f2, the right depicts the end product of the purification of JS-CBD511_f2. The experiment is described in experiment 4b. M: Marker; L: Load on the column; F: flow through; W: Wash fraction; 3-8: fractions containing Avi-GFP-CBD511_f2. 10, 1, 0.1 µg/ml: loaded protein concentrations for JS-CBD511_f2. The positions for the bands for Avi-GFP-CBD511_f2 and JS-CBD511_f2 as well as BirA are indicated.

Figure 4C:
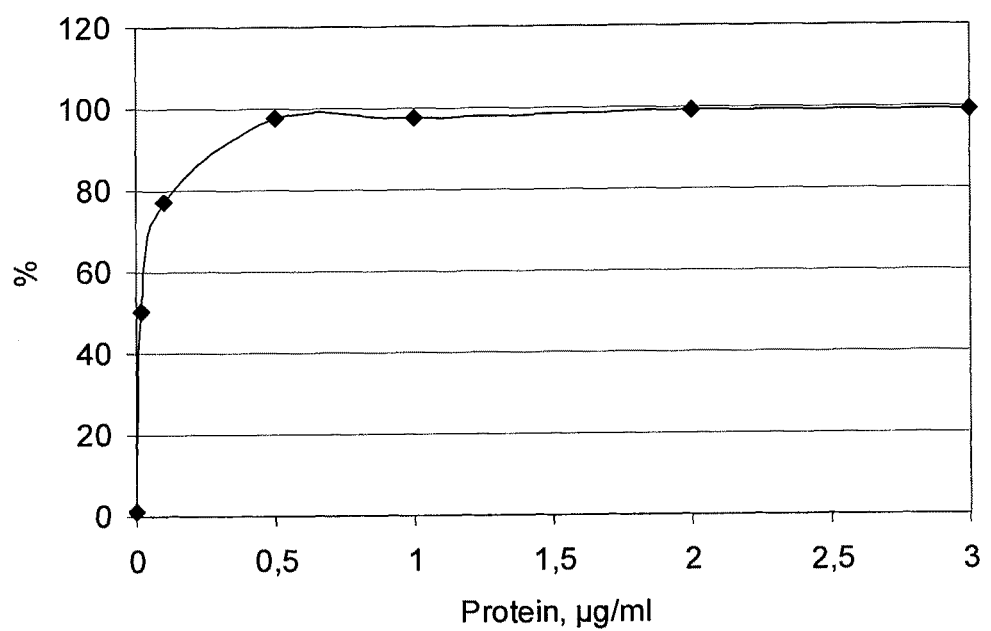

FIG. 4C: Concentration dependence of the binding of listeria

It was analyzed, at which concentration of specific binding protein a maximum cell binding is achieved. As binding protein JS-CBD511_f3 was introduced in the concentrations 0 µg/ml, 0.02 µg/ml, 0.1 µg/ml, 0.5 µg/ml, 1 µg/ml, 2 µg/ml and 3 µg/ml. The experiment is described in experiment 4b.

Figure 5:
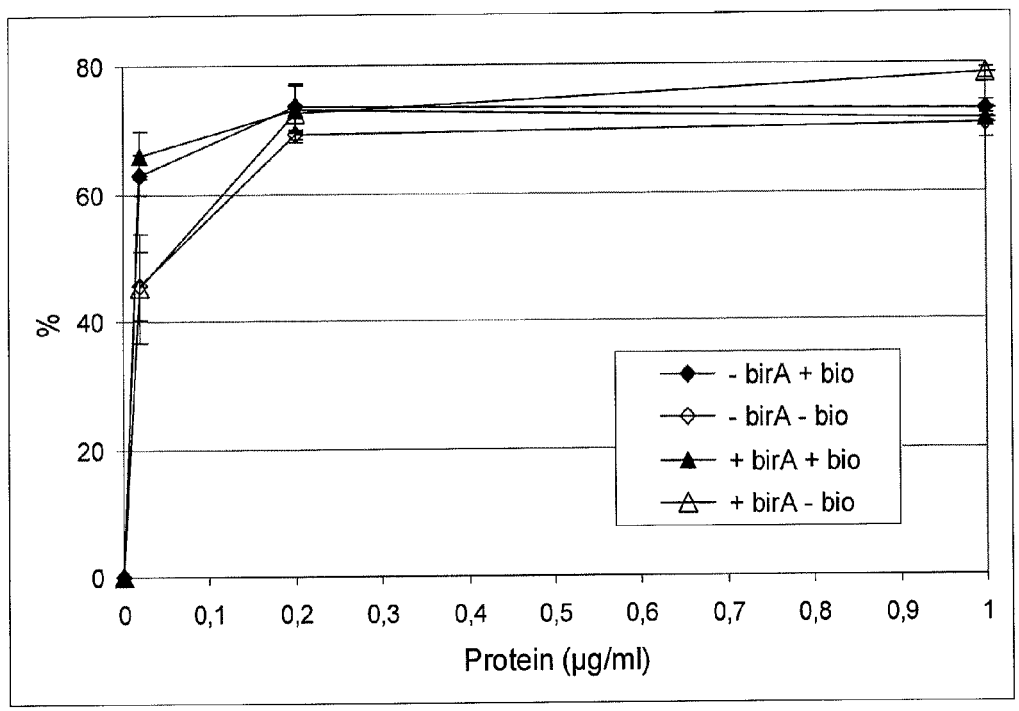

FIG. 5: Effect of the coexpression of BirA on the binding efficiency of JS-tag CBDs Illustrated is the portion of the bound bacteria cells (Listeria ScottA) in dependence of the introduced amount of specific binding protein JS5b-CBD511_f2. Concerning one part of the proteins, BirA was coexpressed in an additional plasmid (triangles), concerning the other part no coexpression occurred with BirA (rhombuses). Furthermore, biotin was additionally added (filled symbols) in 2 experiments, whereas this remained undone in 2 experiments (open symbols).

Figure 6:
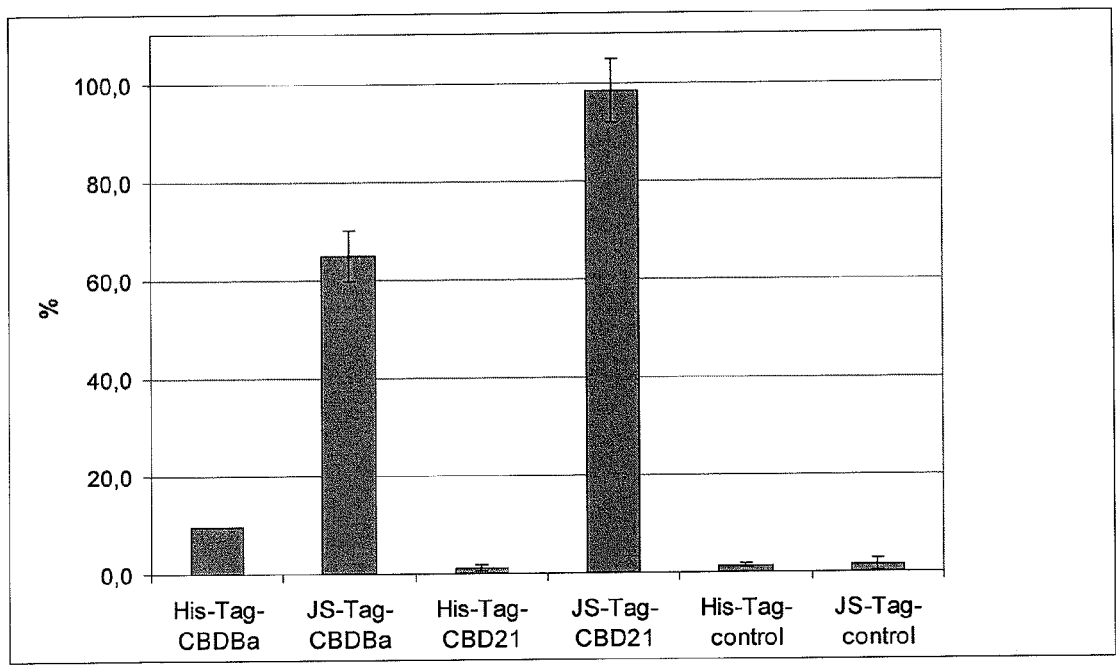

FIG. 6: Comparison of the specific binding of JS-tag-CBDs to streptavidin beads with the binding of his-tag-CBDs to nickel-NTA-beads Bacillus cereus bacteria were bound using a 2-step method with two different CBDs (CBDBa and CBD21) either via hexa-his-tag to nickel-NTA-magnetic beads or via JS-tags to streptavidin-magnetic beads. Depicted is the portion of specific bound bacteria compared to the totally introduced bacteria (concentration $3\times10^3$ CFU/ml).

FIG. 7: Bacteria binding with strep-tag and JS-tag CBDs in different media, respectively Listeria monocytogenes EGDe cells were concentrated with the method according to the present invention from different media and PBST-buffers, respectively. The experiment is described in experiment 8.

FIG. 7A: Avi-CBD511_f2 (5 µg/ml) was used to concentrate listeria.

FIG. 7B: JS-CBD511_f2 (5 µg/ml) was used to concentrate listeria.

Figure 8:
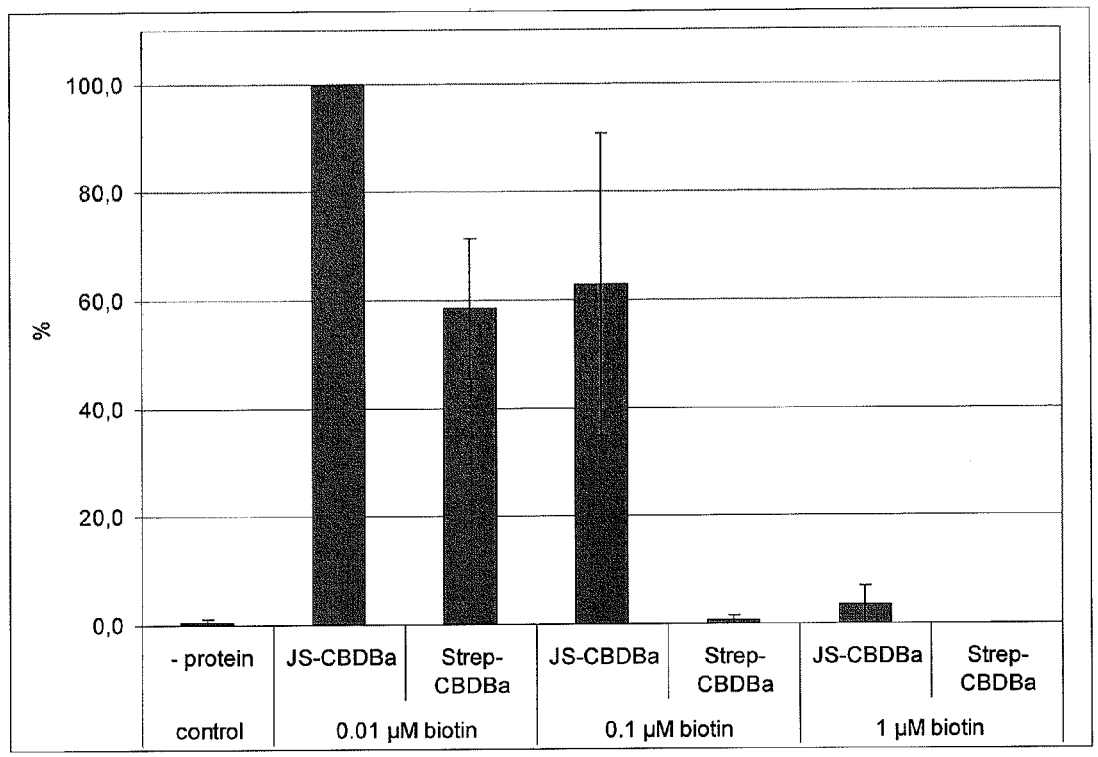

FIG. 8: Bacteria binding in biotin containing samples

The specific concentration of Bacillus cereus with the constructs strep-tag-CBDBa and JS-tag-CBDBa was analyzed in comparison at biotin concentrations of 0.01 µM, 0.1 µM and 1 µM.

FIG. 9: Long-term stability of the JS-tag CBDs under different conditions

JS-CBD511_f3 as well as magnetic streptavidin beads were incubated in a temperature range from −20° C. to 37° C. and subsequently introduced in cell binding tests with Listeria monocytogenes ScottA.

Figure 9A:
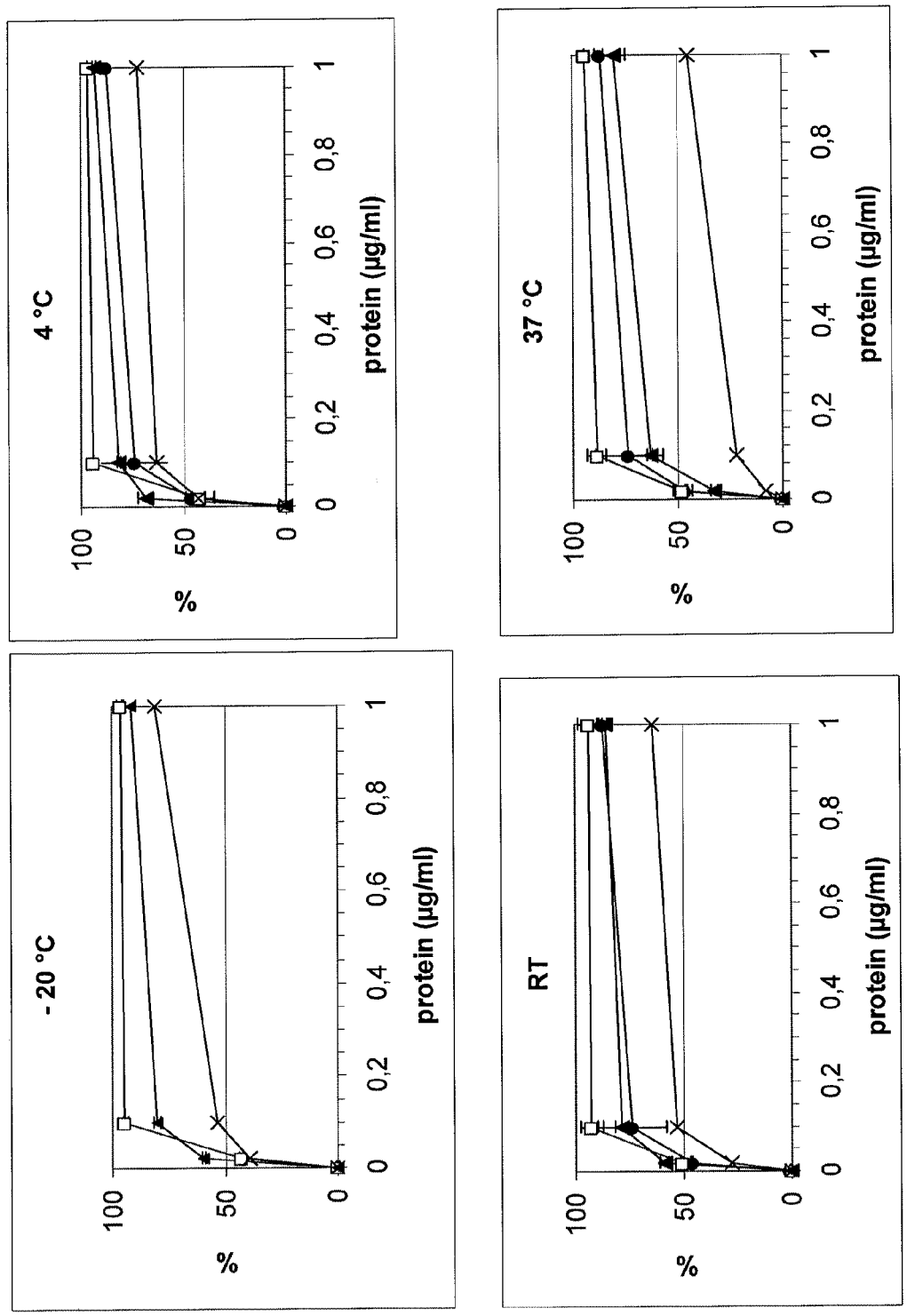

FIG. 9A: Incubation in sodium phosphate, pH 7, 2 mM EDTA. Given is the portion of bound listeria at the given concentration of JS-CBD511_f3 after one day (full circle), 14 days (open rectangle), 60 days (full triangle) and 126 days (cross).

Figure 9B:
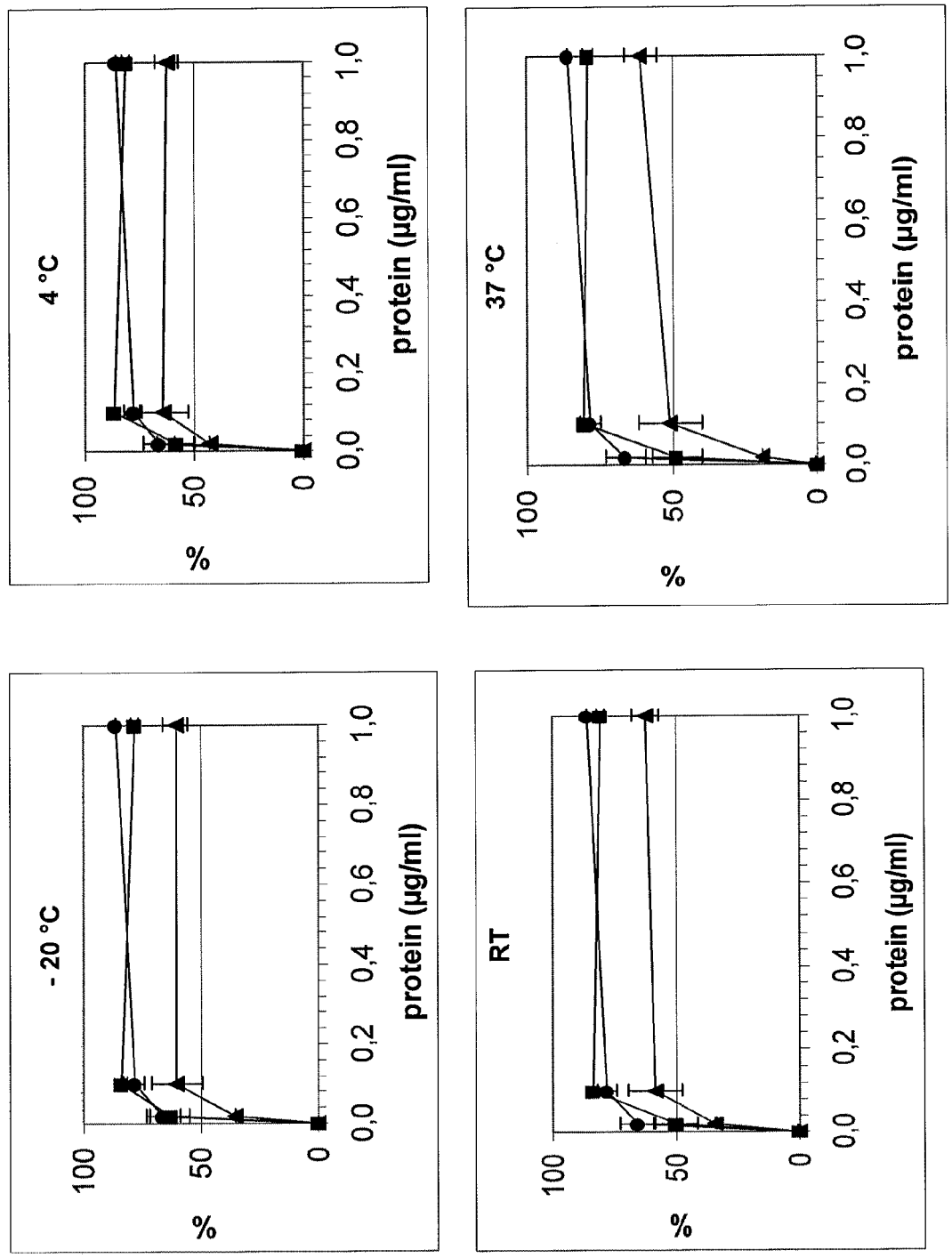

FIG. 9B: Incubation in imidazol, 100 mM NaCl, pH 7, +30% AS. Given is the portion of the bound listeria at the indicated concentration of JS-CBD511_f3 after 0 days (circle), 33 days (rectangle) and 74 days (triangle).

FIG. 10: Listeria capture with JS-CBD511-constructs from different foods

Figure 10A:
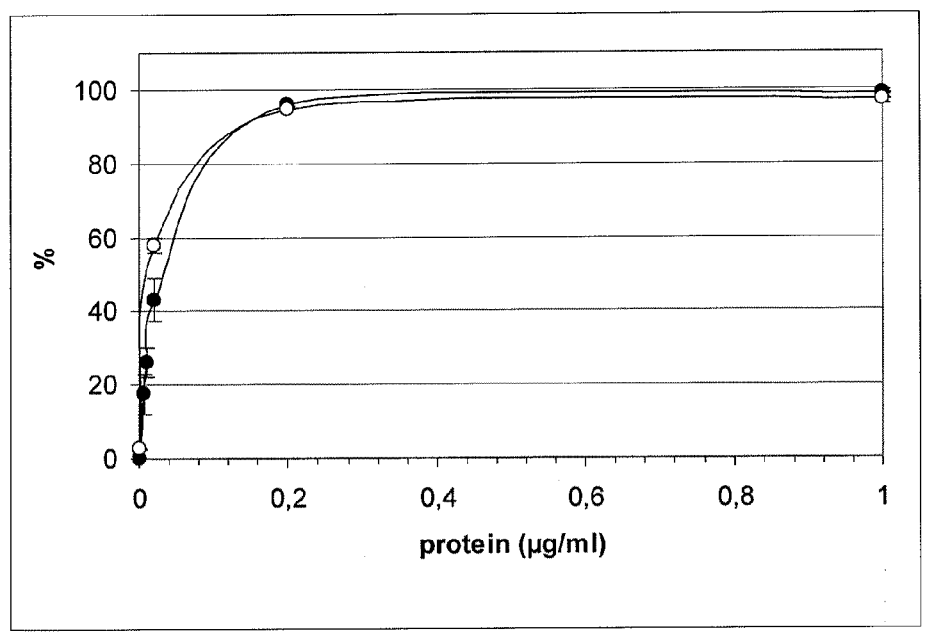

FIG. 10A: Concentration dependent removal of Listeria monocytogenes ScottA from milk and cheese. JS4b-CBD511_f2 was used for binding in different concentrations. It is given, how many percent of the introduced bacteria were bound to the magnetic beads at the respective protein concentrations.

Figure 10B:
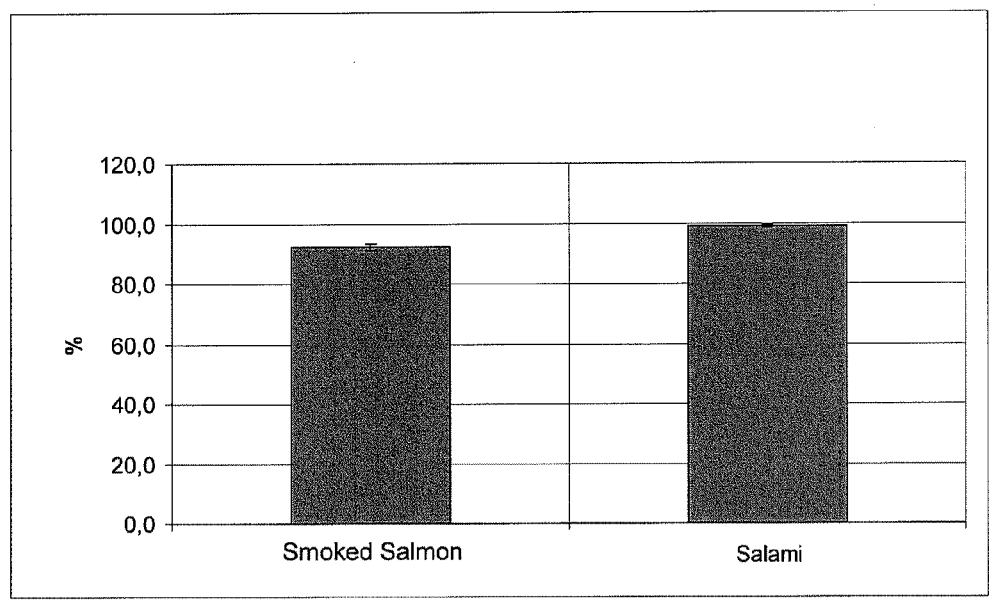

FIG. 10B: Removal of Listeria innocua from salami and smoked salmon.

Figure 11A:
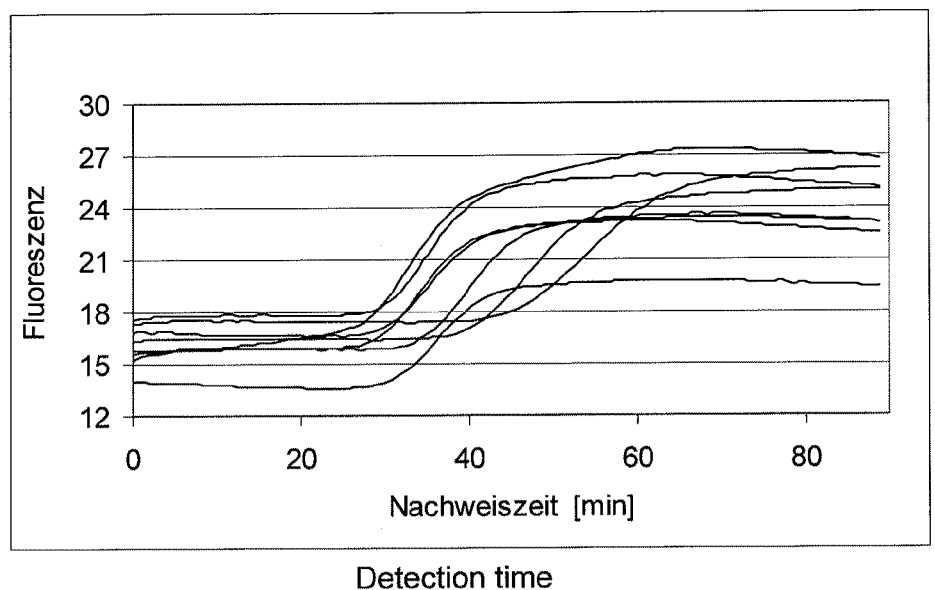
Figure 11B:
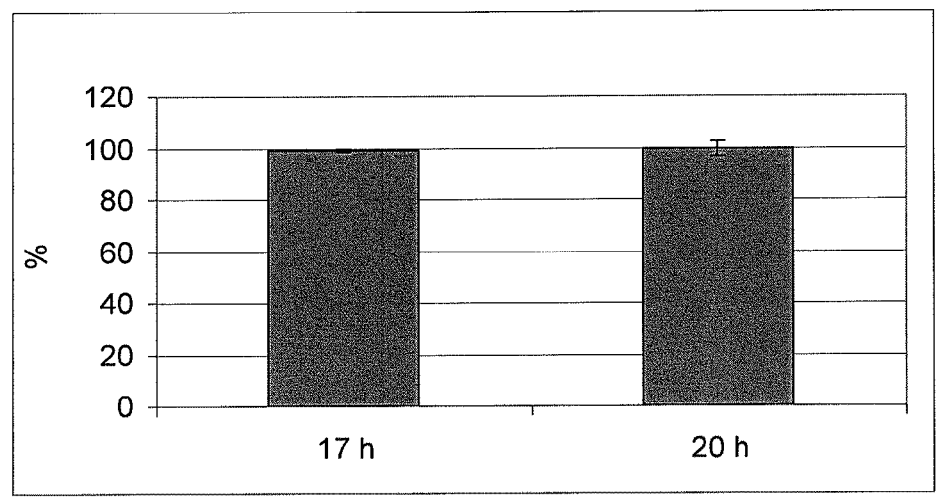

FIG. 11: Concentration of listeria from foods and subsequent detection with NASBA technique Listeria were concentrated by using JS5b-CBD511_f2 from Salami, which was contaminated with small amounts of Listeria monocytogenes ScottA (5 CFU/25 g) and after 17 h and 20 h of pre-incubation in LEB-FDA medium, respectively. In FIG. 11A the fluorescence signal is depicted emerging after the enzyme reaction with listeria specific primers. FIG. 11B depicts, how many percent of the introduced bacteria can be bound from the sample with JS5b-CBD511_f2.

Figure 12:
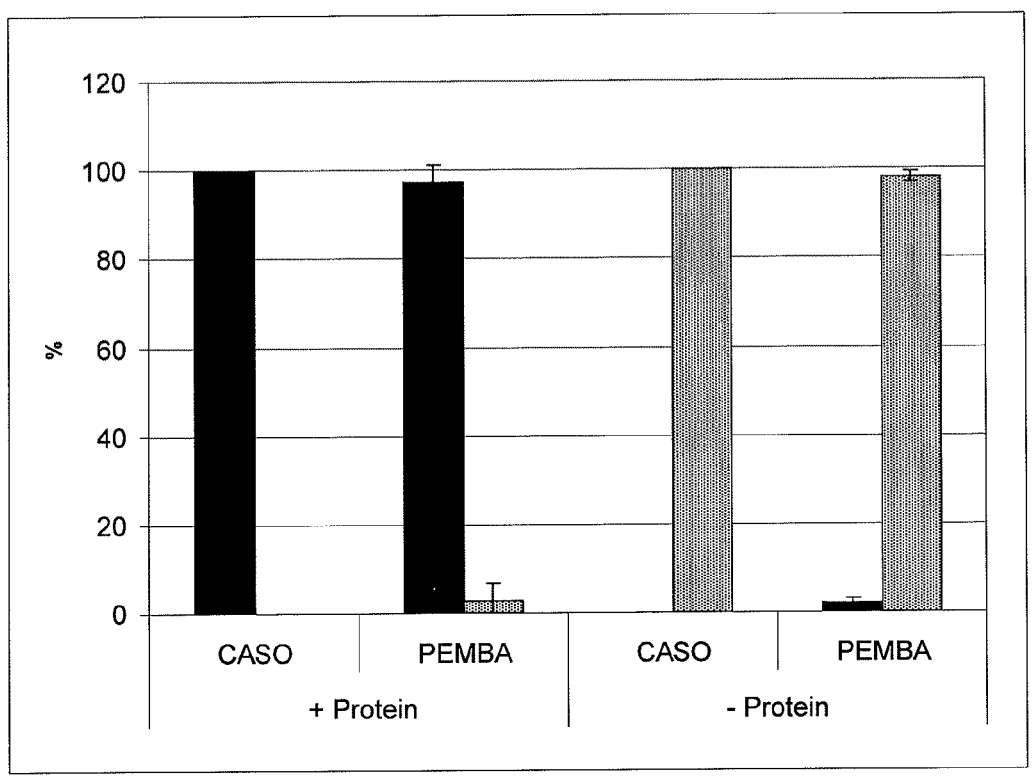

FIG. 12: Specific binding of Bacillus cereus from a mixture of bacteria

Bacillus cereus is concentrated using the specific JS-tag-CBDBa from a mixture of bacteria (Bacillus cereus (DSMZ345), Salmonella tennesse, Listeria monocytogenes (ScottA), Staphylococcus aureus, E. coli HMS174 (DE3)). Given is the number of bound Bacillus cereus cells in percent compared to the totally recovered cells bound to the magnetic beads (black bars) or in the supernatant and the washing fraction (shaded bars), respectively. On the one hand, the cells were plated on a complete medium (CASO, Merck) to maintain also the other cells from the mixed culture, on the other hand cells were plated on selective plates for Bacillus cereus (PEMBA). As controls experiments were performed such that magnetic beads but no binding protein was added.

FIG. 13: Concentration of Bacillus cereus from foods

Figure 13A:
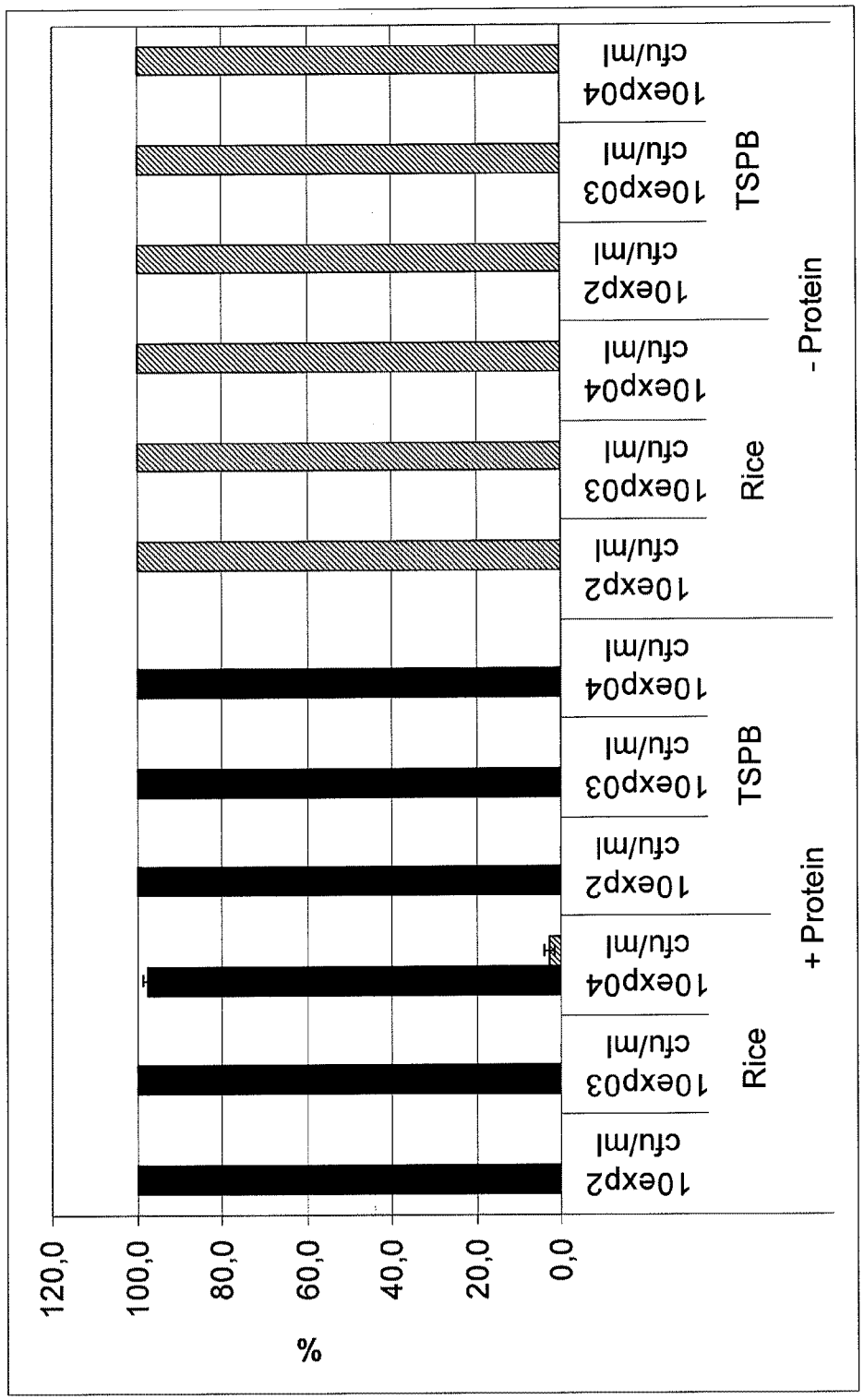

The appearance of pathogen germs from the Bacillus cereus group is a problem particularly concerning pre-cooked, highly carbohydrate containing foods like ready-to-eat products or re-warmed rice. For this reason, pre-cooked rice was used as a food sample which only needs to be heated for two minutes in the microwave oven to finish cooking. The food sample was diluted with medium and homogenised and spiked with Bacillus cereus cells in concentrations of $10^2$, $10^3$ or $10^4$ CFU/ml. TSPB-medium was used as a control. FIG. 13A illustrates the number of bound cells in percent of the recovered cells in the bead fraction (black bars) and in the supernatants (shaded bars). FIG. 13B exemplarily depicts a PEMBA-plate on which the bead fraction with the bound cells was plated. Bacillus cereus colonies can be recognized by their flower shaped and broadening growth. In comparison, FIG. 13C depicts a PEMBA-plate, on which supernatant fraction with the containing cells was plated.

Figure 14:
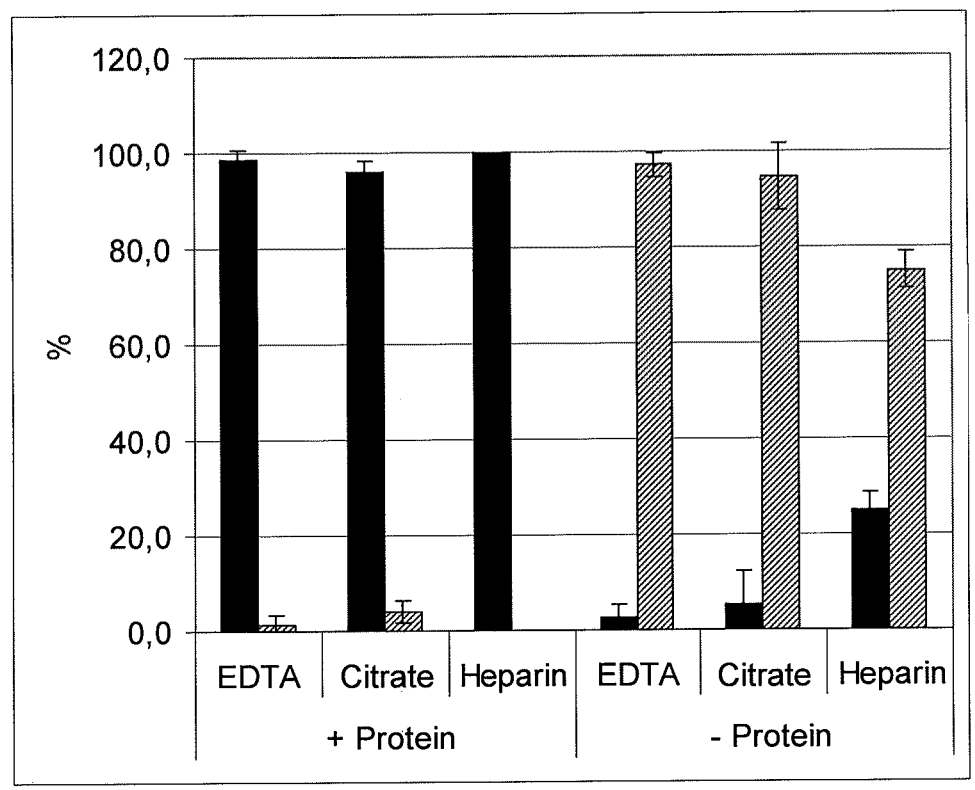

FIG. 14: Concentration of Bacillus cereus from blood with the help of CBD 21 and magnetic beads Human blood was spiked with Bacillus cereus (DSMZ345) in a concentration of $10^3$ CFU/ml. Citrate, EDTA or heparin were previously added to the blood samples to inhibit blood coagulation and diluted 1:1 with PBST-buffer. JS-tag-CBD21 (10 µg/ml) (black bars), controls without protein (shaded bars).

FIG. 15: Specific binding of Clostridium perfringens with JS-tag-CBD3626

The green fluorescence of the spacer GFP was herein used as a marker to visualize the binding of JS-tag-GFP-CBD3626 to the Clostridium bacteria and the magnetic beads, respectively. FIG. 15A exemplarily depicts the binding of JS-tag- GFP-CBD3626 to *Clostridium perfringens* cells. 15B exemplarily depicts the binding of JS-tag-GFP-CBD3626 to magnetic particles.

FIG. 16: Specific cell binding of different *Staphylococcus strains* by JS-tag-CBD-constructs according to the present invention measured in the cell binding test JS-tag-CBD-constructs according to the present invention JS-CBDPitti20 (grey bars), JS-CBDOpf (white bars) and JS-CBDUSA (black bars) were used. It is depicted how many percent of the introduced cells were specifically bound in the cell binding test. In experiment 20 the performance of the experiments is described. The given numbers are numbers from the PROFOS strain collection. The *Staphylococcus* strains are isolates from patients as well as DSMZ and ATCC strains, respectively.

FIG. 16A: Cell binding to different *Staphylococcus aureus* strains, divided in MRSA strains and non-MRSA strains.

FIG. 16B: Cell binding to different non-*Staphylococcus aureus* staphylococcal bacteria strains: C=*Staphylococcus carnosus*, D=*Staphylococcus epidermidis*, E=*Staphylococcus equorum*, F=*Staphylococcus haemolyticus*, G=*Staphylococcus saprophyticus*, H=*Staphylococcus sciuri*, I=*Staphylococcus simulans*, J=*Staphylococcus warneri*, K=*Staphylococcus xylosus.*

FIG. 17: Specific cell binding of different *Staphylococcus* strains by JS-tag-CBD-constructs according to the present invention in the peroxidase test The performance and the principal of the peroxidase test are described in experiment 21.

FIG. 17A depicts the specific binding of the JS-tag-constructs JS-CBDALE-1 (shaded bars) and JS-CBDLS (Lysostaphin) (white bars) two different *Staphylococcus* stains. The background absorption of a buffer control without addition of protein (black bars) is also depicted. The following *Staphylococcus* strains were used in the test: 5459—*S. aureus* (patient sample), S1546—*S. epidermidis* (DSMZ 20044), S1548—*S. haemolyticus* (DSMZ 20228), 5464—*S. aureus* (patient sample), S1501—*S. aureus* MRSA (patient sample), S1502—*S. aureus* MRSA (patient sample), S27 *S. haemolyticus*.

FIG. 17B depicts the specific binding of further *Staphylococcus* specific JS-tag-constructs to a set of *Staphylococcus* species as well as to an *E. coli* strain as unspecific control. Buffer control (black bar), JS-CBDALE-1 (shaded), JS-CBDLS (white), JS-CBDPitti20 (horizontal striped), JS-CBDOpf (grey), JS-CBDUSA (vertical striped). The following bacteria strains were introduced in the test: S683—*E. coli* (ECOR01), S1603—*Streptococcus mutans* (DSMZ 20523), S464—*S. aureus* (patient isolate), S1513—*S. aureus* (patient isolate), S1502—*S. aureus* MRSA (patient sample), S1501—*S. aureus* MRSA (patient sample), S27 *S. haemolyticus*.

FIG. 18: Specific cell binding in the peroxidase test by polypeptide constructs according to the present invention deriving from *Enterococcus* endolysins The performance of the test is described in experiment 22. Two JS-tag-CBD-constructs according to the present invention were introduced: JS-CBDEF0355 (grey bars) and JS-CBDEF1293 (white bars). The buffer control without addition of protein (black bars) is also depicted. The given numbers are strain numbers from the PROFOS strain collection. It is a matter of patient isolates as well as DSMZ and ATCC strains of the species *Enterococcus* and *Staphylococcus*.

FIG. 18A depicts the specific binding to different *Enterococcus faecalis* strains.

FIG. 18B depicts the specific binding to different *Enterococcus faecium* strains as well as to a *Staphylococcus aureus* strain.

The invention is described below.

The term "bacteria removal" as used herein means complete or partial removal of bacteria from the sample material.

The term "bacteria enrichment" as used herein means the concentration of the bacteria based on the initial concentration present in the sample. The enrichment has to be carried out generally such that a respective detection step allows an unambiguously positive or unambiguously negative conclusion.

The term "capture" of bacteria means the procedure of the extraction and binding of the bacteria from a sample with the help of the capability of the "CBDs" to specifically bind bacteria from the sample.

The term "sample material" or "sample" as used herein comprises all solutions in which bacteria should be detected or from which bacteria should be removed. Examples for suitable samples are: Aqueous solutions and mixtures of water and organic solvents, foods, media, blood, blood products, plasma, serum, urine, other body fluids, diagnostic samples, protein solutions, water ethanol mixtures, process solutions such as washing solutions for the analysis of the contamination of medical devices or in food processing. Furthermore, comprised are also solutions in which non-aqueous solid substances were solved, which are to be analysed or to be isolated, e.g. proteins, DNA, RNA, sugar, salts, foods, food-media homogenates, medicaments, vaccines, environmental samples, faeces, organic and inorganic chemicals, e.g. NaCl, $MgCl_2$, purine, pyrimidine.

The term "endolysin" as used herein means an enzyme, which serves in its original function for the release of new phages in the end of a respective phage reproduction cycle. Such an endolysin can be for example encoded by the phage genome in nature. These endolysins consist of at least one enzymatic active domain each and an enzymatic non-active domain bound to the cell wall of the respective host cell. Additionally, endolysin has to be understood to comprise also the similarly composed autolysins. These are bacteria encoded in nature and consist also of at least one enzymatic active cell wall hydrolysing domain and an enzymatic non-active domain binding to the cell wall of the target bacterium. Phage encoded endolysins and bacteria encoded autolysins are frequently homologous to each other (Garcia et al., 1988, Proc. Natl. Acad. Sci. USA, 85, 914-918) and the modules are exchangeable and can even be combined with each other in chimera from bacteria and phage encoded sequences (Diaz et al., 1990, Proc. Natl. Acad. Sci. USA, Vol. 87, 8125-8129). Therefore, besides the cell wall binding domains from phage endolysins also respective non-enzymatic active cell binding domains from other cell wall lysing enzymes can be used according to the present invention, e.g. autolysins, bacteriocines or phage tail proteins.

The term "CBD" as used herein means polypeptide-domains and -sequences, respectively, deriving from endolysins or other cell wall lysing enzymes and being responsible for the specific binding of the endolysins or the other cell wall lysing enzymes to the bacteria cell wall. These are enzymatically non-active.

The term "polypeptide according to the present invention" as used herein means a polypeptide comprising an enzymatically non-active cell wall binding domain of an endolysin or of another cell wall lysing enzyme (CBD) and a sequence according to SEQ ID NO:1 or derivatives thereof, wherein the polypeptide comprises besides the cell wall binding domain no further domains of an endolysin or another cell wall lysing enzyme, particularly no complete enzymatic active domain (EAD) of an endolysin.

The term "JS-tag" as used herein means a polypeptide sequence comprising a sequence according to SEQ ID NO:1 or derivatives thereof. The JS-tag derives from the biotin acceptor domain of the α-subunit of *Klebsiella pneumoniae* oxalacetate decarboxylase and contains the consensus sequence MKM (K is biotinylated) so that the polypeptide can be biotinylated in vivo by the protein biotin ligase. Compared to the complete α-subunit of *Klebsiella pneumoniae* oxalacetate decarboxylase the JS-tag is truncated. One possible minimal sequence for the JS-tag comprises 66 amino acids corresponding to amino acids 529 to 594 of the *Klebsiella pneumoniae* oxalacetate decarboxylase (SEQ ID NO:2). The term "JS-tag" also comprises derivatives of the sequence according to SEQ ID NO:1. Derivatives as used herein comprise such sequences still at least 80% homologous to SEQ ID NO:1. Examples for such derivatives are depicted in SEQ ID NO: 2-18.

The term "directed immobilisation" as used herein means that the CBDs are immobilised on suitable surfaces via biotin as specific coupling agent, e.g. via magnetic particles supplied with streptavidin or avidin or other carriers.

The term "surface" or "carrier" as used herein comprises all materials to which a coupling or adhesion of a CBD molecule and polypeptide according to the present invention, respectively, is possible directly or indirectly, e.g. to glass surfaces, to chromatography materials, such as agarose, sepharose, acrylate, to plastic surfaces such as polystyrene, polyethylene, polycarbonate, polypropylene, polysulfone, polymethyl methacrylate, to filter materials or membranes such as cellulose, cellulose acetate, nitrocellulose, PVDF, to magnetic or non-magnetic particles made of glass, latex, plastic, metal, metal oxide.

The term "1-step method" as used herein means a method, in which specific binding proteins, e.g. a polypeptide according to the present invention, were immobilized to a suitable carrier or a surface either directed or undirected already before adding the sample. After incubation of the immobilized binding proteins with the sample, the bacteria-binding protein-carrier-complex is separated from the sample and then optionally washed.

The term "2-step method" as used herein means a method, in which non-immobilized specific binding proteins, e.g. a polypeptide according to the present invention, are contacted and incubated with the sample. The formed bacteria-binding protein-complexes are subsequently contacted with a suitable carrier or a surface such that the bacteria-binding protein-complexes are bound via the binding proteins with the help of the biotinylated affinity tags to the carriers or surfaces. Subsequently, the bacteria-binding protein-carrier-complexes are separated from the sample and optionally washed. The binding proteins are modified with a polypeptide or a chemical group in a way that they bind specifically to a carrier or a surface supplied with the respective binding partner of the polypeptide or the chemical group.

The term "polypeptide" as used herein means a polypeptide chain of at least five amino acids.

The term "bacteria-polypeptide-complex" or "polypeptide-bacteria-complex" as used herein means a complex in which bacteria and the polypeptide according to the present invention (the polypeptides according to the present invention) are present.

The term "carrier-polypeptide-bacteria-complex" as used herein means a complex in which bacteria, the polypeptide according to the present invention (the polypeptides according to the present invention) as well as a carrier (-material) are present.

The present invention relates to a polypeptide comprising
i) an enzymatic non-active cell wall binding domain of an endolysin or another cell wall lysing enzyme (CBD), and
ii) a sequence according to SEQ ID NO:1 or a derivative thereof,
wherein the polypeptide comprises besides the cell wall binding domain no further domains of an endolysin or another cell wall lysing enzyme.

The present invention particularly relates to a polypeptide according to the present invention, which is biotinylated. In a particular embodiment, the cell wall binding domain of an endolysin or another cell wall lysing enzyme (CBD) within the polypeptide according to the present invention exhibits the capability to specifically bind gram-positive bacteria. The polypeptide according to the present invention is suitable to bind, enrich, remove from a sample, capture and/or detect bacteria.

The present invention therefore relates to the use of a polypeptide according to the present invention to bind, enrich, remove from a sample, capture and/or detect bacteria.

Thus, the present invention further relates to a method for the binding, the enrichment, the removal, the capture and/or the detection of bacteria from a sample comprising the steps:
a) contacting and/or incubating a sample with a biotinylated polypeptide according to the present invention,
b) contacting and/or incubating the polypeptide-bacteria-complex obtained in step a) with a carrier supplied with a biotin-binding substance.
c) separating the carrier-polypeptide-bacteria-complex obtained in step b) from the sample,
d) optionally washing unspecifically attached components of the sample from the carrier-polypeptide-bacteria-complex,
e) optionally separating the carrier from the polypeptide-bacteria-complex, and
f) optionally detecting the bacteria.

In the method according to the present invention the duration of the incubation of the sample with the respective polypeptides according to the present invention (step a) and the incubation of the bacteria-polypeptide-complex with the carrier material (step b), respectively, has to be adjusted to the respective sample and can vary in an embodiment between several seconds and about 24 h. Step a) of the method according to the present invention, in which the functionalized, i.e. biotinylated polypeptides according to the present invention bind to bacteria, is generally faster than step b), in which the biotinylated polypeptide-bacteria-complex is immobilized on the biotin-binding-carrier. Suitable incubation times for step a) of the method according to the present invention are particularly about 0.1 min to about 10 min, for step b) particularly about 10 min to about 60 min or if necessary also overnight. Whereas in step a) of the method according to the present invention it is generally enough to mix the added polypeptides according to the present invention and the sample thoroughly, it could be necessary during the incubation with the carrier material (step b), e.g. after adding carrier material, to roll the sample container in a lying position to achieve an as efficient as possible binding to the carrier.

At very low bacterial concentrations in the starting material a preincubation phase in a suitable nutrient medium is possibly necessary, to achieve an efficient enrichment and therefore obtaining a suitable sample for the method according to the present invention. Samples containing solid components such as food samples can be homogenised prior to the use in the method according to the present invention and taken up in suitable solutions before they are used in the method according to the present invention.

In the method according to the present invention a carrier is used, which is supplied with a biotin-binding substance, i.e. the carrier was functionalized. The biotin-binding substance should be capable to bind biotin with high affinity. Particularly suitable binding partners, i.e. biotin-binding substances, on the surface of the carriers are for example streptavidin, avidin and biotin-binding variants thereof such as monomeric avidin, avidin with partially acetylated amino groups or partially esterified carboxyl groups thereof. Hydrophilic surfaces are preferred compared to hydrophobic surfaces since they are generally more suitable to bind proteins and to tend to agglutination to a lesser extent.

The bacteria are enriched by separation of the bacteria from the rest of the sample. The bacteria can be enriched in the described method for example on a magnetic basis, via chromatographic methods or in the batch-method. Preferred is a magnetic enrichment since this method, compared to other methods, is very fast, can be miniaturized and also automated. But also the chromatographic method or the batch-method can be used, particularly if the method is primarily not used for the following bacteria detection, but is aiming, e.g. at the isolation of a larger amount of bacteria and to continue to work with these isolated bacteria.

During the enrichment on magnetic basis the polypeptide-bacteria-complexes are incubated with suitable magnetic particles as carrier in step b) of the method according to the present invention. The magnetic particles can exhibit diameters in certain embodiments in the range form about 0.1 µm to about 100 µm. However, preferred are smaller particles with a diameter between about 0.5 µm to about 5 µam, particularly preferred are particles with the diameter of about 0.8 µm to about 2 µm, since smaller particles sediment to a lesser extend and therefore providing a better mixture and exhibiting a relatively larger surface compared to larger particles as well as exhibiting high recovery rates. Examples for suitable magnetic particles are MagPrep-streptavidin particles (Merck), streptavidin-magnetic-particles (Roche), streptavidin-beads (Dynal), streptavidin coupled silica-beads (MicroCoat), streptavidin-coupled polyvinyl-alcohol-beads (PA-streptavidin-beads, Microcoat). After step b) of the method according to the present invention, the carrier-polypeptide-bacteria-complex is separated from the sample magnetically by applying a magnetic field. Suitable magnetic separators are available for example from the companies Ambion, Ademtech, Bilatec, BioLabs, Dynal, Polysciences and Promega.

During the enrichment with the help of the batch-method the bacteria containing sample is primarily incubated with the polypeptide according to the present invention, subsequently carrier material is added, suitable to bind high affinity biotin, mixed and again incubated together. Subsequently the carrier-polypeptide-bacteria-complex can be centrifuged from the sample, sedimented or filtrated. Preferred is the concentration via the batch-method particularly at very low bacteria concentrations.

Alternatively, the polypeptide-bacteria-complexes can be separated from the sample and enriched by applying them on a chromatography column containing biotin-binding column material.

The polypeptide-bacterial-complexes can be separated from the functionalized carrier by displacement, e.g. by adding an appropriate amount of biotin or by the adjustment of conditions, which highly denaturate proteins, such as about 8 M guanidinium chloride or about pH 1.5 and by adding biotinidase, cleaving biotin from the peptides, respectively. It is also possible that only the bacteria are separated from the biotinylated polypeptides according to the present invention by choosing conditions, at which the polypeptides according to the present invention do not bind to their receptor on the bacteria surface anymore. Since different polypeptides according to the present invention are used for the invention, the exact conditions therefore have to be tested in the individual case. This can for example be carried out by introducing a fluorescing marker and monitoring under the fluorescence microscope, wether the previously bound bacteria still fluoresce since their surface is covered with polypeptides according to the present invention. However, generally a change of the ion strength to a very high or a very low ion strength, a change of the pH to very acidic or basic, e.g. 50 mM sodium phosphate and pH 11 for 5 min, the addition of detergents or chemical denaturants such as urea or guanidinium chloride, or a combination of the mentioned possibilities are suitable to prevent the CBD bacteria-binding, since this is the specific protein-protein interaction. However, for a lot of applications, e.g. the subsequent plating and counting of the colonies deriving from the bound bacteria, a separation of the magnetic particles from the bacteria is not necessary at all.

The present invention further relates to methods for the detection of bacteria in a sample. The detection of bacteria comprises further steps subsequently to the above described method steps for enrichment. Depending on the kind of the bacteria, which should be detected, a set of techniques is known by a person skilled in the art, leading to the wished result. A choice of suitable detection methods is mentioned below. Bacteria can for example be detected in the complex together with the carrier and the biotinylated polypeptide according to the present invention or after releasing from the carrier material via selective growth conditions, e.g. plating and incubating on selective media plates. Furthermore, a detection of the bacteria is possible by nucleic acid based methods, i.e. detection of the nucleic acids of the bacteria, e.g. PCR, RT-PCR, PCR-RFLP, rep-PCR-fingerprinting, NASBA, DNA-hybridisation methods for example for certain toxins or other pathogenicity factors, multi-locus sequence typing (MLST), rRNA-comparisons. Further possible is a detection of the bacteria cell wall and their components, respectively, e.g. via cell binding domains of endolysins or antibodies or via FTIR, and the detection of bacteria components, respectively, e.g. proteins via ELISA or enzymes via their activity or multi-locus enzyme electrophoreses (MEE). The bacteria detection is also possible via ATP, which is contained in bacteria, e.g. in a bioluminescence assay via detection using a bacteria specific bacteriophage, e.g. for *listeria* A511-luxA, (see U.S. Pat. No. 5,824,468). The bacteria can further be detected in the carrier-polypeptide-bacteria-complex or after removal from the carrier material via another specific CBD coupled to a marker. A set of examples are therefore depicted in EP1147419. A conventional detection of a combination of microbiologic, morphologic and/or biochemical detection methods is also possible.

The detection of bacteria components, e.g. of proteins is preferably performed via ELISA or similar techniques (e.g. VIDAS). For the performance of these methods it is necessary to disrupt bacteria prior to the actual detection. This can for example be performed with a lysis protein such as lysozyme or a bacteria specific endolysin. Lyses proteins can for example be selected from the following group (references in brackets are either accession numbers for the NCBI-database (number-letter combination) or publication citations):

Ply511 (Q38653), Ply500 (Q37979), Ply118 (Q37976), PlyPSA (1XOV_A), the autolysin of strain EGDe (NP_466213) for *Listeria*, PlyL (1YB0_A, B and C), PlyG (YP_891193), PlyPH (Yoong et al., J. Bac. 2006, 188, 2711-2714), PlyB (2NW0_A and B) for *Bacillus anthracis*, PlyBa (CAA72266), Ply21 (CAA72267), Ply12 (CAA72264) for *Bacillus cereus*, Ply3626 (WO 03/066845) and the lysines from *Cl. perfringens* strain 13 (BAB81921) and strain SM101 (YP_699489) for *Clostridium perfringens*, ΦP1 Lysine (EP1300082) for *Clostridium tyrobutyricum*, PlyV12 (NP_049942) for *Enterococcus*, PlyC (NP_852017), PlyGBS (AAR99416), Cpl-1 (P15057), Cpl-7 (P19385), Cpl-9 (P19386), Pal Amidase from the Phage Dp1 (P19386), B30 Endolysin (AAN28166) and LytA (CAJ34420) for *Streptococcus*, Twort Amidase (CAA69021), *Staphylococcus* Phage P68 Amidase (NP_817332), LysK (O'Flaherty et al., J. Bac., 2005, 187, 7161-7164), ΦSA2usa Lysine (YP_494080), Phi11 Amidase (NP_803306) and cell wall hydrolase (NP_803302) or Phi12 Endolysin (NP_803355), as well as the autolysins Atl (BAA04185) from *Staphylococcus aureus*, AtlE (CAI59555) from *Staphylococcus epidermidis*, ALE-1 (BAA13069) from *Staphylococcus capitis* as well as from *Staphylococcus aureus* strain PS47 deriving from the peptidoglycan hydrolase (AAA26662) or Lysostaphin (AAB53783) from *Staphylococcus simulans* for *Staphylococcus*.

The cell lyses can be supported by different further additives such as the addition of proteases e.g. proteinase K and the use of heat, preferably 5 min at about 56° C., subsequently 5 min at about 94° C. or such as the addition of detergents, preferably triton, SDS, tween, Na-desoxycholate or solvents such as DMSO, isopropyl alcohol, ethanol, butanol, chloroform.

The polypeptides according to the present invention comprise polypeptide domains/-sequences of endolysins and autolysins, respectively, the so called CBDs, wherein the polypeptides according to the present invention do not exhibit enzymatic active cell wall hydrolysing regions anymore. The lack of the enzyme activity is necessary to functionally separate the bacteria in the complex with the carrier. A lysis of the bound bacteria and therefore a release of the cell contents preferably occurs purposely, only after the separation if this is necessary e.g. for the subsequent detection reaction. The polypeptides according to the present invention therefore comprise in a particular embodiment besides the cell wall binding domain no further domains of an endolysin, particularly no enzymatic-active domain (EAD) of an endolysin, and in particular embodiments also no further sequences of an endolysin. However, under certain conditions a minor hydrolytic rest activity of the used polypeptide fragments can be tolerable. However, this depends on the respective application, i.e. it has to be checked to what extent the rate of the cell hydrolases can be reconciled with the total duration of the application such that a sufficient amount of intact cells are captured. How a potential rest activity of the CBDs can be detected in a hydrolyse assay is for example described in Loessner et al. (1996, Appl. Environ. Microbiol. 62, 3057-3060).

The polypeptide according to the present invention exhibits in a particular embodiment derivatives of SEQ ID NO:1. Examples for such derivatives are depicted in SEQ ID NOs: 2-18, said examples exhibit the following as exemplified variation of SEQ ID NO:1:

i) compared to SEQ ID NO:1 at position 60 Asp instead of Glu,
ii) at the C-terminus an additional Val or Val-Asp, and/or
iii) at the N-terminus an additional M or MVGA.

The above mentioned derivatives of SEQ ID NO:1 turned out to be advantageous concerning the use in the method according to the present invention.

The modular organisation of endolysins in C-terminal domains (CBDs) responsible for the specific cell binding and N-terminal domains (EADs) including the enzymatic active centre were already described in 1990 by Garcia et al. (1990, Gene, 86, 81-88). The concept of the CBDs was continued in Loessner et al., 2002, (Mol. Microbiol., 44, 335-349) and Loessner, 2005, (Curr. Opin. Microbiol, 8, 480-487). A multitude of CBDs are already described in the state of the art. Frequently, the enzymatic active-domain (EAD) is located at the N-terminus and the CBD at the C-terminus—however, there are exceptions (e.g. Garcia et al., 1988, Proc. Natl. Acad. Sci. USA, 85, 914-918; Loessner, 2005, Curr. Op. Microbiol., 8, 480-487). The EAD is generally well defined and can be found and located relatively easy via sequence and homology comparisons with other hydrolases such as amidases, endopeptidases, glycosidases, transglycosylases, muramidases, with sequence analyses softwares, known in the state of the art, and respective databases with conserved sequence motives (e.g. CDD (Marchler-Bauer et al., 2005; Nucleic Acids Research, 33, D192-D196); Pfam (Finn et al., 2006, Nucleic Acids Research 34, D247-D251) or SMART (Schultz et al., 1998, Proc. Natl. Acad. Sci. USA 95, 5857-5864, Letunic et al., 2006, Nucleic Acids Res 34, D257-D260)). During the identification of the CBD part of endolysins, already known motives for cell binding domains in many cases are found, providing a sound indication for the provision of the CBD sequence for the polypeptides according to the present invention. In the group of endolysins, which bind to streptococci, the CBD is relatively easy to find since mostly about 20 amino acids long choline-binding-motives with conserved aromatic residues (CW_binding_1, pfam01473) appear, which occur frequently in multiple repeats (see Garcia et al., 1990, Gene, 86, 81-88). The about 40 amino acids long LysM domain (pfam01476) can also be partially found in CBDs. This is a widely spread peptidoglycan-binding-module with conserved secondary structure (Bateman & Bycroft, 2000, J. Mol. Biol., 299, 1113-1119). SH3b-domains and SH3_3, SH3_4 or SH3_5 domains (smart00287, pfam08239, pfam06347, pfam08460), respectively, the prokaryotic counterparts to the eukaryotic and viral Scr homology domains, SH3, (Ponting et al, 1999, J. Mol. Biol., 289, 729-745) can also often be found as cell binding motives and CBDs, mainly in staphylococci and enterococci. The peptidoglycan-binding-domain (PG_binding_1, pfam01471; PG binding 2, pfam08823) consists of 3 helices which can be found frequently also N-terminal of the EAD. However, sometimes no direct relationship of the CBD portions to other related bacteriophage endolysins or also to other carbohydrate binding proteins can be found and unique sequence motives or structure modules can barely be defined indicating a CBD. In such cases, the relationship can be determined via the EAD. As a basis for the polypeptide according to the present invention serves in this cases, besides the CBDs known from the state of the art, the portion of an endolysin, which is not occupied by the EAD. The rest of this endolysin (i.e. endolysin minus EAD) can directly be understood and used as CBD, as far as it exhibits cell binding function. However, it can be useful in some embodiments of the present invention to use shorter fragments (e.g. because they exhibit a higher stability) as far as they still exhibit cell binding function. The functional test for a CBD is the detection of the cell binding to the respective bacteria. Different exemplified assays suitable for that purpose are described in the experiments and figures. Besides an efficient cell binding, the expression rate, solubility, stability and simple purification are further features which should be taken into account concerning the definition of the peptide portion functioning as CBD. Methods to test these features are known from the state of the art by the person skilled in the art. Some examples are therefore also described below in the experiments. Purposely planned CBD portions are for example orientated according to structural standards, which can be assessed by the person skilled in the art on the basis of secondary structure predictions, potential domain linkers and 3D-models. Suitable exemplified methods are for example described in the following publications: Garnier et al., 1996, Methods in Enzymology 266, 540-553; Miyazaki et al., 2002, J. Struct. Funct. Genomics, 15, 37-51; Altschul et al., 1997, Nucleic Acids Res. 17, 3389-3402; Schwede et al., 2003, Nucleic Acids Research 31, 3381-3385. Lund et al, CPHmodels 2.0: X3M a Computer Program to Extract 3D Models. Abstract at the CASP5 conference A102, 2002.

Basically all CBDs known from the state of the art and all CBDs deriving from endolysins according, to the above described method can be used for the polypeptides according to the present invention and in the method according to the present invention.

In a particular embodiment of the invention the cell wall-binding domain of the peptide according to the present invention is selected from the group of cell wall binding domains of the following endolysins and other cell wall lysing enzymes, respectively, consisting of Ply511 (Q38653), Ply 500 (Q37979), Ply 118 (Q37976), PlyPSA (1XOV_A), EGDe (NP_466213), PLyL (1YB0_A, B and C), PlyG (YP_891193), PlyPH (Yoong et al., J. Bac. 2006, 188, 2711-2714), PlyB (2NW0_A and B), PlyBa (CAA72266), Ply21 (CAA72267), Ply12 (CAA72264), of the *Enterococcus faecalis* V583 prophage endolysins, Ply3626 (WO 03/066845), lysins from *Cl. perfringens* strain 13 (BAB81921) and strain SM101 (YP_699489), ΦP1 lysin (EP1300082), PlyV12 (NP_049942), PlyC (NP_852017), PlyGBS (AAR99416), Cpl-1 (P15057), Cpl-7 (P19385), Cpl-9 (P19386), Pal Amidase (P19386), Twort Amidase (CAA69021), *S. aureus* phage PVL amidase (UniProt 080064), P68 lys16 (NP_817332), ΦSA2usa endolysin (YP_494080), Phi11 (NP_803306) and Phi12 Endolysin (NP_803355), cell wall hydrolyses of the *Staphylococcus aureus* phage Phi 11 (NP_803302), phage B30 endolysin (AAN28166), phage 168 endolysin (M J Loessner et al., J Bacteriol. 1997 May; 179(9): 2845-2851), LysK (O'Flaherty et al., J. Bac., 2005, 187, 7161-7164), *S. simulans* Lysostaphin (AAB53783), *S. capitis* ALE-1 endopeptidase (BAA13069), phage PhiNIH1.1 cell wall hydrolase (NP_438163), LytM (AAB62278), Atl (BAA04185), LytA from *Streptococcus pneumoniae* (CAJ34420), from *Staphylococcus aureus* strain PS47 deriving from peptidoglycan hydrolase (AAA26662), enterolysin A from *Enterococcus faecalis* (Q9F8B0), ami autolysin from *L. monocytogenes* (Milohanic et al.; Infection and Immunity, August 2004, p. 4401-4409, Vol. 72, No. 8), lactobacillus lysin, e.g. lysin of the phage A2 (AJ251788.2 or Q9MCC8), phage. PL-1 amidase (Q9MCC6) (both *L. casei*) etc.

Particularly suitable for the binding of *listeria* are fragments of the endolysin Ply511, for the binding of *bacillus* fragments of the endolysins PlyBa, Ply21, and Ply12, for the binding of *clostridium* fragments of Ply2636, for the binding of staphylococci fragments of the ΦSA2usa endolysins, of the *Staphylococcus* bacteriocine lysostaphin, of the lysostaphin like ALE-1, of the *staphylococcus* self-isolated plyOpf, plyPitti20, plyPitti26 and similar proteins of homologous prophages and for the binding of enterococci fragments from endolysins of the prophage from *Enterococcus faecalis* V583 as well as CBDEF0355 and CBDEF129.

Examples for CBD sequences which can appear in the polypeptides according to the present invention are:

```
SEQ ID NO: 19: CBD21;
SEQ ID NO: 20: CBDBA
SEQ ID NO: 21: CBDUSA
SEQ ID NO: 22: Ply511 Version 1
SEQ ID NO: 23: Ply511 Version 2
SEQ ID NO: 24: Ply511 Version 3
SEQ ID NO: 25: Ply3626 Version 1
SEQ ID NO: 26: Ply3626 Version 2
SEQ ID NO: 27: CBDPitti20
SEQ ID NO: 28: CBDPitti26
SEQ ID NO: 29: CBDLS
SEQ ID NO: 30: CBDALE-1
SEQ ID NO: 31: CBDOpf
SEQ ID NO: 32: CBDEF0355
SEQ ID NO: 33: CBDEF1293
```

In a particular embodiment the polypeptide according to the present invention comprises no further sequences of an endolysin besides the cell-wall binding domain. The polypeptide according to the present invention preferably consists of only one CBD and an additional polypeptide sequence according to SEQ ID NO:1 or derivatives thereof, optionally coupled by a linker or spacer.

The person skilled in the art exhibits knowledge about the sequences and structures of domain linker sequences and about their prediction (e.g. George and Heringa, 2003, Protein Eng. 15, 871-879; Bae et al., 2005, Bioinformatics, 21, 2264-2270), respectively. Domain linker sequences are frequently characterized by a relatively high portion of hydrophilic amino acids since they are generally less structured and exposed to solvents such as the short linker sequence AAKNPN (SEQ ID NO: 37) of the *listeria* endolysin PlyPSA (Korndorfer et al., 2006, J. Mol. Biol., 364, 678-689). Polyglycine linkers are also used traditionally, however, they are often protease sensitive. A special kind of the hydrophilic unstructured linkers is proline and threonine rich sequences also occurring as natural linkers, e.g. TPTPPNPGPKNFTT from Enterolysin A (SEQ ID NO: 36). Proline and threonine rich linker sequences can simply be described by the consensus motive $(PT)_xP$ or $(PT)_xT$ wherein x is an integer from 1 to 10. Croux et al. (1993, Molec. Microbiol., 9, 1019-1025) describe so-called junction zones between the N- and C-terminal domains, and thus the EADs and CBDs of the endolysins. These mostly relatively short areas are natural linker sequences and are also suitable to link the CBD modules recombinant to the JS-tags with the help of suitable cutting sites to a polypeptide according to the present invention. Particularly suitable examples for specific linkers are depicted, e.g. in SEQ ID NO: 34-38.

The sequence of a polypeptide according to the present invention can be composed as follows:
i) a sequence for a JS-tag selected from SEQ ID NO: 1-18,
ii) a sequence for a CBD selected from SEQ ID NO: 19-33,
iii) a linker sequence selected from SEQ ID NO: 34-38, and optionally
iv) as spacer a sequence for GFP, GST or MBP.

Several exemplified sequences for polypeptides according to the present invention are depicted in SEQ ID NO: 39-53.

The invention further relates to a non-enzymatic active cell wall binding domain, namely the CBD of Ply21. Surprisingly the hydrolytic non-active CBD21 exhibits a host-spectrum concerning bacteria binding, which comprises, besides almost all bacteria of the *bacillus* group (except for *B. polymyxa* and *B. sphaericus*), also further representatives from important groups of gram-positive bacteria such as staphylococci, enterococci, streptococci and even *listeria*. Since CBDs usually exhibit a relatively small host spectrum (Loessner 2005, Curr. Opin. Microbiol, 8, 480-487), this feature of broad host specificity for a CBD is very unusual. Therefore, the CBD21 is capable to bind all tested bacteria from the *bacillus cereus* group and additionally solve the object to generally enrich gram-positive bacteria, especially those deriving from groups, in which a lot of pathogen germs can be found such as staphylococci, streptococci, enterococci, micrococci, bacilli and *listeria*. In another aspect, the present invention therefore relates to a polypeptide comprising the sequence as depicted in SEQ ID NO: 19, but besides this cell wall binding domain does not comprise further domains of an endolysin. The polypeptide preferably comprises no complete enzymatic active domain of an endolysin. More preferably, the polypeptide comprising the sequence as depicted in SEQ ID NO: 19, does not comprise further sequences of an endolysin.

Due to the broad applicability of the CBD21, the present invention relates also to the use of the CBD21 according to the present invention comprising the sequence according to SEQ ID NO:19, but besides this cell wall binding domain does not comprise further domains of an endolysin, to bind, enrich, remove from a sample, capture and/or detect bacteria selected from the group consisting of staphylococci, streptococci, enterococci, micrococci, bacilli and/or *listeria* (see table 3).

The polypeptide portion of the polypeptides according to the present invention defining a suitable CBD can additionally be linked to a polypeptide portion, serving as spacer and optionally as marker at the same time. Since CBDs represent regions from bigger proteins, the endolysins, they are generally relatively small with about 100 to 300 amino acids or for certain cell binding motives even less. Therefore, it can be useful in a preferred embodiment to introduce a spacer between the CBD domain and the group responsible for the immobilisation to the carrier. This can prevent that the CBD is denatured by the immobilisation and that it looses its binding capability to the cells. For the binding of the polypeptide-bacteria-complex in the 2-step-method it can be important that the groups responsible for the immobilisation to the surfaces become better accessible if they are not directly coupled to the CBD. The spacer is preferably a well defined, well expressible stable protein module, which interacts with other proteins and surfaces as less as possible (e.g. GFP (green fluorescent protein), MBP (maltose binding protein), GST (glutathione s-transferase)). A particularly suitable example is GFP and variants thereof. Since GFP is highly fluorescing, it is also suitable as a marker. For this reason the polypeptide according to the present invention can be for example monitored during the method. In the functional test, i.e. binding test, a binding of the CBDs and of the polypeptides according to the present invention to the bacteria as well as a binding to the carrier can easily be detected. Further modifications can also serve as a marker, as for example proposed in EP 1147419.

To turn the CBD into the polypeptide according to the present invention the CBD has to be present with a tag, the so-called JS-tag, within a fusion protein. The extremely strong bond between biotin and its binding partner streptavidin and avidin ($10^{-15}$ M; Gonzales et al., 1997, J. Biol. Chem., 272, 11288-11294), respectively, is advantageous for the functioning of the above mentioned 2-step-method, which turns out to be even better compared to the known 1-step-method, known from the state of the art (e.g. EP1147419). Other tags also suitable to bind proteins to functionalized surfaces are for example the his-tag or the strep-tag (His-Tag $10^{-6}$-$10^{-8}$ M; Nieba et al., 1997, Anal. Biochem., 252, 217-228; Strep-Tag ~$10^{-6}$ M, Voss & Skerra, 1997, Protein Eng., 10, 975-982). The binding of the bacteria-polypeptide-complex to the carrier is more efficient in the 2-step-method which affects the binding time as well as results in a lower possible loss of bacteria under difficult conditions, e.g. in food samples, as well as in a higher sensitivity. In a choice of possible biotinylated coupling groups, the JS-tag is proofed to be more preferred. A chemical biotinylation does on the one hand not lead to a defined biotinylation at a certain position, with which a directed immobilisation of the CBDs to the carrier would be possible, which is wished for the functionality of the binding proteins. On the other hand proteins are thereby often inactivated. This can particularly apply to the relatively small protein domains of the CBDs. The Avi-tag, representing something like a minimal sequence, wherein the minimal sequence is still to be biotinylated in fusion proteins in vivo, turned out to be also less suitable compared to the JS-tag since higher protein amounts had to be introduced, to achieve an efficient binding of the bacteria to the magnetic beads. The biotinylation domains proposed in U.S. Pat. No. 5,252,466 for the fusion with proteins are relatively big compared to the Avi-tags. Thus, the biotinylation domain of the *Klebsielle pneumoniae* oxalacetate decarboxylase for example comprises 595 amino acids, which is disadvantageous concerning both the expression yield and insofar that the large fusion portion is relatively protease sensitive and therefore relatively unstable.

The JS-tag and derivatives thereof turn out to be very good biotinylation tags in combination with CBDs to bind, enrich, remove, capture and detect bacteria in samples. These are segments from the α-subunit of the *Klebsiella pneumoniae* oxalacetate decarboxylase and derivatives thereof containing the consensus motive (MKM) for the in vivo biotinylation. The polypeptide became more stable, e.g. towards proteolyses, compared to the complete biotinylation domain and is easier to handle as affinity tag, e.g. in cloning, expression and purification. The minimal sequence for the JS-tag is 66 amino acids long, which correspond to the amino acids 529 to 594 of the *Klebsiella pneumoniae* oxalacetate decarboxylase plus methionine as a start. Particularly suitable are sequences described under SEQ ID NO:1-18. In Cronan (1990, J. Biol. Chem., 265, 10327-10333) it is emphasized that conserved proline and alanine rich regions located N-terminal of the MKM motive should take important structural function for the biotinylation of the lysin by the biotin ligase. This region of the α-subunit of the *Klebsiella pneumoniae* oxalacetate decarboxylase is even particularly developed with a 22 amino acid long region of P and A. However, it turned out that this region is not necessary for the biotinylation in the described system since the above mentioned minimal sequence does not contain this region and is yet very efficiently biotinylated. It turned out that additionally to the amino acids 529 to 594 of the *Klebsiella pneumoniae* oxalacetate decarboxylase very short peptides (MVGA) provide a very good N-terminal starting sequence (see SEQ ID NO:8-10 and 16-18).

The fusion between the JS-tag and the CBD, and an additional intermediately introduced spacer module, respectively, can be carried out N-terminally as well as C-terminally of the CBD. Concerning the polypeptides according to the present invention the N-terminal fusion is preferred since the CBD portion of the endolysin is usually located C-terminal and the JS-tag (optionally plus spacer module) can structurally substitute the missing EAD of the endolysin. Since the biotinylation domains in proteins, which are biotinylated in vivo, are almost only located at the C-terminus, it is not obvious that these also function well if used N-terminally. For this reason, in Cronan (1990, J. Biol. Chem., 265, 10327-10333) only C-terminal fusions of proteins with a biotinylation domain of the 1.3 S subunit of the *Propionibacterium shermanii* transcarboxylase were used. If no spacer molecule is used, the JS-tag can be linked to the CBD via a linker (embodiment see above) or also without linker such that only one to three amino acids are introduced to obtain a restriction cutting site for cloning. The sequence AGAGAGAGS or AGAGAGAGSEL (SEQ ID NO:34 or 35) turned out to be an exemplified suitable linker peptide. However, other linker sequences of proteins with a known structure are linker sequences for relatively unstructured peptides (e.g. proline and threonine rich linkers such as $(PT)_3T(PT)_3T(PT)_3$) can also be used. An example for a PT-rich linker is TPTPPNPGPKNFTT (SEQ ID NO:36). An example for a (short) hydrophilic linker is AAKNPN (SEQ ID NO:37). Another example for a linker which can be used in the present invention is AGAGAGAEL (SEQ ID NO:38).

The polypeptide according to the present invention for the use in the method according to the present invention can be biotinylated thereby that it is biotinylated in vitro with the help of a biotin ligase under conditions known by the person skilled in the art. Surprisingly, it also turned out that compared to the invention described in U.S. Pat. No. 5,252,466 a coexpression of the biotinylated fusion protein with the biotin ligase (BirA) is not necessary in the preparation of the biotinylated polypeptides according to the present invention in bacteria cells, since the biotinylation also works in the absence of external biotin ligase. Interestingly, in complete medium such as LB not even the addition of biotin to the medium is necessary. Fusion proteins of JS-tag and CBD are efficiently biotinylated in commercially available *E. coli* expression strains, e.g. BL21 (DE3), HMS174 (DE3), JM83 without the additional coexpression of BirA or even without addition of biotin. In contrast to the proposed use of the biotinylation tags in U.S. Pat. No. 5,525,466 as means for an easier purification of proteins it is not necessary to purify the herein described fusions of JS-tag and CBD via affinity columns for biotin, but can be purified in a conventional way such as via cation or anion exchange chromatography, hydrophobic chromatography, fractionated ammonium sulphate precipitation, etc. On the one hand, this is of advantage since the respective affinity material for biotin is very expensive and regularly exhibits only a low capacity, e.g. chromatography material which carries streptavidin or streptactin coupled, on the other hand the fusion proteins are difficult to release from the affinity material since the binding between biotin and its binding partners is very efficient. This leads to problems in the described purification method. Thus, the target protein is eluted delayed from the column ("smears") and possibly denatured during elution.

The stability of the constructs according to the present invention depends to a certain extent on the specific features of the used CBDs. The fusion constructs consisting of JS-tag, CBD and optionally linker, spacer and marker, respectively, as well as the functionalized carrier such as magnetic beads can be stored over a longer period of time without loosing their binding capability. Storage is possible in a temperature range from about −20° C. to about 37° C. Preferred is storage at temperatures of about −20° C. to about 10° C. Regularly storage should be carried out nearly neutral pH values (pH 6-7), but storage at pH-values up to pH 10 is also possible if admitted by the CBD portion. Suitable buffer systems for the storage are e.g. 100 mM sodium phosphate buffer, pH 6 to pH 10, 2 mM EDTA or 10 mM imidazol, 100 mM NaCl, pH 7. The addition of generally stabilizing agents such as glycerol or ammonium sulphate with for example 30% of saturation has a positive effect on the storage capability.

With the method according to the present invention under use of the polypeptide constructs according to the present invention basically all gram-positive bacteria such as clostridii, bacilli, *listeria*, staphylococci, lactobacilli, enterococci, aerococci, pediococci, streptococci, mycoplasma, leuconostoc bind and can therefore be enriched, captured, immobilized and optionally detected. The mode of application depends on the mode of the used samples, as defined above. Particularly suitable is the method to enrich and detect potentially pathogen bacteria from food samples. However, the method is also suitable to enrich and detect pathogen bacteria from medical or diagnostic samples. Furthermore, it is suitable to remove or detect gram-positive bacteria from samples, in which they are undesired for example in pharmaceutical or cosmetic preparations and process solutions. The method according to the present invention safes a lot of time concerning the enrichment in contrast to conventional enrichment methods such as ISO-methods. In combination with a magnetic separation using functionalized magnetic particles for capturing the bacteria-polypeptide-complexes separation methods can be substituted, which are complex and difficult to automatise, e.g. centrifugation steps.

The invention further relates to nucleic acids as well as vectors encoding for the polypeptides according to the present invention as well as cells expressing the nucleic acids and vectors, respectively. The person skilled in the art is able to prepare suitable nucleic acids and vectors encoding for the polypeptides according to the present invention with procedures known in the state of the art. Amino acid sequences of the polypeptides according to the present invention can for example be derived from suitable nucleic acid sequences based on the genetic code. An optimized use of codons can here optionally be considered depending on the chosen expression system. The person skilled in the art is also able to choose suitable vectors, e.g. to ensure the expression of the polypeptides according to the present invention via the above mentioned nucleic acid.

Surprisingly it turned out that the nucleic acid sequence in the N-terminal part of the JS-tag of the translated polypeptide sequence is important for an effective expression. AT-rich sequences showed a significantly more efficient expression compared to GC-rich sequences under maintenance of the amino acid sequence. It is assumed that the development of secondary structure elements at the beginning of the transcribed RNA influences the efficiency of the translation. Three variants (SEQ ID NO: 54 to 56) of these AT-rich sequences turned out to be particularly suitable for fusions between JS-tag and a subsequent CBD (see table 1). Therefore, in a preferred embodiment the part of the sequence of the nucleic acid encoding for the JS-tag in the polypeptides according to the present invention starts with a sequence selected from SEQ ID NO:54 to 56.

The method according to the present invention and the polypeptide fragments according to the present invention, respectively, are characterized by the following advantages:
- A fusion with the JS-tag in combination with CBDs of endolysins is generally suitable to fast and efficiently bind gram-positive bacteria.
- A fusion of CBD and JS-tag is very suitable to enrich bacteria in an efficient 2-step-method, since biotin as coupling group allows a very good immobilization of the CBD bacteria complexes.
- The 2-step-method in combination with the fusion of CBD and JS-tag allows a smaller input of carrier material and mainly of specific binding protein, which is economically advantageous. The biotinylation in this method is very efficient and exactly defined such that in comparison to other methods an extremely high portion of functional binding protein is available. The binding of bacteria to free binding protein is also much more efficient compared to binding protein, which was prior immobilised on surfaces, where frequently steric problems, unspecific binding as a side reaction and non-functional immobilisation occur.
- The method according to the present invention is also suitable to immobilize different CBD bacteria complexes with one and the same carrier.
- The fusion of CBD and JS-tag turns out to be a construction of high stability, particularly characterized by long term stability at temperatures of up to about 30° C. and protease stability.
- The JS-tag has a length, which is good to handle because on the one hand it is not too long but on the other hand it is long enough so that no spacer is necessary.
- The method according to the present invention for the preparation of a polypeptide according to the present invention is functioning even without the coexpression of BirA.

The present invention further relates to a kit comprising a carrier supplied with a biotin binding substance such as streptavidin or avidin as functional groups, further comprising at least one variant of the polypeptide fragments according to the present invention having a CBD fused with JS-tag as well as the buffer solutions, e.g. washing buffer, elution buffer and/or lyses buffer, necessary for the enrichment and optionally the detection of gram-positive bacteria.

The following examples illustrate the invention and are not to be considered to be limiting. Unless otherwise indicated, molecular biological standard methods were used as described for example in Sambrook et al., 1989, Molecular cloning: A Laboratory Manual 2. Edition, Cold Spring Harbor Laboratory Press, Cold Spring Harbor, New York.

Experiment 1: Expression, Solubility and Functional Assembly of Phage Tail Proteins with Biotinylation Tags The result of the experiment is depicted in FIG. 1. The phage tail proteins from *salmonella* or *campylobacter* phages, mentioned in FIG. 1, were cloned according to standard methods in pET21a or pET21d and expressed at 30° C. in the given expression strains after IPTG-induction (1 ml per approach). After 3 to 4 hours, the cells were centrifuged (table centrifuge, 5 min, 13.000 rpm) and the pellets solved in buffer (e.g. 20 mM tris, 5 mM EDTA, pH 8). The cells were lysed using ultrasound and again centrifuged (20 min, 13.000 rpm, 4° C.). The supernatants containing the soluble protein were taken and either boiled for 5 min or not-boiled. Within the not-boiled samples SDS-resistant native trimers should form, which could be found at higher molecular weights. The pellets containing the insoluble protein were resuspended in the same volume of buffer (e.g. 20 mM Tris, pH 9, 50 mM NaCl, 5 mM EDTA). Lämmli-sample buffer was added to all samples and the samples were loaded on 12% and 9% SDS-polyacrylamide gels, respectively, and stained with Coomassie.

It has been shown in all three sub-experiments that no efficient amount of functional protein can be obtained with phage tail proteins having specific biotinylation tags. Partially, the expression rate is very poor, partially a major part of the proteins are insoluble and it is not possible to obtain a high portion of native protein, characterized by SDS-resistant, oligomeric forms. Only concerning the P22 similar phage tail protein, bands of monomers and native trimers could be detected on SDS gels. Concerning the other two proteins only very weak monomeric bands could be detected on western-blots such that the position could be localized and the basic functioning of induction and expression could be verified.

Experiment 2: Chemical Biotinylation of CBDs

Stock solutions of 1 mg/ml each of CBD511 (in PBS; 20 mM sodium phosphate pH 7.4, 120 mM sodium chloride) and NHS-biotin (in DMSO) were prepared. 120 µl NHS-biotin solution was added to 1200 µl protein solution and mixed thoroughly. 300 µl of each sample was taken immediately (0 min value) or after 20 min, 60 min or 120 min and added on ice to 30 µl 1 M tris, pH 8 to stop the reaction. All samples were dialysed against PBS-buffer. The protein concentration was determined of all samples by measuring the absorption and the degree of biotinylation was determined using the HABA-test. The degree of biotinylation was 1.5 to 2.5 biotin molecules per CBD-molecule. The cell binding test was performed with the strain *Listeria monocytogenes* Scott A, introduced in 500 µl of test sample (buffer PBST; 20 mM sodium phosphate pH 7.4, 120 mM sodium chloride, 0.1% tween 20) in a concentration of $10^4$ CFU/ml. Subsequently, biotinylated CBD511 was added in the concentrations 0.5 µg/ml, 1 µg/ml, 2 µg/ml and 5 µg/ml, respectively and incubated for 1 min. JS-tag CBD511 served as control. MagPrep-streptavidin particles (Merck) were added to 50 µg/ml and the samples were incubated for 20 min at room temperature in an overhead rolator. After 5 min of magnetic separation the supernatant was taken and the magnetic particles were washed once with 500 µl of PBST-buffer (10 min). After a second magnetic separation, the magnetic particles were added in one buffer volume and plated on oxford-plates (undiluted and diluted 1:10). As a control the pooled supernatants after the 1. and 2. magnetic separation were plated and counted after one night. The experiment is depicted in FIG. 2. It could be seen that all CBDs become inactive by the chemical biotinylation, whereas the cell binding test with the CBD specifically biotinylated by the JS-tag functions regularly.

Experiment 3a: Detection of *Listeria* in Camembert with the 1-Step-, 2-Step- and the ISO-Method 300 g of camembert from a supermarket were divided sterile in portion units of 25 g and stored in Stomacher bags at −80° C. One portion unit was analysed concerning the presence of *listeria* according to regulation ISO: 11290-1:1996 FDAM 1. If no *listeria* contamination could be detected, 5 portion units were thawed at room temperature and infected with different amounts of *L. monocytogenes* ScottA. Therefore an overnight culture was diluted 1 to 5 and incubated up to an $OD_{600}$ of about 1 at 37° C. Subsequently serial dilutions were prepared in sterile PBST (20 mM sodium phosphate pH 7.4, 120 mM sodium chloride, 0.05% tween). The portion units were contaminated with 0, 1-10, 11-50, 50-100 and 100-500 CFU/25 g camembert and stored overnight at 4° C. For accurate determination of the cell numbers, duplicates of the dilutions were plated on Oxford Agar (Profos AG), the plates incubated for 24 h at 37° C. and counted. 225 ml Fraser ½ medium (Profos AG) were added sterile to the portion units, homogenised for 1 min in the Stomacher and incubated at 30° C. After incubation time of 4 h, 6 h and 24 h, one ml of each sample was taken.

1-step-method: 300 µg/ml of magnetic particles (Dynabeads Epoxy) coated with Strep-tag-CBD511_f2 were added to 1 ml of homogenate and the sample was incubated for 20 min in an overhead rolator at room temperature.

2-step-method: 5 µg of Strep-tag-GFP-CBD511_f2 fusion protein was added to 1 ml homogenate and mixed shortly. Subsequently MagPrep-Streptavidin particles (Merck) were added to 50 µg/ml and the samples were incubated for 20 min in the overhead rolator at room temperature.

The particle-*listeria*-complexes were subsequently collected in a magnetic field at the vessel wall and the supernatant was removed. The particle-*listeria*-complex was washed 3× in 1 ml PBST (20 mM sodium phosphate pH 7.4, 120 mM sodium chloride, 0.05% tween) for 10 min in the overhead rollator, collected in the magnetic field at the vessel wall and each supernatant discarded. The particle-*listeria*-complexes were resuspended in 100 µl PBST and plated on Oxford-Agar (Profos AG). After 24 h and 48 h at 37° C. the plates were counted and the portion of the *listeria* attached to the magnetic particles was calculated in percent of the introduced cells. In parallel the contaminated samples were analysed concerning *listeria* according to the rule ISO: 11290-1:1996 FDAM 1. Therefore, 100 µl were added to 10 ml of Fraser medium (Profos AG) at the given time points, 24 h at 37° C. incubated in the rolator and subsequently plated on Oxford-Agar (Profos AG). All samples were performed in quadruplets.

It has been shown that with the 1-step-method as well as the 2-step-method the necessary concentration times are significantly shorter compared to the method according to ISO: 11290-1:1996 to detect minor *listeria* contamination in camembert. Concerning the shorter enrichment time, the results of the two-step-method is better compared to the 1-step-method.

Experiment 3b: Detection of *Listeria* from Mozzarella 225 ml FDA-medium was added to each of the 25 g of mozzarella and the portions were sterile homogenized in Stomacher bags. The samples were incubated over night at 30° C. *Listeria* of the strains EGDe (serotype 1/2a) and ScottA (serotype 4b) were added in a concentration of 500 CFU/ml. Prior to the *listeria* detection the samples were buffered each with 1/10 volumes of PBST.

1-step method: 300 µg/ml of magnetic particles (Dynabeads M270 Epoxy) coated with JS-tag-GFP-CBD511_f3 was added to 1 ml homogenate and the sample was incubated for 20 min in an overhead-rolator at room temperature.

2-step method: 0.5, 2, 5 or 10 µg of the JS-tag-GFP-CBD511_f3 fusion protein was added to 1 ml homogenate and mixed briefly. Subsequently, MagPrep-streptavidin particles (Merck) were added to 50 µg/ml and the samples were incubated for 20 min in an overhead-rolator at room temperature.

The particle-*listeria*-complexes were subsequently collected in a magnetic field at the vessel wall and the supernatant was removed. The particle-*listeria*-complex was washed 1× in 1 ml PBST for 10 min in the overhead rollator, collected in the magnetic field at the vessel wall and each supernatant discarded. The particle-*listeria*-complexes were resuspended in 100 µl PBST and plated on Oxford-Agar (Profos AG). After 24 h at 37° C. the plates were counted and the portion of the *listeria* attached to the magnetic particles was calculated in percent of the introduced cells.

All approaches were performed twice.

It has been shown that with the help of the JS-tag-GFP-CBD511_f3 fusion protein, *listeria* can be isolated from foods. Concerning mozzarella, this works significantly better with the strain EGDe than with ScottA. Slightly higher concentrations of protein should be used in foods to achieve a high binding efficiency.

Experiment 4: Cell Binding Capacity of JS-Tag-CBDs

Experiment 4a: Comparison of the Cell Binding Capacity of JS-Tag and Avi-Tag Constructs The cell binding capacity of the different constructs was tested with the *listeria* strain ScottA according to the 2-step method. The following constructs were used: JS-GFP_CBD511_f3, JS-CBD511_f3 and Avi-Tag-GFP_CBD511_f3. Since the constructs are different in length, equal molar amounts of binding protein were used. The given amounts of fusion proteins were added to 1 ml of test sample (*listeria* from fresh pre-culture in a concentration of $10^4$ CFU/ml, PBST buffer) and mixed briefly. Subsequently, MagPrep-streptAvidin particles (Merck) were added to 50 µg/ml and the mixtures were incubated for 20 min in an overhead rolator at room temperature. The particle-*listeria*-complexes were subsequently collected in a magnetic field at the vessel wall and the supernatant was removed. The particle-*listeria*-complex was washed 1× in 1 ml PBST for 10 min in the overhead rollator, collected in the magnetic field at the vessel wall and each supernatant discarded. The particle-*listeria*-complexes were resuspended in 100 µl PBST and plated on Oxford-Agar (Profos AG). After 24 h at 37° C. the plates were counted and the portion of the *listeria* attached to the magnetic particles were calculated in percent of the introduced cells. All approaches were performed twice and the mean values were calculated. The experiment is depicted in FIG. 4A. It can be seen that the JS-tag constructs bind better than the Avi-tag constructs. Significantly more protein has to be introduced here to achieve the maximum cell binding.

Experiment 4b: Purification of Avi-GFP-CBD511_f2 and JS-CBD511_f2

Both proteins were purified via cation exchange chromatography after expression in *E. coli* HMS174, cell harvest, lysis and ammonium sulphate precipitation. Avi-GFP-CBD511_f2 was coexpressed with BirA.

Experiment 4c: Concentration Dependence of the Cell Binding to the Magnetic Particles It has been analysed from which concentration on of specific binding protein the maximum cell binding is achieved. JS-CBD511_f3 was used as binding protein in the concentrations 0 µg/ml, 0.02 µg/ml, 0.1 µg/ml, 0.5 µg/ml, 1 µg/ml, 2 µg/ml and 3 µg/ml. The experiment was performed analogously to experiment 4a. The result is depicted in FIG. 4B. It has been shown, that the maximum cell binding of basically 100% of all introduced cells were already achieved at very low protein concentrations of 0.5 µg/ml.

Experiment 5: Optimisation of the Nucleotide Sequence in the N-Terminal Region of the JS-Tag Although it has been shown that JS-tag CBD constructs containing the nucleotide sequence of the C-terminal part of the *Klebsiella pneumoniae* oxalacetate decarboxylase are biotinylated in vivo, they exhibited a very poor expression yield for the proteins (see also table 2). As a result the nucleotide sequence encoding the first amino acids of the *Klebsiella* sequence and the starter peptide (MVGA) additionally introduced by our cells was optimized concerning the expression yield without changing the amino acid sequence. From a whole set of different sequence proposals, 5 variants encoding three different nucleotide sequences turned out to be particularly suitable. All variants have in common that they are AT-rich compared to the original sequence if the choice of codons allows this for the respective amino acid. The variants (variations are highlighted in grey) are summarized in table 1.

TABLE 1

Nucleotide variants for the N-terminal sequence region of the JS-tags

| Variant on the level of nucleic acid | Sequence | SEQ ID NO: |
|---|---|---|
| | Nucleotide sequence | |
| Kleb._Oxalacetate decarboxylase | GTG ACC GCC CCG CTG | |
| JS4a | ATG GTT GGT GCA GTT ACA GCT CCG CTG | 54 |
| JS5b, JS5d | ATG GTA GGT GCA GTT ACA GCT CCG CTG | 55 |
| JS10a, JS10c | ATG GTT GGT GCA GTA ACA GCT CCG CTG | 56 |
| | Amino acid sequence | |
| | M V G A V T A P L | |

The variants JS4a, JS5b, JS5d, JS10a and JS10c turned out to be particularly suitable for the expression of fusion constructs of JS-tag and CBD. There were slight differences concerning the expression between the single variants in dependence of the used CBD portion. However, basically all can be used.

Experiment 6: Coexpression of JS-Tag-CBD-Constructs with BirA

It has been tested if a coexpression of BirA (Biotin ligase) is necessary to efficiently biotinylate JS-tag-constructs in vivo.

The construct JS5b-CBD511_f2 was expressed in the expression strain *E. coli* BL21 (DE3) in the vector pet21a. If BirA was coexpressed the plasmid pACYC184-BirA was additionally present. Fresh LB-medium (in 2 l flasks, total amount 4 l to 10 l) was inoculated with overnight cultures of the expression strain, the cells were induced at an $OD_{600}$ of about 0.4 to 0.6 with 1 mM IPTG and harvested after 4 h. 50 µM biotin was added additionally to a portion of the samples during induction. Each construct was tested twice. After harvesting the cells were centrifuged and lysed. The purification was carried out by fractionated ammonium sulphate precipitation and subsequent cation exchange chromatography. The purity of the proteins was documented in SDS-gels.

TABLE 2

Expression and purification yields of different JS-tag-CBD-constructs.

| Construct | BirA coexpression | Expression temperature | Protein mg/g cells |
|---|---|---|---|
| JS-(original) | + | 37° C. | 1.1 |
| JS-(original) | + | 37° C. | 0.4 |
| JS-(5b-variant) | + | 30° C. | 5.0 |
| JS-(5b-variant) | + | 37° C. | 7.0 |
| JS-(5b-variant) | − | 37° C. | 3.8 |
| JS-(5b-varinat) | − | 37° C. | 6.9 |

The expression yield is significantly better concerning the construct JS-5b (see experiment 5), which is optimized in nucleotide sequence, compared to the original sequence from *Klebsiella pneumoniae*. The coexpression of BirA does basically not increase the yield of protein based on the introduced amount of bacteria cells.

Cell Binding Tests with the JS-Tag Constructs with and without Coexpression of BirA.

JS5b CBD511_f2 was introduced in cell binding tests with the *listeria* strain ScottA. 1 ml samples with a *listeria* concentration of $10^3$ CFU/ml were used. As magnetic particles Streptavidin-magnetic-particles (Roche) were used in a concentration of 0.05 mg/ml. Otherwise the performance of the experiment was carried out according to the 2-step-method as described in experiment 3b. Constructs from the expression with and without BirA as well as with and without the addition of additional biotin (50 µM) were analysed. The result is depicted in FIG. 5.

Experiment 7: Comparison of the Bacteria Binding with His-Tag-CBDs and JS-Tag-CBDs

*Bacillus cereus* (DSM345) was freshly inoculated from a preculture and grown at 30° C. in TS-medium up to an $OD_{600}$ of about 1. The bacteria were introduced in the test sample (1 ml) in a concentration of $3 \times 10^3$ CFU/ml. For the his-tag-constructs the buffer was nickel buffer A (20 mM Na-phosphate, 500 mM NaCl, 20 mM imidazol, 0.1% tween 20, pH 7.4), for JS-tag-constructs the buffer was PBST. His-tag-CBDBa and JS-tag-CBDBa were added in a concentration of 1 µg/ml, his-tag-CBD21 and JS-tag-CBD21 were added in a concentration of 0.12 µg/ml and incubated at room temperature for 5 min. Subsequently, Ni-NTA-agarose-beads (Qiagen) and MagPrep-streptavidin-beads, respectively, were added in a concentration of about $8 \times 10^6$ particles/ml, rolling incubated for 20 min and separated for 5 min with the magnetic separator. The magnetic particles were washed with one sample volume of buffer. The washing solution and the supernatant with unbound bacteria were plated on CASO-complete medium plates, as well as the taken up magnetic particles with the bound bacteria. After about 18 h at 27° C. the colonies were counted. 2 experiments each were performed. Approaches without added protein served as controls. The experiment is depicted in FIG. 6.

Whereas the bacteria were bound very specific with the JS-tag-constructs under the given conditions, the yield concerning bound cells was completely insufficient with the his-tag constructs. There was basically no unspecific binding of bacteria concerning both kinds of magnetic particles.

Experiment 8: Enrichment of *Listeria* from Different Media and Buffers, Respectively

*Listeria monocytogenes* EGD was enriched with Avi-CBD511_f2 and JS-CBD511_f2 (5 µg/ml each), respectively, from different media and PBST-buffers, respectively. The *listeria* were incubated in TB-medium up to an $OD_{600}$ of about 1 and predilutions were prepared thereof in the given media or buffers. *Listeria* were used in a concentration of $10^4$ CFU/ml in the test. The cell binding test was carried out according to the 2-step-method with 20 min of rolling incubation with 50 µg/ml MagPrep-streptavidin particles (Merck) and washing once with PBST. The bound and unbound cells were plated on Oxford-Agar and counted after 1 night. Given is the respective mean value of two experiments. The result of the experiment is depicted in FIG. 7.

Experiment 9: Comparison of the Bacteria Binding in Biotin Containing Samples with Strep-Tag-CBDs and JS-Tag-CBDs Biotin is frequently contained in food samples. Since the binding of JS-tags as well as strep-tags to streptavidin competes with biotin, it was analysed, which system is more suitable in biotin containing samples, to enrich bacteria specifically. *Bacillus cereus* (DSM345) was inoculated freshly from a preculture and grown at 30° C. in TS-medium up to an $OD_{600}$ of about 1. Bacteria were introduced into the test approach (1 ml) in a concentration of $1 \times 10^3$ CFU/ml. As a test solution PBST was used with the given concentrations of biotin (0.01 µM, 0.1 µM, 1 µM). JS-tag and strep-tag CBDBa, respectively, were added in a concentration of 20 µg/ml and incubated for about 2 min at room temperature with the bacteria. StreptAvidin-PA-beads were added in a concentration of 50 µg/ml rolling incubated for 20 min and for 5 min separated with a magnetic separator. The magnetic particles were washed with one sample volume of buffer. The washing solution and the supernatant with unbound bacteria were plated on CASO-complete medium plates, as well as the taken up magnetic particles with the bound bacteria and incubated overnight at room temperature. After another 4 hours at 30° C. the colonies were counted. Two experiments each were performed. Samples without added protein served as controls. The result is depicted in FIG. 8. It has been shown that the cell binding in biotin containing samples works significantly better with the JS-tag system compared to the poorer binding strep-tag-system. Specific binding can still be detected at a biotin concentration of 1 µM whereas this is not possible with strep-tag under the same conditions.

Experiment 10: Long Term Stability of the JS-Tag-CBD-Constructs Under Different Conditions Stock solutions of JS-CBD-511_f3 (about 1 mg/ml) and streptavidin magnetic particles (about 1 mg/ml) were incubated under the given conditions and introduced into the cell binding test with *listeria*. The concentration of the magnetic particles in the 1 ml test (PBST buffer) was 50 µg/ml, the protein concentration as given and the used bacteria number was $10^4$ CFU/ml.

Experiment 10a: Binding protein and magnetic beads were stored at −20° C., 4° C., RT (about 23° C.) and 37° C. in 100 mM sodium phosphate, pH 6-7, 2 mM EDTA up to 126 days and used in the given concentrations in the *listeria* binding test. It can be seen that only after 126 days and in this case mainly at an incubation of 37° C. the binding efficiency is significantly reduced.

Experiment 10b: Binding protein and magnetic particles were stored at −20° C., 4° C., RT (about 23° C.) and 37° C. in 10 mM Imidazol, pH 7, 100 mM NaCl plus 30% ammonium sulphate up to 74 days and used in the given concentrations in *listeria* binding tests. It can be seen that the binding efficiency after 74 days of incubation is slightly reduced at all temperatures, but is still over 50%.

Both buffer systems seem to be suitable for the long-term incubation of JS-CBD-constructs and suitable streptavidin magnetic particles.

The results are depicted in FIG. 9.

Experiment 11: Enrichment of *Listeria* from Different Foods

The experiment is depicted in FIG. 10.

Experiment 11a: An overnight culture of *Listeria monocytogenes* ScottA were diluted 1:5 in FDA-Oxoid medium and grown at 37° C. up to an $OD_{600}$ of about 1. Milk and homogenized cheese, respectively, were diluted 1:10 in PBST and inoculated with *listeria* in a concentration of $10^4$ CFU/ml. JS4a-CBD511_f2 was added to Eppendorf-Cups in the given concentrations and mixed with 1 ml sample solution each. As magnetic particles Streptavidin-magnetic-particles (Roche) were used in a concentration of 50 µg/ml and the samples were incubated for 10 min in an overhead rolator. The magnetic particles were separated for 5 minutes in the magnetic separator and subsequently washed ones with 1 ml PBST buffer and taken up in 1 ml of buffer. 100 µl undiluted and 1:10 diluted of the beads fraction and the pooled supernatants (after first magnetic separation and washing step) were plated on Oxford-Agar and incubated at 37° C. overnight. The *listeria* were counted the next day and calculated how many percent of the found bacteria were bound via the JS4a-CBD511_f2 to the magnetic beads, respectively. It has been shown that from milk as well as from cheese the introduced *listeria* cells were basically removed completely already at a concentration of specific binding protein of 0.2 µg/ml JS4b-CBD511_f2. 50% of the bacteria can be removed already at very low protein concentrations of 0.02 µg/ml.

Experiment 11b: 25 g each of smoked salmon and salami were homogenised, diluted 1:10 with LEB-FDA-medium, inoculated with *Listeria innocua* in a concentration of $10^4$ CFU/ml and incubated in a Stomacher-bag for 1 h at room temperature. The used bacterial dilution was plated as a control. 1 ml of each sample of the filtrate of the Stomacher bag was taken and mixed with JS5b-CBD511_f3 (1 µg/ml). No protein was added to the controls. Directly subsequently, 400 µg/ml of PA-streptavidin beads were added and incubated for 20 min in the overhead rolator. The magnetic particles were separated for 5 min in the magnetic separator and subsequently washed once with PBST buffer and taken up in 1 ml of buffer again.

100 µl undiluted and 1:10 diluted of the beads fraction and the pooled supernatants (after first magnetic separation and washing step) were plated on Oxford-Agar and incubated at 37° C. overnight. The *listeria* were counted the next day and calculated how many percent of the found bacteria were bound each via the JS5b-CBD511_f3 to the magnetic particles. It has been shown that from smoked salmon as well as salami more than 90% of the bacteria can be bound.

Experiment 12: Detection of *Listeria* from Foods with the NASBA-Technique

An overnight culture of *Listeria monocytogenes* ScottA was diluted 1:5 in LEB-FDA-medium and grown at 37° C. up to an $OD_{600}$ of about 1. Serial dilutions up to $10^2$ CFU/ml were prepared thereof. 2×60 g of salami were weighed and contaminated with *listeria* in a concentration of 5 CFU/25 g food. To each of the 60 g samples, 540 ml of LX-medium (BioMerieux) was added, the samples were homogenised and incubated in Stomacher-bags for 17 h and 20 h, respectively, at 37° C. Subsequently the bacteria were captured with JS5b-CBD511_f2 in the 1 ml sample from the supernatant of the Stomacher-bag. The supernatant was additionally plated and counted as a control. The binding protein was added in a concentration of 1 µg/ml and incubated for 1 min with the sample. Subsequently PA-streptavidin magnetic particles were added in a concentration of 400 µg/ml and incubated for 20 min in an overnight rolator. The magnetic particles were separated for 5 min in an magnetic separator and subsequently washed 3 times with 1 ml each of TT-buffer (50 mM tris, pH 8.0, 0.1% tween 20). A portion of the magnetic particles with the bound bacteria were plated on Oxford-Agar and counted after an incubation of 15 to 20 h, to obtain the binding efficiency. The result is depicted in part A of the figure. A portion of the magnetic particles with the *listeria* bound via JS-tag-CBDs was introduced for detection in the NASBA. The cells on the beads were lysed with 5 µg/ml of *listeria* specific endolysin in 100 µl lyses buffer A (21%

DMSO, 57 mM Tris, 0.4% Triton X100) for 15 min at room temperature. Subsequently the magnetic beads were separated for 5 min in the magnetic separator and 14 µl of the lysate, each of the NASBA-reaction was used. Test stripes, each for 8 samples were used already carrying precasted *listeria*-specific primer beads. To each sample 5 µl of an enzyme solution for NASBA was added and the reaction performed according to the manufacturer's protocol. As NASBA-system the Nuclisens EasyQ analyser (BioMerieux) was used together with the respective thermo-block. The data are evaluated by a time dependent fluorescence signal. After successful detection reaction the fluorescence signal increases after about 30 min of detection time to a higher level and remains there. 7 NASBA reactions were performed per experimental approach. The NASBA detection (after 17 h of incubation) is depicted in FIG. 11b. It can be seen that in all 7 reactions a positive fluorescence signal is detected and therefore the *listeria* detection via specific RNA primers has worked.

It has been shown that in the described system already after 17 h of incubation of the foods with a *listeria* concentration of 5 CFU/25 g more than 99% of the bacteria can be bound and detected. The detection works conventional via selective plates (see FIG. 11a) as well as via nucleic acid based methods like NASBA, which just takes about 2.5 h after the capturing of the bacteria (see FIG. 11b).

Comparable experiments were also successfully performed with smoked salmon, shrimps, brie, turkey- and pork-sausage and cream cheese from goat.

Experiment 13: Specific Cell Binding of JS-Tag-CBDs, Deriving from *Bacillus* Endolysins For all bacteria strains overnight cultures were grown in complete medium. The overnight cultures were inoculated 1:20 to 1:5 in complete medium (e.g. CASO, LB, TS, TY) and grown further up to an $OD_{600}$ of about 1. Growth temperature for all *bacillus* bacteria was 30° C. for all other strains 37° C. Dilution series were prepared from the precultures. In the test approach (500 µl of volume) the bacteria were used in a concentration of $10^3$ to $10^4$ CFU. For the determination of the accurate cell numbers for each used dilution, the respective controls were plated and counted. JS-tag-CBDBa and JS-tag-CBD21, respectively, each were added in concentrations of 10 µg/ml and 1 µg/ml, respectively, to the test approach (buffer PBST) and incubated about 1 min with the cells. Subsequently the MagPrep-streptavidin particles (Merck) were added in a concentration of 50 µg/ml previously blocked with CASO-tween (0.1%)-solution. The sample with bacteria, binding protein and magnetic particles was incubated for 20 min in an overhead rolator at room temperature. The magnetic particles were separated for 5 min in a magnetic separator, subsequently washed once with 1 ml PBST and subsequently resuspended in buffer. 100 µl each of the resuspended beads fraction with the bound cells and of the pooled fraction of supernatant after magnetic separation and washing solution were plated. After drying, the plates were incubated overnight at the respective growth temperature and counted the next morning and corrected by respective dilution factors. Respectively given is how many percent of the totally bound bacteria are specifically bound via the JS-tag-CBD to the magnetic particles and are separated from the sample. Samples with no added specific binding protein served as control for potentially unspecific binding of the bacteria to the magnetic particles. As further control for the expected cell numbers served the bacteria predilutions, which were also plated and counted. Only experiments were evaluated showing a total number of the recovered cells in the range of 80% to 120% of the totally introduced cells. 2 to 4 experiments were performed per test.

An overview of the respective binding data with different *bacillus* strains and other gram-positive as well as gram-negative bacteria is depicted in table 3.

TABLE 3

Binding capability of JS-CBDBa and JS-CBD21 for different bacteria strains in the cell binding assay

| ProCC | Alternative Name | Species | JS-CBDBa | JS-CBD21 |
|---|---|---|---|---|
| *Bacillus cereus* Group | | | | |
| S1579 | DSM345; ATCC 11778, ATCC 9634 | B. cereus | +++ | +++ |
| S1791 | HER1399; ATCC13472 | B. cereus | o | +++ |
| S1792 | WS2453; ATCC12826 | B. cereus | ++ | ++ |
| S2332 | DSM31; ATCC14579; SBC 10528 | B. cereus | − | ++ |
| S2333 | DSM4312; F4810/72; WSBC 10530 | B. cereus | − | ++ |
| S2334 | NHV391/98; WSBC 10559 | B. cereus | +++ | +++ |
| S2335 | F4370/43; WSBC 10602 | B. cereus | − | + |
| S2336 | DSM 4222; F837/76; SBC 10566 | B. cereus | − | + |
| S2337 | ATCC 10987; WSBC 10865 | B. cereus | + | + |
| S332 | | B. cereus | +++ | +++ |
| S2344 | WSBC 10204; type strain | B. weihenstephanensis | − | + |
| S2345 | WSBC 10210 | B. weihenstephanensis | − | + |
| S2346 | WSBC 10295 | B. weihenstephanensis | − | + |
| S2347 | WSBC 10363 | B. weihenstephanensis | − | + |
| S471 | | B. thuringiensis | − | + |
| S2338 | WS2734; ATCC10792; DSM 2046 | B. thuringiensis | − | + |
| S2339 | WSBC 20822 | B. thuringiensis tenebrionis | +++ | +++ |
| S1586 | DSMZ 299 | B. mycoides | | + |
| S1587 | DSMZ 2048; type strain; ATCC 6462 | B. mycoides | + | ++ |
| S2340 | WS2641; ATCC6462; DSM2048 | B. mycoides | − | + |
| S2341 | WS 3118; NRRLB-617; type strain | B. pseudomycoides | − | + |
| S2342 | WS 3119 | B. pseudomycoides | − | + |

TABLE 3-continued

Binding capability of JS-CBDBa and JS-CBD21 for different bacteria strains in the cell binding assay

| ProCC | Alternative Name | Species | JS-CBDBa | JS-CBD21 |
|---|---|---|---|---|
| | | Other Bacilli | | |
| S2355 | WS3125; ATCC14574; DSM23 | B. badius | − | ++ |
| S2350 | WS1526; DSM11; ATCC4513 | B. circulans | − | +++ |
| S2349 | WS3009; ATCC7050; DSM1 | B. coagulans | − | +++ |
| S2348 | WS1527 | B. firmus | − | +++ |
| S2353 | WS1528; ATCC14580; DSM13 | B. licheniformis | − | ++ |
| S1170 | DSM90 | B. megaterium | ○ | + |
| S2356 | WS1538; DSM36; ATCC842 | B. polymyxa | − | − |
| S2354 | WS1533; ATCC7061; DSM27 | B. pumilus | − | + |
| S2351 | WS1534; ATCC14577; DSM28 | B. sphaericus | − | − |
| S1795 | DSMZ1970 | B. subtilis | − | +++ |
| S0020 | | B. vallismortis | − | +++ |
| | | Gram-positive non-Bacillus Bacteria | | |
| S776 | ScottA (4b) | Listeria monocytogenes | − | ○ |
| S1095 | EGD (1/2a) | Listeria monocytogenes | − | + |
| S459 | | Staphyloccocus aureus | − | ++ |
| S1513 | | Staphyloccocus aureus | − | ++ |
| S1514 | | Staphyloccocus aureus | − | ++ |
| S1520 | | Staphyloccocus aureus | − | +++ |
| S1546 | | Staphyloccocus epidermides | − | + |
| S1503 | | Staphyloccocus epidermides | − | ++ |
| S1510 | | Staphyloccocus epidermides | − | +++ |
| S1508 | | Staphyloccocus epidermides | − | ++ |
| S1509 | | Staphyloccocus hämolyticus | − | ++ |
| S1511 | | Staphyloccocus hämolyticus | − | ++ |
| S1549 | | Staphyloccocus hämolyticus | − | + |
| S1548 | | Staphyloccocus hämolyticus | − | ○ |
| S1176 | | Enteroccocus faecalis | − | ++ |
| S1187 | | Micrococcus luteus | − | + |
| S1798 | | Streptococcus equi spp equi | ++ | +++ |
| S1603 | | Streptococcus mutans | ++ | +++ |
| | | Gram-negative Bacteria | | |
| S484 | | Salmonella tenessee | − | − |
| S169 | | E. coli HMS | − | − |

ProCC: PROFOS Culture Collection;
Binding: 0%: −; <10%: ○; 10%-30%: +; 30%-60%: ++; 60%-100%: +++

As expected, both CBDs show no binding to gram-negative bacteria. However, the binding specificities of the CBDs both isolated from Bacillus cereus phages are unexpectedly completely different. It has been shown that CBDBA is very specific for bacilli from the Bacillus cereus group. Beyond this group only 2 streptococcus strains are recognized. However, CBD21 exhibits an exceptionally broad binding specificity for gram-positive bacteria. All representatives of the Bacillus cereus group are bound and additionally all further tested bacilli except for B. sphaericus and B. polymyxa. Exceptional is that also gram-positive bacteria from other families were bound. The 6 tested families, characterized in that they exhibit a high pathogen potential were all recognized. CBD21 is therefore particularly suitable to enrich, remove and detect pathogen bacteria in different areas where they pose a problem. In contrast to further tested fragments, which also derived from endolysin plyB21, the herein depicted fragment (SEQ ID NO: 19) was characterized by an increased stability and reduced aggregation susceptibility.

Experiment 14: Specific Binding of Bacillus cereus from a Mixture of Bacteria

Overnight cultures were grown in complete medium of the following bacteria: Bacillus cereus (DSM345), Salmonella tennessee, Listeria monocytogenes (ScottA), Staphylococcus aureus, E. coli HMS174 (DE3). The overnight cultures were inoculated in fresh medium and grown for about 3 h at 37° C. and 30° C. (bacilli), respectively, up to an $OD_{600}$ of about 1. The strains were used in the test in a dilution of about $10^3$ CFU/ml. The respective dilutions were plated and counted as a control. The test mixture has 1 ml and was performed in PBST (20 mM Na phosphate, 120 mM NaCl, pH 7.4, 0.1% Tween 20). As specific binding protein JS-tag-CBDBa was provided in a concentration of 20 µg/ml. For the control experiments only PBST was added instead of protein. 10 µl each of the bacteria pre-dilution was added such that the concentration of the bacteria in each sample was about $10^3$ CFU/ml. The bacteria were incubated with the cells for 1 min. Subsequently 100 µg/ml magnetic PA-streptavidin beads (Microcoat) were added and the samples were rolling incubated for 20 min at room temperature. The magnetic particles were collected for 5 min in a magnetic separator and the supernatants were taken. The separated magnetic particles were washed once for 5 min with 1 ml PBST. The washing solution was pooled with the supernatants. The magnetic beads were again made up to 1 ml with PBST. 100 µl each from different dilutions were plated on the one hand on CASO-plates (casein, soy bean extract; complete medium, Merck) and on the other hand on PEMBA-plates (selective medium for Bacillus cereus, contains polymyxin B, egg yolk, mannitol) and incubated at 27° C. for about 18 h and subsequently counted. 2 mean values each were determined from 2 experiments. The total number of recovered cells resulted from the sum of cells bound to the magnetic particles and the cell which remained in the supernatant and the washing solution, respectively. The plated cell dilutions were used as a control. The result is depicted in FIG. 12. It has been shown that only after adding the specific CBD *Bacillus cereus* was enriched from the sample, whereas without adding the protein no bacteria were bound to the magnetic particles. It has also been shown that only *Bacillus cereus* was bound via the beads, whereas the other bacteria just grew on the CASO-plates, on which the supernatant was plated.

Experiment 15: Enrichment of *Bacillus cereus* from Carbohydrate Containing Foods As food sample, precooked express rice (top-long grain express rice, Uncle Ben's) was used. 5 g of precooked express rice was sterile transferred into a Stomacher-bag, with 50 ml TSPB-medium (TS-complete medium with 0.01 mg/ml polymyxin B) and homogenised for 1 min. An overnight culture of Baciullus cereus (DSMZ345) was inoculated at 30° C. in TS-medium. 2 ml of the overnight culture was transferred in 10 ml fresh TSPB-medium and incubated until an $OD_{600}$=0.8 was achieved. 990 µl of the food sample from the Stomacher-bag filtrate was spiked with 10 µl each of different dilutions of the bacilli precultures such that the *bacillus* concentration in the food sample was $10^2$, $10^3$, or $10^4$ CFU/ml. TSPB-medium was spiked as a control. After 5 min of incubation at room temperature 10 µg JS-tag-CBDBa was added per sample and mixed thoroughly. The control samples obtained no protein. After about 1 min 400 µg of streptavidin of PA-magnetic beads (Microcoat) were added and the samples were rolling incubated for 20 min at room temperature. The magnetic beads were collected for 5 min in a magnetic separator and the supernatants were taken. The separated magnetic particles were washed twice for 5 min with 1 ml PBST. The washing solutions were pooled with the supernatants. The magnetic beads were again made up to 1 ml with PBST. 100 µl each of the different dilutions of the samples with the magnetic particles and the supernatants, respectively, were plated onto selective PEMBA-plates, subsequently incubated overnight at 30° C. and then counted. 2 plates each were plated in parallel. The result is depicted in FIG. 13. It shows that basically all *Bacillus cereus* cells are selectively bound from the food sample as well as from TSPB-medium to the JS-tag-CBDBa and subsequently to the magnetic particles, whereas in the supernatant and in the washing solutions almost no *Bacillus cereus* cells remained. In the control samples without protein, no bacilli were bound unspecifically to the magnetic particles.

Experiment 16: Enrichment of *Bacillus cereus* from Blood

*Bacillus cereus* (DSMZ345) was grown overnight at 30° C. in TB-medium. Fresh TB-medium was inoculated 1:10 and the bacteria were grown up to an $OD_{600}$ of about 1. 0.5 ml each of citrate, EDTA or heparin blood was mixed with 0.5 ml PBST each. All additives in the blood served as anticoagulants. Citrate-blood: 0.106 M citrate was diluted 1:10 with blood. EDTA-blood: 1.2-2 mg EDTA/ml blood. Heparin blood: 10-30 I.U. heparin/ml blood. The 1 ml samples of the buffered blood were spiked with 10 µl each of *Bacillus cereus* preculture such that the bacteria concentration was about $10^3$ CFU/ml. Therefore 5 µl of a JS-tag-CBD21-protein solution (2 mg/ml) was added and vortexed briefly. The controls obtained no protein. Subsequently 40 µl of magnetic particles (streptavidin-PA-beads, Microcoat, 10 mg/ml) were added and the samples were rolling incubated for 20 min at room temperature. The magnetic particles were separated in a magnetic separator for 5 min. The supernatant, which contains the non-bound bacteria was taken and the beads washed once with 1 ml of PBST (5 min). The washing solution was pooled with the supernatants after magnetic separation. 1 ml PBST was added to the magnetic beads with the bound complex of JS-tag-CBD and bacteria. 100 µl each of a 1:10 dilution of the pooled supernatants and the solution containing the magnetic particles was plated on selective PEMBA-plates, incubated for about 18 h and counted. Mean values of 2 experiments each were formed. The result of the experiment is depicted in FIG. 14. It has been shown that with the help of the JS-tag-CBD21 almost all bacilli from the blood could be removed. It has been shown in the controls without protein that only concerning blood samples containing heparin a certain percentage (about 25%) of unspecific binding to the magnetic particles appeared. Concerning citrate blood and EDTA-blood the portion of unspecific binding was very low.

Experiment 17: Binding of Clostridii with JS-tag Constructs of the CBD3626

Based on the endolysin of the *Clostridium perfringens* phage Φ3626, Ply3626, described in the literature (Zimmer et al., 2002, Appl. Environm. Microbiol., 68, 5311-5317), different variants of a potentially suitable CBD3626 with JS-tag was prepared with molecular biological techniques. Since the expression of all constructs was very poor at the beginning, a synthetic gene was prepared optimized on the different codon uses in *clostridium* and *E. coli*. It turned out that conventional variants cloned with his-tag were only very poorly soluble; however, the variants with JS-tag were better soluble. The variants which turned out to be suitable to be expressed stable and soluble such that they could be purified subsequently and used in an functioning binding test with *Clostridium perfringens* cells, are summarized in table 4. The cloning was carried out in the vector Pet21 d each. The expression was carried out in the strain *E. coli* HMS174 at 30° C. in LB-medium with ampicillin and chloramphenicol under coexpression of birA on another plasmid.

TABLE 4

| Protein-Shortcuts | Portion of Ply3626 (amino acid) | JS-Tag Variant | GFP | Molecular Weight (kDa) |
|---|---|---|---|---|
| JS4a_GFP_CBD3626_150 | 150-347 | JS(4a) | + | 58 |
| JS10a_GFP_CBD3626_150 | 150-347 | JS(10a) | + | 58 |
| Js4a_GFP-CBD3626_178 | 178-347 | JS(4a) | + | 55 |
| Js10a_GFP-CBC3626_178 | 178-347 | JS(10a) | + | 55 |
| Js4a_CBD3626_150 | 150-347 | JS(4a) | − | 23 |
| Js10a_CBD3626_178 | 178-347 | JS(10a) | − | 20 |

For the binding test a preculture of *Clostridium perfringens* was grown at 45° C. overnight in TYG-medium (Trypton, yeast extract, glucose) in an anaerobic box. The binding tests were performed in 1 ml PBST buffer at room temperature. *Clostridium* cells were provided in a concentration of about $10^4$ CFU/ml and the different JS-tag-CBD3626 constructs were added in a concentration of 25 µg/ml, mixed and incubated for about 2 min. Subsequently, PA-streptavidin beads (Microcoat) were added in a concentration of 100 µg/ml and rolling incubated for 10 min. Samples were taken from each CBD constructs containing GFP as a marker and analysed concerning binding under the fluorescence microscope. The result is depicted in FIG. 15.

Experiment 18: Binding of Staphylococci with Specific JS-Tag-CBD-Constructs

Overnight cultures of *staphylococcus* strains were diluted 1:10 in BHI-medium and incubated at 30° C. up to an $OD_{600}$ of about 1. The cells were diluted in medium and used in a concentration of $10^4$ CFU/ml in the test (test approach 500 µl, PBST buffer). Specific binding protein JS5_bCBDUSA was added in a concentration of 10 µg/ml and incubated with the cells for 20 min at room temperature. Subsequently PA-strepativin beads (Microcoat) were added in a concentration of 200 µg/ml and incubated for 45 min in an overhead rolator. The magnetic particles with the bound cells were incubated 5 min in the magnetic separator, washed once with 1 ml buffer and resuspended again in 500 µl of buffer. The magnetic particles and the pooled supernatants were plated on CASO-plates and incubated overnight at 37° C. The plates with Staphylococcus aureus and S. haemolyticus could be counted after 16 h, the plates with S. epidermidis not until after 24 h. The portion of bound staphylococci was analyzed in comparison to the totally found bacteria.

TABLE 5

| Strain | JS5b_CBDUSA |
| --- | --- |
| Staphylococcus aureus | +++ |
| Staphylococcus haemolyticus | ++ |
| Staphylococcus epidermidis | + |

% Cell binding: <10%: o; 10%-25%: +; 25%-50%: ++; >50%: +++

With the JS5b-CBDUSA-construct different strains of staphylococci can be bound, wherein S. aureus binds best.

Experiment 19: Polypeptide constructs according to the present invention with CBD and JS-tag bind staphylococcus cells significantly better in the bead-sb-binding test than to a CBD with a combination of Strep-tag and His-tag (NS-HIS)

The performance of the experiment was carried out in the cell binding test analogously to experiment 18. JS-tag polypeptide constructs according to the present invention of the cell binding domain of the CBDPitti26 (SEQ ID NO: 28) were used compared to a construct, which contained a strep-tag for the biotin binding as well as a his-tag (combination NS-his). The CBD constructs have the NS-his and JS-tag (variant 5b) at the N-terminus, respectively, followed by a linker sequence (AGAGAGAGAGSEL) and the CBDPitti26 sequence. Pitti26 is a self-isolate of a staphylococcus phage. The polypeptide constructs were dialysed freshly prior to the test, the protein concentration was determined using UV absorption measurement and the proteins were introduced in the test in a concentration of 10 µg/ml. The binding behaviour to 3 different staphylococcus strains is depicted in table 6.

TABLE 6

| CBD Construct | Staphylococcus aureus (Patient Isolate) | Staphylococcus epidermidis (DSMZ 20044) | Staphylococcus haemolyticus (DSMZ 20263) |
| --- | --- | --- | --- |
| NS-His-CBDPitti26 | 0% | 1.1% | 0.0% |
| JS-CBDPitti26 | 1.0% | 61.3% | 5.0% |

Whereas with the JS-tag-CBD-construct according to the present invention cell binding could be detected at all 3 staphylococcus strains, even though with significant preference for Staphylococcus epidermidis cells, concerning the construct with strep-tag and his-tag just for the Staphylococcus epidermidis cells a very weak binding could be achieved under the same conditions. This shows that the constructs according to the present invention are significantly better suitable for the binding of bacteria cells than CBDs coupled to other tags.

Experiment 20: Detection of the Staphylococci Binding by Staphylococcus Specific JS-Tag-CBD Constructs in the Cell Binding Test Analogously to the experimental design described in experiment 18, a multitude of different staphylococcus strains were tested under usage of 3 different JS-tag-CBD constructs specific for staphylococcus. The CBD portions of the different constructs derive from the phage ΦSA2usa—JS-CBDUSA, and from endolysins from the phage self-isolates PlyOpf—JS-CBDOpf—and PlyPitti20—JS-CBDPitti20, respectively. The polypeptide sequences can be found under the SEQ ID NOs 21, 31, and 27, respectively. The results of the experiments are depicted in FIG. 16.

Figure 16A:
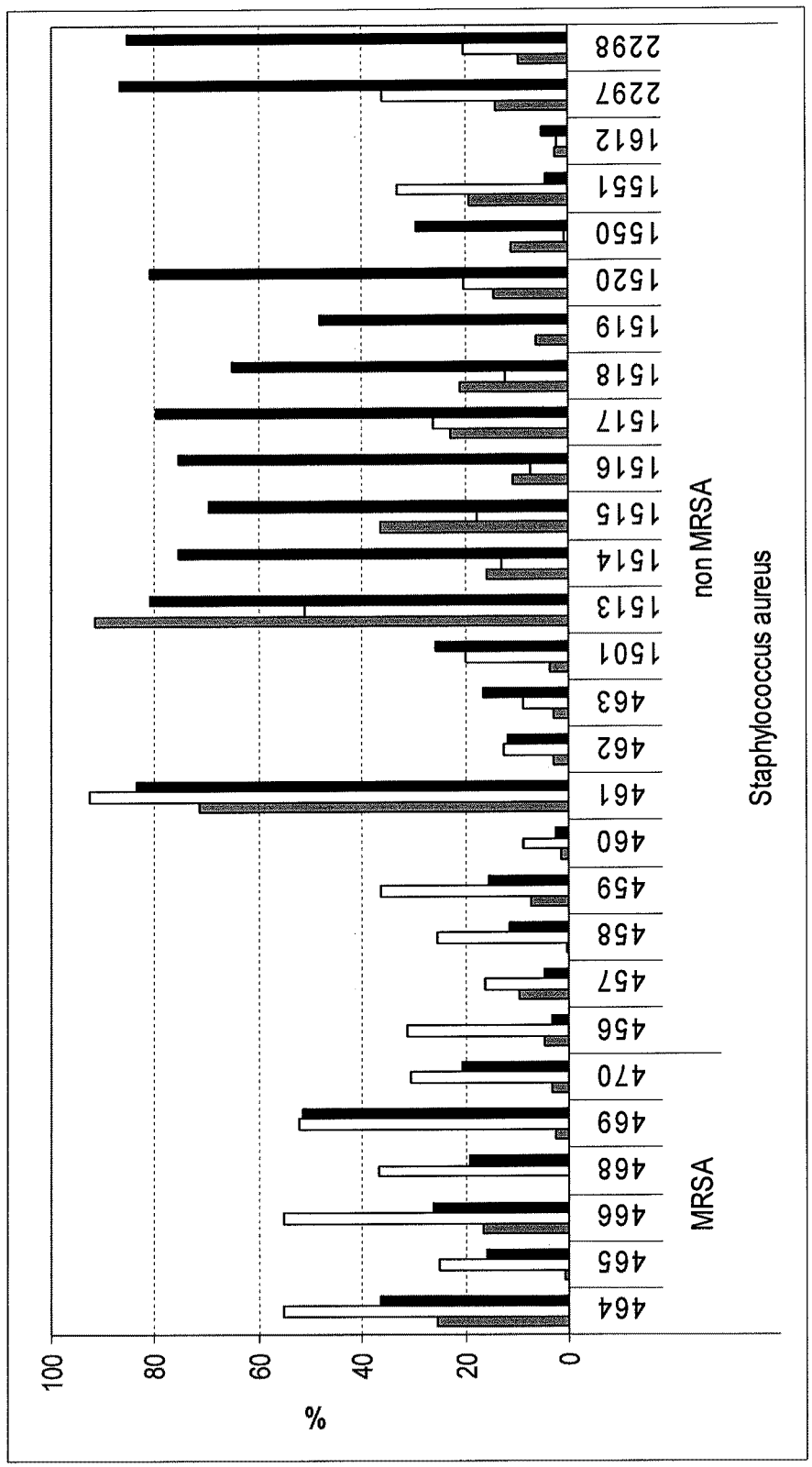
Figure 16B:
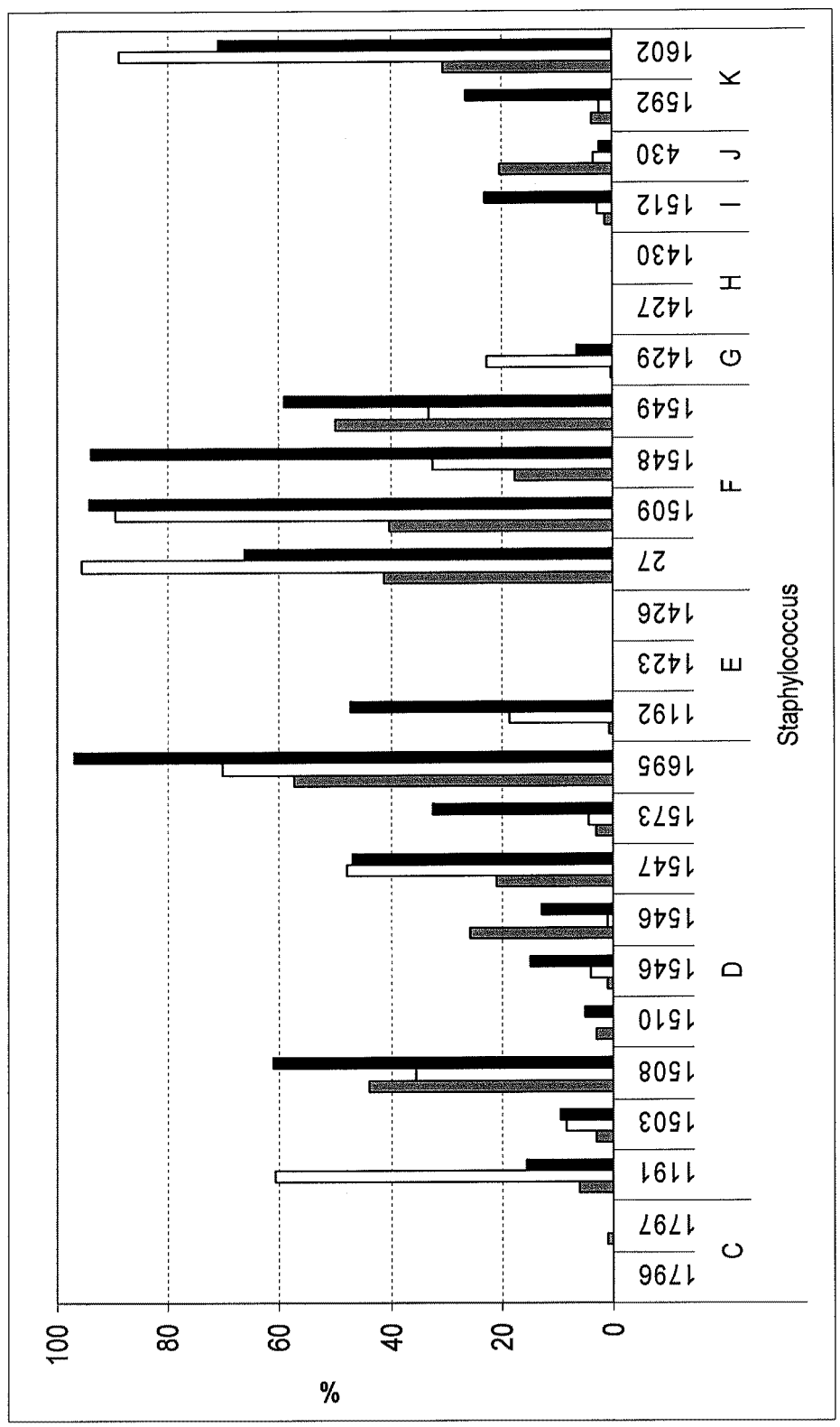

The polypeptide constructs according to the present invention JS-CBDUSA, JS-CBDOpf and JS-CBDPitti20 bind a multitude of staphylococcus strains specifically in the beads binding test. Thereby Staphylococcus aureus MRSA strains are bound similarly good as non-MRSA strains (FIG. 16A). However, it can be noted that tendentially JS-CBDOpf binds the MRSA-strains better, whereas JS-CBDUSA binds the non-MRSA strains better. FIG. 16B summarizes the binding of the 3 staphylococcus JS-CBD-constructs according to the present invention to a set of further staphylococcus strains, which do not belong to the species Staphylococcus aureus. Strains of the species Staphylococcus carnosus, Staphylococcus sciuri and Staphylococcus equorum (with one exception) are thereby not specifically bound, strains of the species Staphylococcus epidermidis, Staphylococcus haemolyticus, Staphylococcus saprophyticus, Staphylococcus simulans, Staphylococcus warneri and Staphylococcus xylosus are in contrast specifically bound. This shows that the used JS-tag-CBD-constructs according to the present invention are suitable to specifically and efficiently bind a large amount of human pathogen staphylococcus strains.

Experiment 21: Detection of the Cell Binding to JS-Tag-CBD-Constructs with the Help of the Peroxidase Test The peroxidase test is based on a principle that a measuring signal can only be detected if the used StrepTactin-HRP (Horse Radish peroxidase)-conjugate (IBA, Göttingen) can bind via the StrepTacin portion to biotin. This biotin is covalently bound to the biotinylated JS-tag of the polypeptide constructs according to the present invention, which in turn have specifically bound to bacteria cells in the experimental approach and is therefore present in the pellet fraction, which are retained in the centrifugation steps. Non-bound JS-tag-CBD-constructs would be discarded with the respective centrifugation supernatants and would therefore not give a signal. The JS-tag-polypeptide-constructs according to the present invention were dialysed against TE-buffer (20 mM Tris, 50 mM NaCl, 5 mM EDTA; pH 7.0) overnight prior to the use in the peroxidase test and subsequently the protein concentration was determined via UV-absorption by means of the specific extinction coefficient. Microtiter plates (Deepwell) were blocked by incubation with 600 µl PBST each for 1 h at 37° C. Subsequently 200 µl each of bacteria preculture and BHI-medium (as control), respectively, were pipetted into the wells and respective amounts of protein solution (protein concentration 10 µg/ml) and buffer (as control), respectively, were added and incubated for 15 min at room temperature. Tripled determinations were performed each. After incubation the plates were centrifuged for 10 min at 4° C. in a table centrifuge (3,600 rpm), the supernatants were taken and discarded and the pellets washed again with 200 µl PBST. Subsequently the pellets are resuspended in 200 µl StrepTactin-HRP-conjugate solution (1:5000 diluted in PBST) and incubated for 30 min at room temperature. The samples are centrifuged again, washed twice with 200 µl PBST each and the thereby supernatants are discarded each. After the second washing step the pellets are taken up in 200 µl ABTS-reaction solution each and the colour reaction is measured via the absorption at 405 nm (corrected by the background absorption at 600 nm) over maximally 30 min. The ABTS reaction solution is composed as follows: 18 ml Mc-Ilvains-buffer (0.1 M citric acid, 0.2 M Na₂HPO₄, pH 5.0) plus 2 ml of 1% ABTS (2,2 azino-bis(3-ethyl)benzthiazolin 6-sulfon acid) in water plus 100 μl H₂O₂ (1% solution).

Results of the peroxidase test by use of different CBD-constructs according to the present invention are depicted in FIG. 17. JS-CBDOpf and JS-CBDPitti20 are CBD-constructs from *staphylococcus* phage self-isolates. JS-CBDUSA derives from the phage ΦSA2usa. The CBD portions of the staphylolytic enzymes ALE-1 and lysostaphin in the constructs JS-CBDALE-1 and JS-CBDLS derive from the bacteria strains *Staphylococcus capitis* EPK1 and *Staphylococcus simulans*, respectively. However, the respective genes were prepared synthetically and adapted to the *E. coli* codon usages for better expression of the protein.

Figure 17A:
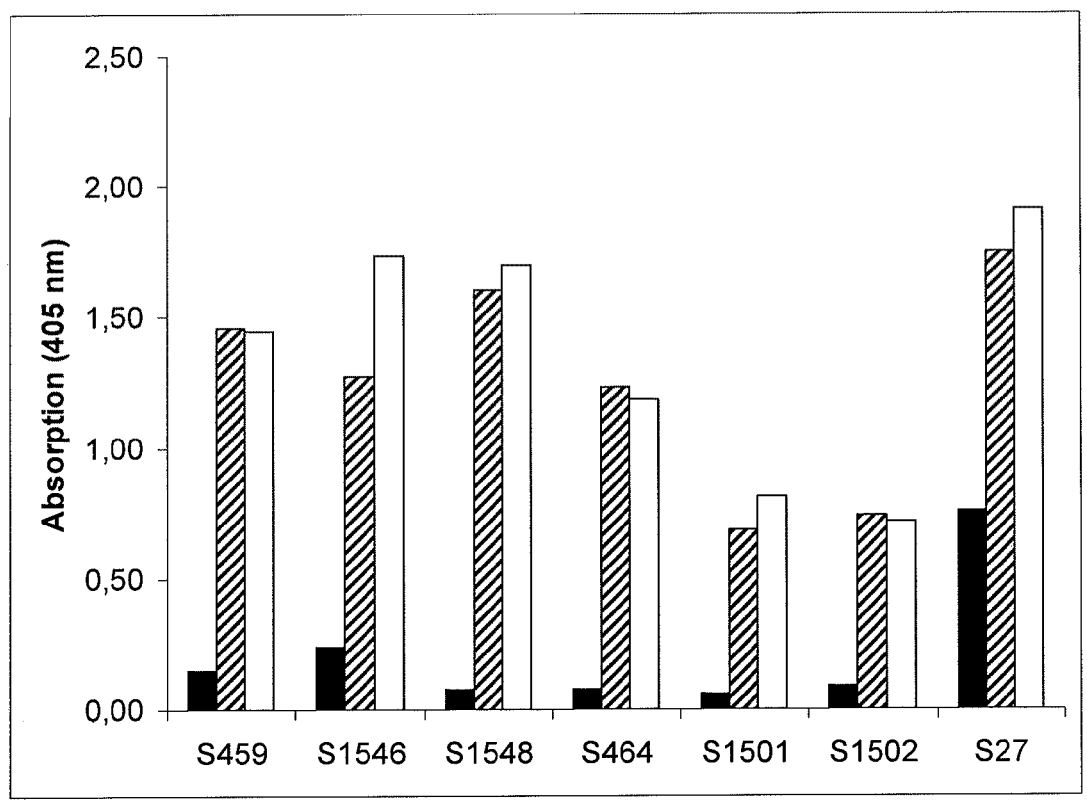

As depicted in FIG. 17A, JS-CBDALE-1 (SEQ ID NO: 50) and JS-CBDLS (SEQ ID NO: 41) bind specifically and with high efficiency different coagulase positive *S. aureus* strains (MRSA and non-MRSA) as well as the coagulase negative *S. epidermidis* and *S. haemolyticus*. Both JS-tag-constructs bind the staphylococci with about similar efficiency.

Figure 17B:
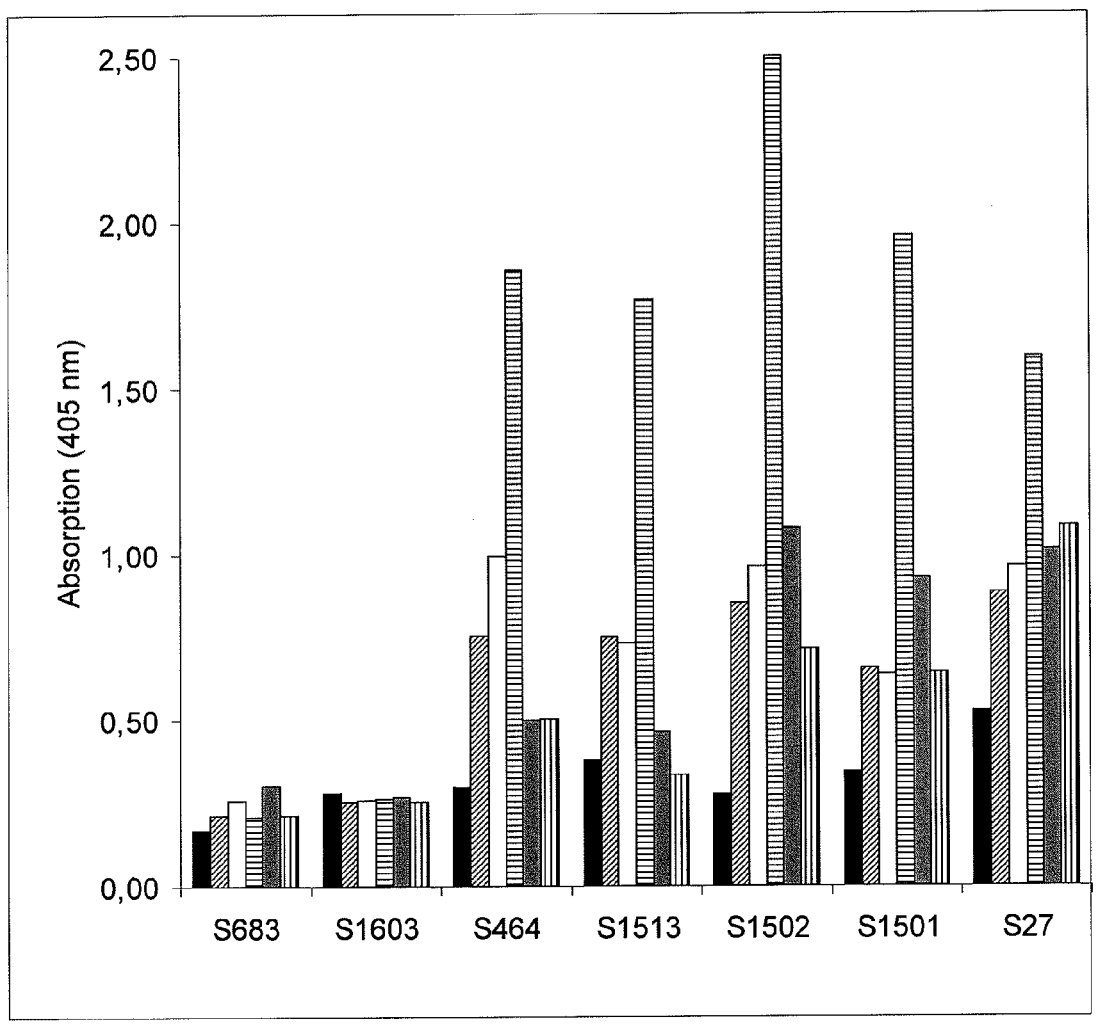

FIG. 17B depicts that the polypeptide JS-CBDALE-1 (SEQ ID No 50), JS-CBDLS (SEQ ID No 49), JS-CBDPitti20 (SEQ ID No 47), JS-CBDOpf (SEQ ID No 51) as well as JS-CBDUSA (SEQ ID No 46) according to the present invention specifically bind different *Staphylococcus* strains such as *S. aureus* (MRSA and non-MRSA) and *S. haemolyticus* strains in the peroxidase test whereas the gram-negative *E. coli* strain but also the gram-positive pathogen strain *Streptococcus mutans* are not bound. Particularly to emphasize is the strong cell binding by the polypeptide-construct JS-CBDPitti20.

Experiment 22: Detection of the Cell Binding to *Enterococcus* Specific JS-Tag-CBD-Constructs with the Help of the Peroxidase Test The performance of the peroxidase test was carried out as described in experiment 21. The result of the peroxidase test by use of different CBD-constructs according to the present invention is depicted in FIG. 18. JS-CBDEF0355 and JS-CBDEF293 are 2 JS-tag-CBD-constructs according to the present invention, in which the CBDs derive from 2 putative prophage-endolysins, which can be found in the completely published genome of the strain *Enterococcus faecalis* V583 (Accession No: NC_004668) under the locus tags EF_0355 and EF_1293, respectively. However, the respective genes were prepared synthetically and adapted to the *E. coli* codon usage for a better expression of the proteins. The CBDs were obtained such that from the complete endolysin sequence the conserved domains for the EADs were deleted and subsequently searched for potential domain linkers within the proteins with sequence analysis software. As a new linker between JS-tag and CBD, the sequence AGAGAGAGSEL (SEQ ID No. 35) was subsequently introduced each. 10 μg/ml JS-Tag-CBD-construct was used each in the test. The results of the experiments are depicted in FIG. 18.

Figure 18A:
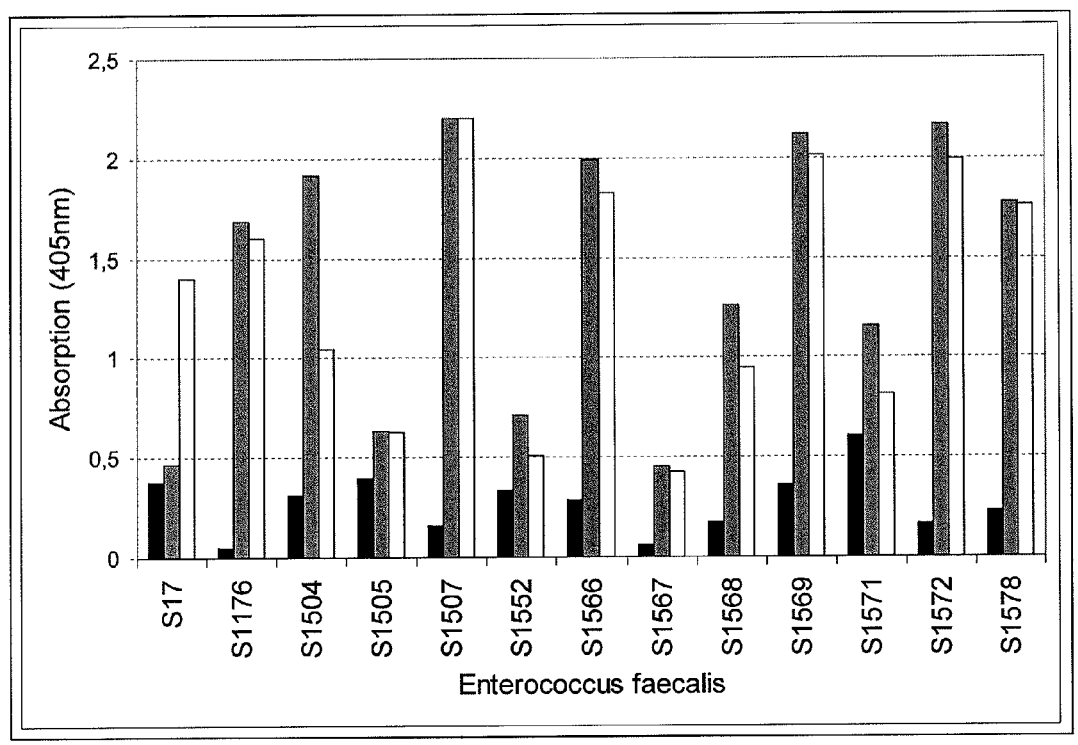

FIG. 18A shows that all tested *Enterococcus faecalis* strains in the peroxidase test are specifically bound, since the controls without addition of the JS-tag-CBD-constructs give a significantly lower measuring signal. The both constructs JS-CBDEF0355 and JS-CBDEF1293 give very similar results concerning most of the strains.

Figure 18B:
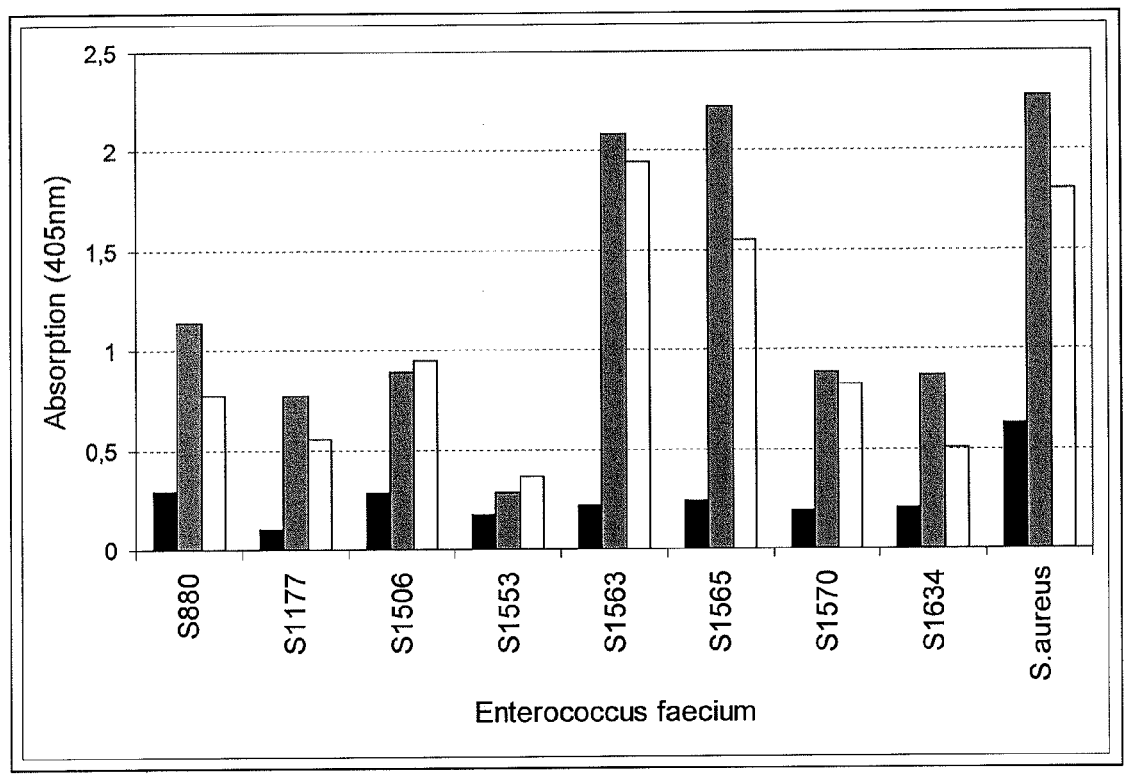

FIG. 18B shows that the tested *Enterococcus faecium* strains are specifically bound, although they partially give slightly lower absorption signals. A *staphylococcus aureus* strain was also bound with good efficiency such that the binding for the species *enterococcus* is not very specific. However, this behaviour was already known from Yoong et al. (J. Bact., 2004, 186, 4808-4812) where it has been shown that besides enterococci, also streptococci and staphylococci are bound.

The invention claimed is:

1. A method for the enrichment, for the removal, for the capture and/or for the detection of bacteria from a sample, comprising the steps:
   a) contacting and/or incubating a sample with a biotinylated polypeptide comprising
      (i) an enzymatically non-active cell wall binding domain of a phage tail protein selected from the group consisting of SEQ ID NO: 19-33, and
      (ii) a domain comprising a sequence selected from the group consisting of SEQ ID NO: 1-18,
   b) contacting and/or incubating polypeptide-bacteria-complexes obtained in step a) with a carrier supplied with a biotin-binding substance, and
   c) separating a carrier-polypeptide-bacteria-complex, obtained in step b), from the sample.

2. The method according to claim 1, wherein the biotin-binding substance comprises avidin or streptavidin.

3. The method according to claim 2, wherein the method is carried out via magnetic, chromatographic or batch-methods.

4. The method of claim 1, wherein the polypeptide comprises the sequence of the CBD21 as depicted in SEQ ID NO: 19 or the polypeptide sequence of the CBDOpf as depicted in SEQ ID NO: 31.

5. The method according to claim 1, further comprising washing unspecifically attached components of the sample from the carrier-polypeptide-bacteria-complex.

6. The method according to claim 5, further comprising separating the carrier from the polypeptide-bacteria-complex.

7. The method according to claim 6, further comprising detecting the bacteria.

8. The method according to claim 7, wherein the detection is carried out via selective growth conditions, nucleic acid based methods, detection of the bacteria cell wall and its components, respectively, detection of bacteria components via a further specific cell wall binding domain coupled to a marker, and/or via a combination of microbiological, morphological and/or biochemical detection methods.

9. The method according to claim 8, wherein the detection of the bacteria cell wall and its components, respectively, is carried out via cell binding domains of endolysins, antibodies or via FTIR.

10. The method according to claim 8, wherein the detection of the bacteria components is carried out via ELISA, enzyme activity, multi-locus enzyme electrophoresis (MEE) or a bioluminescence assay.

* * * * *